US008377913B2

(12) United States Patent
Von Geldern et al.

(10) Patent No.: US 8,377,913 B2
(45) Date of Patent: Feb. 19, 2013

(54) VITAMIN D RECEPTOR ACTIVATORS AND METHODS OF MAKING

(75) Inventors: Thomas W. Von Geldern, Richmond, IL (US); Jufang H. Barkalow, Deerfield, IL (US); David M. Barnes, Bristol, WI (US); Anthony R. Haight, Wadsworth, IL (US); John E. Hengeveld, Kenosha, WI (US); Xiaofeng Li, Gurnee, IL (US); Maureen A. McLaughlin, Kenosha, WI (US); William T. Noonan, Mason, OH (US); Zhonghua Pei, Burlingame, CA (US); Jinshyun Ruth Wu-Wong, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 1141 days.

(21) Appl. No.: 12/205,998

(22) Filed: Sep. 8, 2008

(65) Prior Publication Data
US 2009/0131379 A1    May 21, 2009

Related U.S. Application Data

(60) Provisional application No. 60/989,167, filed on Nov. 20, 2007.

(51) Int. Cl.
 *A61K 31/59* (2006.01)
 *C07C 401/00* (2006.01)
 *A61P 9/00* (2006.01)
 *A61P 35/00* (2006.01)
(52) U.S. Cl. .................................. 514/167; 552/653
(58) Field of Classification Search .............. 514/167; 552/653
See application file for complete search history.

(56) References Cited

U.S. PATENT DOCUMENTS

| 5,614,512 A | 3/1997 | DeLuca et al. |
| 2005/0004085 A1 | 1/2005 | DeLuca et al. |

FOREIGN PATENT DOCUMENTS

| JP | 63 208568 | | 8/1988 |
| JP | 02 215766 | | 8/1990 |
| WO | 89 10352 | A1 | 11/1989 |
| WO | 91 15475 | A1 | 10/1991 |
| WO | 98/52574 | A1 | 11/1998 |
| WO | 01/56981 | A1 | 8/2001 |

OTHER PUBLICATIONS

Adorini, "Intervention in autoimmunity: The potential of vitamin D receptor agonisits",Cellular Immunology, 233, 115-124 (2005).
Agarwal, et al., "Antiproteinuric effect of oral paricalcitol in chronic kidney disease",Kidney International, 68, 2823-2828 (2005).
Aihara, et al., "Disruption of Nuclear Vitamin D Receptor Gene Causes Enhance Thrombogenicity in Mice", Journal of Biol Chem, 279, 35798-35802 (2004).

Allewaert, et al., "Synthesis and Biological Evaluation of 23-Oxa-, 23-Thia- and 23-Oxa-24-oxo-1α,25-dihydroxyvitamin D3", Bioorganic & Medicinal Chemistry Letters, 13, (9), 1859-1862 (1993).
Anderson, et al., Expression of VDR and CYP24A1 mRNA in Human Tumors, Cancer Chemother Pharmacol 57, 234-240 (2006).
Beer, et al., "High dose calcitriol may reduce thrombosis in cancer patients", British Journal of Haematology, 135, 392-394 (2006).
Block, et al., "Cinacalcet for Secondary Hyperparathyroidism in Patients Receiving Hemodialysis", New Eng J Med, 350(15), 1516-1525 (2004).
Chertow, et al, "Cinacalcet Hydrochloride (Sensipar) in Hemodialysis Patient on Active Vitamin D Derivatives with Controlled", Clin J Am Soc Nephrol, 1 305-312 (2006).
Deeb, et al., "Vitamin D signalling pathways in cancer: potential for anticancer therapeutics", Nature Reviews Cancer, 7, 684-700 (2007).
Dennis, et al., "Doxercalciferol Treatment of Secondary Hyperparathyroidism," The Annals of Parmacotherapy, 40, 1955-1965 (2006).
Fryer, et al., Systemic Activation of the Calcium Sensing Receptor Produces Acute Effects on Vascular Tone and Circulatory Function in Uremic and Normal Rats: Focus on Central Versus Peripheral Control of Vascular Tone and Blood Pressure by Cinacalcet, JPET, 323(10), 217-226 (2007).
Fryer, et al., "Differential Inhibition of Renin mRNA Expression by Paricalcitol and Calcitriol in C57/BL6 Mice", Nephron Physiol, 106, 76-81(2007).
Hatcher, et al., "A-ring hydroxymethyl 19-nor analogs of the natural hrmone 1α, 25-dihydroxyvitamin D3: Synthesis and preliminary biological evaluation", Bioorganic and Medicinal Chemistry, 13, 3964-3976 (2005).
Hendy, et al., "New insights into mineral and skeletal regulation by ative forms of vitamin D, "Kidney International, 69, 218-223 (2006).
Hudson, "Secondary Hyperparathyroidism in Chronic Kidney Disease: Focus on Clinical Consequences and Vitamin D Therapies," Annals of Pharm, 40, 1584-1593 (2006).
IUPAC__1974__Recommendationsfor__Sec__E,__Fundamental__ Stereochemistry,__Pure__Appl__Chem,45,13-30__(1976).
James, et al., "Leukemia Cell Differentiation: Cellular and Molecular Interactions of Retinoids and Vitamin D", Gen Pharmac, 32(1), 143-154 (1999).
Klein, et al., "Der Stereochemische Verlauf Der Alkalischen Epoxydation Von α, β-Ungesattigten Carbonyl-Verbindungen Der Cyclischen Monoterpen-Reihe", Tetrahedron, 11, 1091-1099 (1963).
Kutner, et al, "Vitamin D C-22 Aldehydes, New Key Intermediates for the Synthesis of Side Chain Modified Vitamin D Analogues", Tetrahedron Letters, 28(49), 6129-6132 (1987).
Kutner, et al., "Novel Convergent Synthesis of side-chain-modified analogs of 1.alpha., 25-dihydroxycholecalciferol and 1.alpha.,25-dihydroxyergocalciferol", J Org Chem, 53(15)m 3450-3457 (1988).

(Continued)

*Primary Examiner* — Sabiha Qazi
(74) *Attorney, Agent, or Firm* — Glen Gesicki

(57) ABSTRACT

The invention relates to compounds that are vitamin D receptor activators, compositions comprising such compounds, methods of using such compounds and compositions, processes for preparing such compounds, and intermediates obtained during such processes.

5 Claims, 4 Drawing Sheets

OTHER PUBLICATIONS

Lazar, et al., Long-Term Outcomes of Cinacalcet and Paricalcitol Titration Protocol for Treatment of Secondary Hyperparathyroidism, Am J Nephrol, 27, 274-278 (2007).

Li, et al., "Vitamin D: a negative endocrine regulator of the renin-angiotensin system and blood pressure, "The J of Steroid Biochem and Molec Biolology, 89-90, 387-392 92004).

Lou, et al., The role of Vitamin D3 metabolism in prostate cancer, Steroid Biochemistry and Molecular Biology, 92, 317-325(2004).

Masood, et al., Kaposi sarcoma is a therapeutic target for vitamin D3 receptor agonist, Blood, 96(9), 3188-3194 (2000).

Nakane, et al., "Differential effect of Vitamin D analogs on bone formation and resorption," Journal of Steroid Biochemisty and Noloecular Biology, 98, 72-77 (2006).

Ohsawa, et al., "1a,25-Dihydroxyvitamin D3 and Its Potent Synthetic Analogs Downregulate Tissue Factor and Upregulate Thrombomodulin Expression in Monocytic Cells, Counteracting the Effects of Tumor Necrosis Factor and Oxidized LDL", Circulation, 102-2867-2872 (2000).

Ostrem, et al., "Induction of Monocytic Differentiation of HL-60 Cells by 1,25-Dihydroxyvitamin D analogs", Journal of Biological Chemistry, 262(29), 14164-14171 (1987).

Park, et al., "Intravenous Calcitriol Regresses Myocardial Hypertrophy in Hemodialysis PatientsWith Secondary HyperparathyroidismAmerican", Journal of Kidney Diseases, 33, 73-81 (1999).

Posner, et al., "New Vitamin D3 Derivatives with Unexpected Antiproliferative Activity: 1(Hydroxymethyl)-25-Hydroxyvitamin D3 Homologs", J Med Chem, 35, 3280-3287 (1992).

Prescott,__Methods__in__Cell__Biology__Academic__Press__NY,__ Vol__XIV,__33__et__seq__(1976).

Salusky, et al., "Cardiovascular calcification in end-stage renal disease", Nephrology Dialysis Transplantaiton, 17, 336-339 (2002).

Schwarz, et al., "Effect of 1,25(OH)2 Vitamin D3 on glomerulosclerosis in subtotally nephrectomized rats", Kidney Internat 53, 1696-1705 (1998).

Shevde, et al, "A potent analog of 1a,25-dihydroxyvitamin D3 selectively induces bone formation", PNAS USA, 99, 13487-13491 2002.

Shimizu, et al., "Synthesis and Biological activities of new 1a, 25-dihydroxy-19-norvitamin D3 analogs with modifications in both the A-ring and the side chain", Bioorganic and Medicinal Chemistry, 14, 4277-4294 (2006).

Shiraishi, et al., "The Advantage of Alfacalcidol Over Vitamin D in the Treatment of Osteoporosis," Calcified Tissue International, 65, 311-316 (1999).

Shiuey, et al., Total Synthesis of 1a-Fluoro-25-hydroxycholecalciferol and -ergocalciferol, J Org. Chem, 55, 423-247 (1990).

Sicinski, et al, "Synthesis and Biological Activity of 22-Iodo- and (E)-20(22)-Dehydro Analogues of 1a,25-Dihydroxyvitamin D3", Biooorganic and Medicinal Chemistry, 7, 2877-2889 91999).

Sicinski, et al, New 1a,25-Dihydroxy-19-norvitamin D3 Compounds of High Biological Activity: Synthesis and Biological Evaluation of 2-Hydroxymethyl, 2-Methyl, and 2-methylene analogues, J Med Chem, 41, 4662-4674 (1998).

Slatopolsky, "Effects of 19-Nor-1,25(OH)2D2, a New Analogue of Calcitriol, on Secondary Hyperparathyroidism in Uremic Rats", American Journal of Kidney Disease, 4, S40-S47 (1998).

Teng, et al., "Survival of Patients undergoing hemodialysis with paricalcitol or calcitriol therapy", N Engl J Med, 349, (5), 446-456 (2003).

Uchiyama, et al., "ED-71, a Vitamin D Analog, Is a More Potent Inhibitor of Bone Resorption Than Alfacalcidol in an Estrogen-deficient Rat Model of Osteoporosis" Bone, 4, 582-588 (2002).

Wu-Wong, et al., Effects of Vitamin D analogs on gene expression profiling in human coronary artery smooth muscle cells, Atherosclerosis, 186, 20-28 (2006).

Wu-Wong, et al., "Vitamin D receptor (VDR) localization in human promyelocytic leukemia cells", Leukemia Lymphoma, 47(4), 727-723 (2006).

Wu-Wong, et al., "Effects of vitamin d analogs on the expression of plasminogen activator inhibitor-1 in human vascular cells", Thrombosis Research, 118, 709-714 (2006).

Wu-Wong, et al., "The potential for vitamin D receptor activation in cardiovascular research", Thrombosis Research, 118, 709-714 (2006).

Sardina, et al, "Studies on the Synthesis of Side-Chain Hydroxylated Metabolites of Vitamin D. 2. Stereocontrolled Synthesis of 25-Hydroxyvitamin D21", J. Org. Chem, vol. 51, No. 8, 1986, pp. 1264-1269.

Bury, et al., "Molecular Evaluation of Vitamin D3 Receptor Agonists Designed for Topical Treatment of Skin Diseases1," The Journal of Investigative Dermatology, 116:5, (May 2001), pp. 785-792, XP002526323, pp. 785-792; Fig. 1; compound EB1213.

Jensen, et al., "Prediction of in vitro metabolic stability of calcitriol analogs by QSAR." Journal of Computer-Aided Molecular Design, 17, (2003) pp. 849-859, XP002526324; p. 858; table 8; compounds F, G.

Kutner, et al., "Vitamin D C-22 Aldehydes, New Key Intermediates for the Synthesis of Side Chain Modified Vitamin D Analogues," Tetrahedron Letters, 28:49, (1987), pp. 6129-6132, XP002526321, p. 6131, compound 9.

Ostrem, et al., "The vitamin D-induced differentiation of HL-60 cells: Structural requirements," Steroids, 49:1-3, (1987), pp. 73-102, XP002526322, p. 95; Fig. 10.

Perlman, et al., "Synthesis of novel 20-oxo-pregnacalciferol analogs with binding affinity to the progesterone receptor," Bioorg. & Med. Chem. Lett., 5:22, (1995), pp. 2695-2700, XP002526325; p. 2698.

Sicinski, et al., "New 1α,25-Dihydroxy-19-norvitamin D3 Compounds of High Biological Activity: Synthesis and Biological Evaluation of 2-Hydroxymethyl, 2-Methyl, and 2-Methylene Analogues," J. Med. Chem., 41:23, (1998), pp. 4662-4674, XP002526359, p. 4664; compounds 6A, 6B, 20.

PCT International Searching Authority and Invitation to Pay Additional Fees and, Where Applicable, Protest Fees, Mailed: Jul. 20, 2009.

Abbreviations: 1α,25(OH$_2$)D$_3$ for active vitamin D; RXR for retinoic acid receptor complex; VDR for vitamin D receptor; PKC for protein kinase C; VDREs for vitamin D response elements.

Compound Triage Flow Chart

Z: Zemplar, paricalcitol

Normal Mouse Calcemia Model

VITAMIN D RECEPTOR ACTIVATORS AND METHODS OF MAKING

CROSS REFERENCE TO RELATED APPLICATIONS

This application claims priority to U.S. Provisional Patent Application No. 60/989167, entitled "NEW VITAMIN D RECEPTOR ACTIVATORS AND METHODS OF MAKING" filed Nov. 20, 2007.

TECHNICAL FIELD

This application relates to novel Vitamin D compounds and methods of making these compounds. These novel compounds can be used as drugs to treat a variety of diseases, including, but not limited to, bone disorders, cardiovascular disease, hyperparathyroidism, immune disorders, proliferative disease, renal disease and thrombosis.

BACKGROUND OF THE INVENTION

The discovery that vitamin $D_3$ is a precursor to a functionally active hormone, 1,25-dihydroxyvitamin $D_3$, occurred more than 30 years ago. Subsequent studies have led to our current understanding that vitamin $D_3$ is made from 7-dehydrocholesterol in the skin after exposure to ultraviolet light, modified by vitamin $D_3$-25-hydroxylase in the liver, and then by 25-hydroxyvitamin $D_3$-1α-hydroxylase (CYP27B1) in the kidney to form the active hormone, 1,25-dihydroxyvitamin $D_3$ (calcitriol, commercially available under the brand name CALCIJEX from Abbott Laboratories, Abbott Park, Ill.). Calcitriol functions by binding to the Vitamin D receptor (hereinafter abbreviated as or used interchangeably with "VDR"), a nuclear receptor. The binding of calcitriol to the VDR activates the receptor to recruit cofactors to form a complex that binds to vitamin D response elements in the promoter region of target genes to regulate gene transcription. The vitamin D signaling pathway is summarized in FIG. 1.

During the past three decades, a majority of the studies in the VDR field have focused on elucidating calcitriol's biochemical role, e.g., in mineral homeostasis, which covers regulation of parathyroid hormone, intestinal calcium and phosphate absorption and bone metabolism. As shown in FIG. 2, 1α-hydroxylase (CYP27B1) in the kidney is responsible for production of the active metabolite 1α,25-dihydroxy vitamin $D_3$ (calcitriol) which subsequently binds to the VDR and ultimately exerts its physiological effects including modulation of intestinal calcium transport and calcium mobilization in the bone, regulation of parathyroid hormone (PTH) synthesis, and downregulation of CYP27B1 through a feedback mechanism. In turn, PTH stimulates CYP27B1, increases calcium resorption, and decreases phosphate resorption in the kidney. Through the coordinated functions of PTH and calcitriol, the homeostasis of calcium and phosphorous is maintained. Calcitriol is oxidized by CYP24 (24-hydroxylase) to metabolites that are excreted. VDR is found in more than 30 tissues and may have other effects beyond its function in controlling PTH and mineral homeostasis.

As a result of those studies, many new analogs of calcitriol have been developed, some having reduced hypercalcemic effect, and several analogs such as paricalcitol (commercially available under the brand name ZEMPLAR, from Abbott Laboratories, Abbott Park, Ill.) and doxercalciferol (commercially available under the brand name HECTOROL, from Genzyme, Cambridge, Mass.) are currently on the market for the treatment of hyperparathyroidism secondary to chronic kidney disease (CKD). In addition, a few VDR modulators are marketed for the treatment of psoriasis and osteoporosis.

In addition, since VDR is widely distributed in organs and tissues throughout the body, it is likely involved with numerous disease states. Results from numerous preclinical studies suggest that VDR modulators may be beneficial for treating various diseases including cardiovascular diseases (CVD), immune disorders, oncology-related thrombosis, etc.

In particular, several lines of evidence support the idea that VDR plays an important role in the regulation of cardiovascular physiology, the immune system and other biophysiological systems in humans. However, preclinical data have suggested that at least some Vitamin D Receptor activators (hereinafter abbreviated as or used interchangeably with "VDRAs") and/or vitamin D analogs, especially at higher doses, can cause hypercalcemia, which is linked to vascular calcification, myocardial infarction, heart failure, cardiomyopathy and cerebrovascular accidents. Therefore, the medical community does not endorse use of these compounds as a therapy for cardiovascular disease, but rather recommends only limited use.

Similarly, although some VDRAs and/or vitamin D analogs are currently used to treat psoriasis, an immune disorder, their usage is limited due to the concern about hypercalcemic side effects.

Recent data compares survival of patients with chronic renal disease undergoing hemodialysis and treated with either calcitriol or paricalcitol (Teng, M. et al. N. Engl. J. Med., 2003, 349, 446-456.). There was a significant survival benefit to those patients on paricalcitol compared to those on calcitriol. Although calcium and phosphorous levels had increased to a lesser degree in paricalcitol treated patients, the study does not differentiate whether or not the enhanced survival benefit of paricalcitol was due to improvement in mineral imbalance or effect of a specific vitamin D therapy. Additionally, the survival rate did not associate with vitamin D receptor activator dose and was independent of baseline serum calcium, phosphorous or parathyroid hormone levels, suggesting that the cause of lower morbidity may not be closely tied to these disease marker levels. In fact, the actual mechanism of the benefit has not been determined. However, since cardiovascular disease is the cause of death in the majority of dialysis patients, patient survival may be enhanced by paricalcitol's effects on the cardiovascular system.

Other studies (Salusky, I. B.; Goodman, W. G. Nephrology, Dialysis and Transplantation, 2002, 17, 336-339.) show that vitamin D receptor activator therapy may actually worsen survival rate in patients with chronic kidney disease as a result of side effects such as vascular calcification. This has led the medical community to limit usage of vitamin D receptor activator therapy.

An alternative therapy to vitamin D receptor activator therapy is provided by calcimimetics such as Cinacalcet (Sensipar®, Amgen). By contrast, Cinacalcet lowers parathyroid hormone levels by increasing the sensitivity of the calcium-sensing receptor of the parathyroid gland. There are, however, limitations to this therapeutic approach. Both hypersensitivity and severe hypocalcemia are noted contraindications. Dose titration is required to establish the optimal therapy. Several clinicians have suggested co-administration with a VDRA as an approach to treating secondary hyperparathyroidism.

Administration of pharmacological vitamin D receptor activator therapy conventionally involves titrating the dose to an effect, either correcting parathyroid hormone and/or serum calcium levels. Overdosing is monitored to prevent toxicities. It may therefore be advantageous to develop vitamin D receptor activators that have beneficial effects such as reduction of parathyroid hormone levels in chronic renal disease over a wide dosage range while having limited effect on increasing serum calcium levels, essentially increasing the therapeutic window. There also appears to be a survival benefit perhaps associated with improved cardiovascular health. Certainly, preclinical studies have shown a desirable improvement as indicated by cardiovascular markers. Improvements in these aspects of vitamin D receptor activator therapy present the opportunity to expand use of vitamin D receptor activator therapy.

Vitamin D derivatives are complex molecules and their synthesis can be challenging. For example, the synthesis of compounds with the unnatural 20S stereochemistry requires both a method for the epimerization of the C20 center (as designated with the vitamin D numbering system and shown on Formula (I)), as well as a method for the separation of the two resulting isomers, which is typically chromatography. Thus, mild conditions for the epimerization, and a chemical method for distinguishing between the isomers would assist the synthesis of these compounds.

Likewise, the reported synthesis of A-rings containing the 2-methylene moiety (see above regarding numbering) requires only six steps, but the overall yield is poor, and there are no crystalline intermediates to assist in purification.

In addition, the final coupling of the A-ring moiety to the C/D ring typically proceeds in poor yield; a better coupling protocol would make Vitamin D derivatives more available.

SUMMARY OF THE INVENTION

The invention is directed to vitamin D receptor activators, compositions comprising such compounds, processes for preparing such compounds, and intermediates obtained during such processes. One aspect of the invention relates to a compound of formula (I)

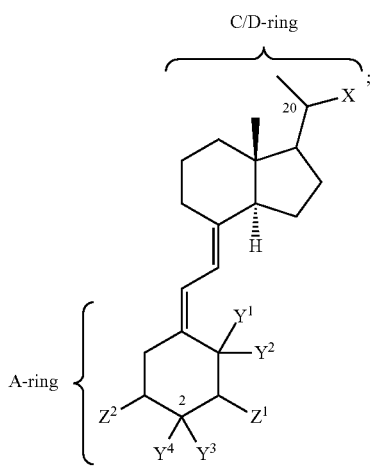

or a pharmaceutically acceptable salt or prodrug thereof, wherein
the carbon to which X is attached can have the R or S configuration;
X is —CH$_2$OR$^1$, —CH$_2$OC(O)R$^2$, —CR$^3$R$^4$—(CH$_2$)$_m$—CR$^5$R$^6$—CR$^7$(CH$_3$)$_2$, OR$^8$;
Y$^1$ and Y$^2$ are each hydrogen or taken together are a methylene group;

Y$^3$ and Y$^4$ are each hydrogen or taken together are a methylene group;
Z$^1$ is fluorine, hydroxy, or hydroxymethyl;
Z$^2$ is fluorine or hydroxy;
R$^1$ is hydrogen, alkyl, or aryl;
R$^2$ is alkyl, alkylamino, alkylcarbonyloxyalkyl, or hydroxyalkyl;
R$^3$ and R$^4$ are independently hydrogen or alkoxy with the proviso that both are not alkoxy;
R$^5$ and R$^6$ are independently hydrogen or alkyl;
R$^7$ is hydrogen, alkoxy or hydroxy;
R$^8$ is —CH$_2$CH$_2$C(CH$_3$)$_2$OH; and
m is 1, 2 or 3.

Another aspect of the invention relates to pharmaceutical compositions comprising compounds of the invention. Such compositions can be administered in accordance with a method of the invention, typically as part of a therapeutic regimen for treatment or prevention of conditions and disorders related to vitamin D receptor activity, particularly in mammals.

A further aspect of the invention relates to a method of selectively modulating vitamin D receptor activity. The method is useful for treating, preventing or both treating and preventing conditions and disorders related to vitamin D receptor activity in mammals. More particularly, the method is useful for conditions and disorders related to renal disease, secondary hyperparathyroidism associated with chronic kidney disease, osteoporosis, osteomalacia, osteodystrophy, thrombus formation, the renin-angiotensin system, myocardial hypertrophy, hypertension, autoimmune disorders, immunosuppression, transplant rejection, arthritis, multiple sclerosis, psoriasis, inflammatory bowel disease, type 1 diabetes, or systemic lupus erythematosus, cancers of the colon, prostate, breast, leukemia or Kaposi sarcoma.

The compounds, compositions comprising the compounds, methods for using the compounds, and processes for preparing the compounds, as well as intermediates obtained in such processes, are further described herein.

DETAILED DESCRIPTION OF THE INVENTION

Definition of Terms

Figure 1:
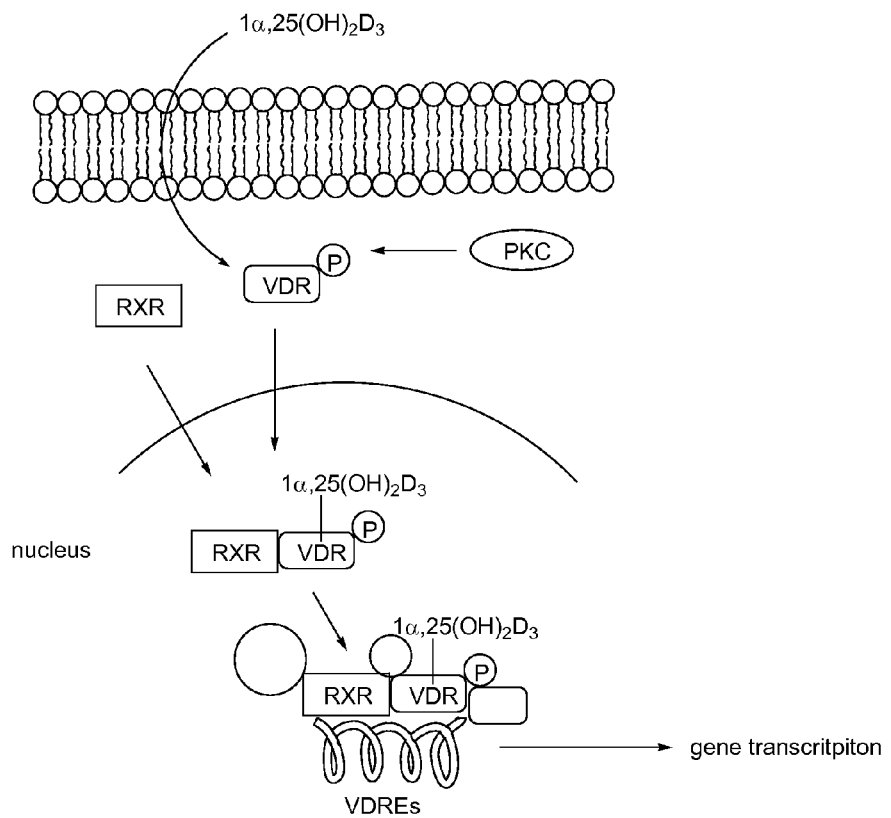
FIG. 1 schematically illustrates the Vitamin D signaling pathway in humans.
Figure 2:
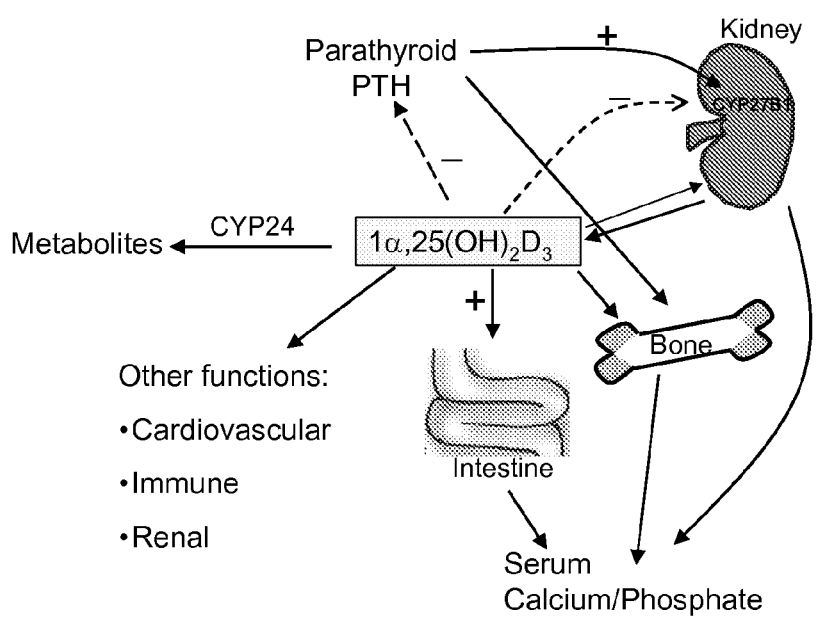
FIG. 2 schematically illustrates the role of Vitamin D in mineral homeostasis.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH═CH—, —CH═CH$_2$CH$_2$—, and —CH═C(CH$_3$)CH$_2$—.

The term "alkenyloxy" as used herein, means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein, means an alkyl group, as defined herein, appended to the parent molecular moiety through a —N(H)— group. Representative examples of alkylamino include, but are not limited to methylamino, cyclopropylamino, and t-butylamino.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylcarbonyloxyalkyl" as used herein, means an alkylcarbonyloxyl group, as defined herein, appended to the parent molecular moiety through an alkyl group, as defined herein. Representative examples of alkylcarbonyloxyalkyl include, but are not limited to, acetoxymethyl, acetoxyethyl, and pivaloxymethyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited to, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "alkynyloxy" as used herein, means an alkynyl group, as defined herein, appended to the parent molecular moiety through an oxygen atom. Representative examples of alkynyloxy include, but are not limited to, 2-propynyloxy and 2-butynyloxy.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylal kyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, mercapto, nitro, —NZ$^7$Z$^8$, and (NZ$^9$Z$^{10}$)carbonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylthiomethyl.

The term "azido" as used herein, means a —N$_3$ group.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —NZ$^7$Z$^8$, and (NZ$^9$Z$^{10}$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" as used herein, means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl, The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$^7$Z$^8$ and (NZ$^9$Z$^{10}$)carbonyl. Heteroaryl groups of the invention that are substituted with a hydroxyl group may be present as tautomers. The heteroaryl groups of the invention encompass all tautomers including non-aromatic tautomers.

The term "heteroarylalkoxy" as used herein, means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl )ethoxy, pyridin-3-ylmethoxy, 6-chloropyridin-3-ylmethoxy, pyridin-4-ylmethoxy, (6-(trifluoromethyl )pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl) methoxy, pyrimidin-5-ylmethoxy, 2-(pyrimidin-2-yl)propoxy, thien-2-ylmethoxy, and thien-3-ylmethoxy.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl )pyridin-3-yl)methyl, (6-(cyano)pyridin-3-yl )methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylalkylcarbonyl" as used herein, means a heteroarylalkyl, as defined herein, appended to the parent molecular moiety through a carbonyl group, as defined herein.

The term "heteroarylalkylthio" as used herein, means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl) methylthio, pyrimidin-5-ylmethylthio, 2-(pyrimidin-2-yl) propylthio, thien-2-ylmethylthio, and thien-3-ylmethylthio.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl )carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl) carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl) oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heteroarylthio" as used herein, means a heteroaryl group, as defined herein, appended to the parent molecular moiety through a sulfur atom. Representative examples of heteroarylthio include, but are not limited to, pyridin-3-ylthio and quinolin-3-ylthio.

The term "heteroarylthioalkyl" as used herein, means a heteroarylthio group, as defined herein, appended to the parent molecular moiety through an alkyl group, as defined herein. Representative examples of heteroarylthioalkyl include, but are not limited to, pyridin-3-ylthiomethyl, and 2-quinolin-3-ylthioethyl.

The term "heterocycle" or "heterocyclic" as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered rings contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —$NZ^7Z^8$ and $(NZ^9Z^{10})$carbonyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy.

The term "heterocyclealkyl" as used herein, means a heterocycle, as defined herein, appended to the parent molecular moiety through an alkyl group, as defined herein. Representative examples of heterocyclealkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl.

The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, piperidin-4-ylmethylcarbonyl, piperazin-1-ylmethylcarbonyl, 3-methyl-i-pyrrolidin-1-ylbutylcarbonyl, (1R)-3-methyl-1-pyrrolidin-1-ylbutylcarbonyl, (1S)-3-methyl-1-pyrrolidin-1-ylbutylcarbonyl.

The term "heterocyclealkylthio" as used herein, means a heterocyclealkyl group, as defined herein, appended to the parent molecular moiety through a sulfur atom. Representative examples of heterocyclealkylthio include, but are not limited to, 2-pyridin-3-ylethythio, 3-quinolin-3-ylpropythio, and 5-pyridin-4-ylpentylthio.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkyl group, as defined herein.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "heterocyclethio" as used herein, means a heterocycle group, as defined herein, appended to the parent molecular moiety through a sulfur atom. Representative examples of heterocyclethio include, but are not limited to, pyridin-3-ylthio and quinolin-3-ylthio.

The term "heterocyclethioalkyl" as used herein, means a heterocyclethio group, as defined herein, appended to the parent molecular moiety through an alkyl group, as defined herein. Representative examples of heterocyclethioalkyl include, but are not limited to, pyridin-3-ylthiomethyl, and 2-quinolin-3-ylthioethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, triethylsilyl, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl" as used herein, is a subset of alkenyl, as defined herein, and means an alkenyl group containing from 2 to 4 carbon atoms. Examples of lower alkenyl are ethenyl, propenyl, and butenyl.

The term "lower alkoxy" as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" as used herein, is a subset of alkyl as defined herein and means a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower alkylthio" as used herein, is a subset of alkylthio, means a lower alkyl group, as defined herein, appended to the parent molecular moiety through a sulfur atom. Representative examples of lower alkylthio include, but are not limited, methylthio, ethylthio, and tert-butylthio.

The term "lower alkynyl" as used herein, is a subset of alkynyl, as defined herein, and means an alkynyl group containing from 2 to 4 carbon atoms. Examples of lower alkynyl are ethynyl, propynyl, and butynyl.

The term "lower haloalkoxy" as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl" as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "NZ$^7$Z$^8$" as used herein, means two groups, Z$^7$ and Z$^8$, which are appended to the parent molecular moiety through a nitrogen atom. Z$^7$ and Z$^8$ are each independently selected from the group consisting of hydrogen, alkyl, alkylcarbonyl, alkoxycarbonyl, aryl, arylalkyl, formyl and (NZ$^{11}$Z$^{12}$)carbonyl. In certain instances within the invention, Z$^7$ and Z$^8$ taken together with the nitrogen atom to which they are attached form a heterocyclic ring. Representative examples of NZ$^7$Z$^8$ include, but are not limited to, amino, methylamino, acetylamino, acetylmethylamino, phenylamino, benzylamino, azetidinyl, pyrrolidinyl and piperidinyl.

The term "NZ$^9$Z$^{10}$" as used herein, means two groups, Z$^9$ and Z$^{10}$, which are appended to the parent molecular moiety through a nitrogen atom. Z$^9$ and Z$^{10}$ are each independently selected from the group consisting of hydrogen, alkyl, aryl and arylalkyl. Representative examples of NZ$^9$Z$^{10}$ include, but are not limited to, amino, methylamino, phenylamino and benzylamino.

The term "NZ$^{11}$Z$^{12}$" as used herein, means two groups, Z$^{11}$ and Z$^{12}$, which are appended to the parent molecular moiety through a nitrogen atom. Z$^{11}$ and Z$^{12}$ are each independently selected from the group consisting of hydrogen, alkyl, aryl and arylalkyl. Representative examples of NZ$^{11}$Z$^{12}$ include, but are not limited to, amino, methylamino, phenylamino and benzylamino.

The term "(NZ$^9$Z$^{10}$)carbonyl" as used herein, means a NZ$^9$Z$^{10}$ group, as defined herein, appended to the parent molecular moiety through a carbonyl group, as defined herein. Representative examples of (NZ$^9$Z$^{10}$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

The term "tautomer" as used herein means a proton shift from one atom of a compound to another atom of the same compound wherein two or more structurally distinct compounds are in equilibrium with each other.

Compounds Of The Invention

Compounds of the invention can have the formula (I) as described in the Summary of the Invention.

In one embodiment, the compounds of the invention can have the formula (I) wherein X is $CR^3R^4$—$(CH_2)_m$—$CR^5R^6$—$CR^7(CH_3)_2$; $Y^1$ and $Y^2$ are each hydrogen or taken together are a methylene group; $Y^3$ and $Y^4$ are each hydrogen or taken together are a methylene group; $Z^1$ is fluorine, hydroxy, or hydroxymethyl; $Z^2$ is fluorine or hydroxy; $R^3$ and $R^4$ are independently hydrogen or alkoxy; $R^5$ and $R^6$ are independently hydrogen or alkyl; $R^7$ is hydrogen, alkoxy or hydroxy; and m is 1 or 2.

In another embodiment, compounds of the invention can have the formula (I), wherein X is —$CH_2OC(O)R^2$; $Y^1$ and $Y^2$ are each hydrogen; $Y^3$ and $Y^4$ taken together are a methylene group; $Z^1$ is hydroxy; $Z^2$ is hydroxy; and $R^2$ is alkyl, alkylamino, alkylcarbonyloxyalkyl, or hydroxyalkyl.

In another embodiment, compounds of the invention can have the formula (I), wherein X is —$CH_2OR^1$; $Y^1$ and $Y^2$ are each hydrogen; $Y^3$ and $Y^4$ taken together are a methylene group; $Z^1$ is hydroxy; $Z^2$ is hydroxy; and $R^1$ is hydrogen, alkyl, or aryl.

In another embodiment, compounds of the invention can have the formula (I), wherein X is —$OR^8$; $Y^1$ and $Y^2$ are each hydrogen; $Y^3$ and $Y^4$ taken together are a methylene group; $Z^1$ is hydroxy; $Z^2$ is hydroxy; and $R^8$ is —$CH_2CH_2C(CH_3)_2OH$.

In another embodiment, compounds of the invention can have the formula (I), wherein X is —$OR^8$; $Y^1$ and $Y^2$ are each hydrogen; $Y^3$ and $Y^4$ taken together are a methylene group; $Z^1$ is hydroxymethyl; $Z^2$ is hydroxy; and $R^8$ is —$CH_2CH_2C(CH_3)_2OH$.

Specific embodiments contemplated as part of the invention include, but are not limited to compounds of formula (I), or salts or prodrugs thereof, for example:

(2S)-2-[(1R,3R,7E,17β)-1,3-dihydroxy-2-methylene-9,10-secoestra-5,7-dien-17-yl]propyl pivalate;

(1R,3R,7E,17β)-17-[(1S)-2-hydroxy-1-methylethyl]-2-methylene-9,10-secoestra-5,7-diene-1,3-diol;

(2R)-2-[(1R,3R,7E,17β)-1,3-dihydroxy-2-methylene-9,10-secoestra-5,7-dien-17-yl]propyl pivalate;

(2S)-2-[(1R,3R,7E,17β)-1,3-dihydroxy-2-methylene-9,10-secoestra-5,7-dien-17-yl]propyl 2,2-dimethylbutanoate;

(2S)-2-[(1R,3R,7E,17β)-1,3-dihydroxy-2-methylene-9,10-secoestra-5,7-dien-17-yl]propyl tert-butylcarbamate;

(2S)-2-[(1R,3R,7E,17β)-1,3-dihydroxy-2-methylene-9,10-secoestra-5,7-dien-17-yl]propyl 2-(acetyloxy)-2-methylpropanoate;

(1R,3R,7E)-2-methylene-17-[(1R,4S)-1,4,5-trimethylhexyl]-9,10-secoestra-5,7-diene-1,3-diol;

(1R,3R,7E,17β)-17-[(1S)-1-(3-hydroxy-3-methylbutoxy)ethyl]-2-methylene-9,10-secoestra-5,7-diene-1,3-diol;

(1R,3R,7E)-17-[(1R,4S)-1,4,5-trimethylhexyl]-9,10-secoestra-5,7-diene-1,3-diol;

(1S,3R,5Z,7E,24R)-22,25-dimethoxy-9,10-secoergosta-5,7,10-triene-1,3-diol;

(1R,3R,7E,17β)-17-[(1S,4R)-2,5-dimethoxy-1,4,5-trimethylhexyl]-9,10-secoestra-5,7-diene-1,3-diol;

(1R,3R,7E)-2-methylene-17-[(1S)-1-methyl-2-phenoxyethyl]-9,10-secoestra-5,7-diene-1,3-diol;

(1R,3S,5Z,7E,17β)-3-fluoro-17-[(1R)-5-hydroxy-1,5-dimethylhexyl]-2-methylene-9,10-secoestra-5,7-dien-1-ol;

(2S)-2-[(1R,3R,7E,17β)-1,3-dihydroxy-2-methylene-9,10-secoestra-5,7-dien-17-yl]propyl 2-hydroxy-2-methylpropanoate;

(1R,3R,7E,17β)-17-[(1R,4R)-5-hydroxy-1,4,5-trimethylhexyl]-9,10-secoestra-5,7-diene-1,3-diol;

(1R,3R,5E,7E,17β)-17-[(1R)-5-hydroxy-1,5-dimethylhexyl]-3-(hydroxymethyl)-2-methylene-9,10-secoestra-5,7-dien-1-ol;

(1R,3R,5E,7E, 17β)-3-(hydroxymethyl)-17-[(1S)-1-(3-hydroxy-3-methylbutoxy)ethyl]-2-methylene-9,10-secoestra-5,7-dien-1-ol; and (1R,3S,5E,7E,17β)-3-fluoro-17-[(1R)-5-hydroxy-1,5-dimethylhexyl]-2-methylene-9,10-secoestra-5,7-dien-1-ol.

Compounds of the invention may exist as stereoisomers wherein asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

In another embodiment of this invention, therefore, pertains to a process for making (1R,3aR,4S,7aR)-1-[(1R)-2-hydroxy-1-methylethyl]-7a-methyloctahydro-1H-inden-4-ol, comprising:

(a) reacting Vitamin D2 with ozone in methanol and pyridine at about −70° C. to provide (2S)-2-[(1R,3aR,7aR)-7a-methyl-4-oxooctahydro-1H-inden-1-yl]propanal;

(b) reacting (2S)-2-[(1R,3aR,7aR)-7a-methyl-4-oxooctahydro-1H-inden-1-yl]propanal with about 0.05 to 0.30 equivalents of a base selected from pyrrolidine or piperidine in a solvent selected from tert-butyl methyl ether, chloroform, dichloromethane, isopropyl acetate, ethyl acetate, toluene or methanol at or about ambient temperature under an inert atmosphere for about 10 to 24 hours; adding about an additional 0.1 equivalents of the base with continued mixing for about another 24 to 120 hours provided a mixture of (2R)-2-[(1R,3aR,7aR)-7a-methyl-4-oxooctahydro-1H-inden-1 -yl]propanal and (2S)-2-[(1R,3aR,7aR)-7a-methyl-4-oxooctahydro-1H-inden-1-yl]propanal in about a 1:1 to 2:1 ratio;

(c) reacting the mixture of (2R)-2-[(1R,3aR,7aR)-7a-methyl-4-oxooctahydro-1H-inden-1-yl]propanal and (2S)-2-[(1R,3aR,7aR)-7a-methyl-4-oxooctahydro-1H-inden-1-yl]propanal with sodium borohydride in a mixture of tert-butyl methyl ether or acetonitrile and a protic solvent selected from methanol, ethanol and n-propanol at about 0 to 15° C. followed by gradual warming to room temperature over a period of about 0.5 to 3 hours to provide a mixture of (1R,3aR,4S,7aR)-1-[(1R)-2-hydroxy-1-methylethyl]-7a-methyloctahydro-1H-inden-4-ol and (1R,3aR,4S,7aR)-1-[(1S)-2-hydroxy-1-methylethyl]-7a-methyloctahydro-1H-inden-4-ol in about a 1:1 to 2:1 ratio; The ratio of the (R)-isomer was enhanced by chromatographic purification; and (d) reacting the mixture of (1R,3aR,4S,7aR)-1-[(1R)-2-hydroxy-1-methylethyl]-7a-methyloctahydro-1H-inden-4-ol and (1R,3aR,4S,7aR)-1-[(1S)-2-hydroxy-1-methylethyl]-7a-methyloctahydro-1H-inden-4-ol with 1 to 3 molar equivalents of vinyl acetate and 15 to 300 weight percent of an enzyme selected from Lipase AK or Lipase PS in a solvent selected from tert-butyl methyl ether, acetonitrile, toluene, or isopropyl acetate at about 5 to 50° C. for about 4 to 7 hours and at 0 to 15° C. for about 2 to 15 hours to provide (1R,3aR,4S,7aR)-1-[(1R)-2-hydroxy-1-methylethyl]-7a-methyloctahydro-1H-inden-4-ol and the undesired isomer as an acetate which were chromatographically separated.

Another embodiment of this invention, therefore, pertains to a process for coupling an A-ring phosphine oxide of formula (II) to a C/D-ring ketone of formula (III), comprising:

(a) mixing an A-ring phosphine oxide of formula (II) with about 1.4 equivalents of a C/D-ring ketone of formula (III) in toluene and then evaporating the volatiles; this process is repeated a second time; wherein $Y^1$ and $Y^2$ are each hydrogen or taken together are a methylene group; $Y^3$ and $Y^4$ are each hydrogen or taken together are a methylene group; $Z^5$ is fluorine, —O-(hydroxy-protecting group) or —CH$_2$O-(hydroxy-protecting group); $Z^4$ is fluorine, or —O-(hydroxy-protecting group); $X^1$ is —CH$_2$OR$^1$, —CH$_2$OC(O)R$^2$, —CR$^3$R$^4$—(CH$_2$)$_m$—CR$^5$R$^6$—CR$^{7a}$(CH$_3$)$_2$, or OR$^{8a}$; $R^1$ is hydrogen, alkyl, or aryl; $R^2$ is alkyl, alkylamino, alkylcarbonyloxyalkyl, or hydroxyalkyl; $R^3$ and $R^4$ are independently hydrogen or alkoxy with the proviso that both are not alkoxy; $R^5$ and $R^6$ are independently hydrogen or alkyl; $R^{7a}$ is hydrogen, alkoxy, hydroxy or protected hydroxy; $R^{8a}$ is —CH$_2$CH$_2$C(CH$_3$)$_2$OH or —CH$_2$CH$_2$C(CH$_3$)$_2$OSi(CH$_3$)$_3$; and m is 1, 2 or 3.

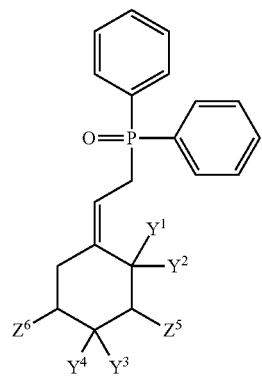

(II)

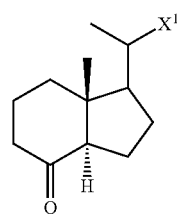

(III)

(b) dissolving the mixture of an A-ring phosphine oxide of formula (II) and C/D-ring ketone of formula (III) in tetrahydrofuran at about −80 to −65° C.;

(c) slowly adding a base such as lithium bis(trimethylsilyl)amide with continued stirring for 15 to 30 minutes followed by warming to about −10 to 10° C. and stirring for about another 15 to 30 minutes at that temperature to provide compounds of formula (IV).

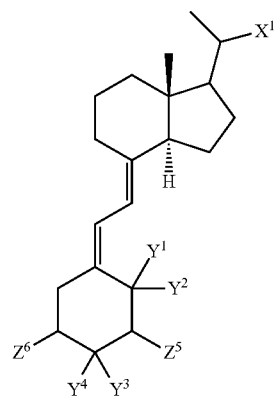

(IV)

Another embodiment of this invention, therefore, pertains to compounds of formula (V) useful for the preparation of compounds of formula (I), wherein $Y^{1a}$ and $Y^{2a}$ are each hydrogen; $Y^3$ and $Y^4$ are each hydrogen or taken together are a methylene group; $Z^3$ is fluorine, hydroxy, hydroxymethyl, —O-(hydroxy-protecting group) or —CH$_2$O-(hydroxy-protecting group); and $Z^4$ is fluorine, hydroxy, or —O-(hydroxy-protecting group). Preferred hydroxy-protecting groups are selected from tert-butyl(dimethyl)silyl and tert-butyl(diphenyl)silyl.

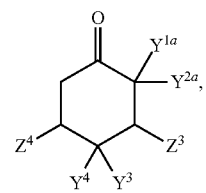

(V)

Specific embodiments contemplated as part of the invention include, but are not limited to compounds of formula (V), for example:

(3R,5R)-3-{[tert-butyl(dimethyl)silyl]oxy}-5-{[tert-butyl(diphenyl)silyl]oxy}-4-methylenecyclohexanone;

(3R,5R)-3-{[tert-butyl(dimethyl)silyl]oxy}-5-({[tert-butyl(dimethyl)silyl]oxy}methyl)-4-methylenecyclohexanone; or (3R,5R)-3,5-Bis{[tert-butyl(diphenyl)silyl]oxy}-4-methylenecyclohexanone Methods of the Invention Compounds and compositions of the invention are useful for modulating the effects of vitamin D receptors. In particular, the compounds and compositions of the invention can be used for treating or preventing disorders modulated by vitamin D receptors. Typically, such disorders can be ameliorated by selectively modulating the vitamin D receptor in a mammal, preferably by administering a compound or composition of the invention, either alone or in combination with another active agent, for example, as part of a therapeutic regimen.

In addition, the invention relates to method for treating or preventing conditions, disorders or deficits modulated by a vitamin D receptor, wherein the condition, disorder or deficit is selected from the group consisting of a bone disorders, cardiovascular disease, hyperparathyroidism, immune disorders, proliferative disease, renal disease and thrombosis comprising administration of a therapeutically suitable amount of a compound of formula (I),

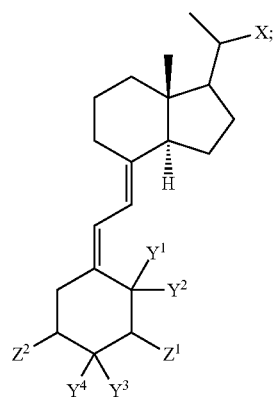

(I)

or a pharmaceutically acceptable salt or prodrug thereof, wherein the carbon to which X is attached can have the R or S configuration; X is —CH$_2$OR$^1$, —CH$_2$OC(O)R$^2$, —CR$^3$R$^4$—(CH$_2$)$_m$—CR$^5$R$^6$—CR$^7$(CH$_3$)$_2$, or OR$^8$; Y$^1$ and Y$^2$ are each hydrogen or taken together are a methylene group; Y$^3$ and Y$^4$ are each hydrogen or taken together are a methylene group; Z$^1$ is fluorine, hydroxy, or hydroxymethyl; Z$^2$ is fluorine or hydroxy; R$^1$ is hydrogen, alkyl, or aryl; R$^2$ is alkyl, alkylamino, alkylcarbonyloxyalkyl, or hydroxyalkyl; R$^3$ and R$^4$ are independently hydrogen or alkoxy with the proviso that both are not alkoxy; R$^5$ and R$^6$ are independently hydrogen or alkyl; R$^7$ is hydrogen, alkoxy or hydroxy; R$^8$ is —CH$_2$CH$_2$C(CH$_3$)$_2$OH; and m is 1, 2 or 3.

The invention also contemplates the method for treating or preventing a condition or disorder modulated by a vitamin D receptor comprising the step of administering a compound of formula (I), wherein the condition or disorder is selected from renal disease and secondary hyperparathyroidism associated with chronic kidney disease.

The invention also contemplates the method for treating or preventing a condition or disorder modulated by a vitamin D receptor comprising the step of administering a compound of formula (I), wherein the condition or disorder is selected from bone disorders associated with osteoporosis, osteomalacia, and osteodystrophy.

The invention also contemplates the method for treating or preventing a condition or disorder modulated by a vitamin D receptor comprising the step of administering a compound of formula (I), wherein the condition or disorder is selected from cardiovascular diseases associated with thrombus formation, the renin-angiotensin system, myocardial hypertrophy, and hypertension.

The invention also contemplates the method for treating or preventing a condition or disorder modulated by a vitamin D receptor comprising the step of administering a compound of formula (I), wherein the condition or disorder is selected from immune disorders associated with autoimmune disorders, immunosuppression, transplant rejection, arthritis, multiple sclerosis, psoriasis, inflammatory bowel disease, type 1 diabetes, and systemic lupus erythematosus.

The invention also contemplates the method for treating or preventing a condition or disorder modulated by a vitamin D receptor comprising the step of administering a compound of formula (I), wherein the condition or disorder is selected from cancers of the colon, prostate, breast, leukemia and Kaposi sarcoma.

Compounds for the method of the invention, including but not limited to those specified in the examples or otherwise specifically named, can modulate, and often possess an affinity for, vitamin D receptors. As vitamin D receptor activators, the compounds of the invention can be useful for the treatment or prevention of a number of vitamin D receptor-mediated diseases or conditions.

For example, vitamin D receptor activators have been shown to play a significant role in reducing parathyroid hormone levels (Hudson, J. Q. The Annals of Pharmacotherapy, 2006, 40, 1584-1593). As such, vitamin D receptor activators are suitable for the treatment of conditions and disorders related to chronic kidney disease. Some vitamin D receptor activators do not upregulate intestinal vitamin D receptors, thus limiting calcemic and hyperphosphatemic effects and the associated side effects (Slatopolsky, E.; Finch, J.; Ritter, C.; Takahashi, F. American Journal of Kidney Disease, 1998, 4, S40-S47). Studies have indicated that vitamin D receptor activator therapy reduces the progression of renal disease (Agarwal, R.; Acharya, M.; Tian, J.; Hippensteel, R. L.; Melnick, J. Z.; Qiu, P.; Williams, L.; Batlle, D. Kidney International, 2005, 68, 2823-2828 and Schwarz, U.; Amann, K.; Orth, S. R.; Simonaviciene, A.; Wessels, S.; Ritz, E. Kidney International, 1998, 53, 1696-1705).

In addition, vitamin D receptor activators have been shown to be involved in skeletal and mineral homeostatsis. These receptor activators are important for intestinal calcium absorption and subsequent anabolic activity on bone (Hendy, G. N.; Hruska, K. A.; Methew, S.; Goltzman, D. Kidney International, 2006, 69, 218-223). Certain agonists have shown the potential to selectively treat bone disorders with a lessened effect on parathyroid hormone suppression. (Shevde, N. K.; Plum, L. A.; Clagett-Dame, M.; Yamamoto, H.; Pike, J. W.; DeLuca, H. F. Proc. Natl. Acad. Sci. U.S.A. 2002, 99, 13487-13491; Uchiyama, Y.; Higuchi, Y.; Takeda, S.; Masaki, T.; Shira-Ishi, A.; Sato, K.; Kubodera, N.; Ikeda, K.; Ogata, E. Bone, 2002, 4, 582-588 and Shiraishi, A.; Higashi, S.; Ohkawa, H.; Kubodera, N.; Hirasawa, T.; Ezawa, I.; Ikeda, K.; Ogata, E. Calcified Tissue International, 1999, 65, 311-316).

Vitamin D receptor activators have been implicated in having affects on many aspects of the circulatory system. The vitamin D receptor system plays an important role in maintaining antithrombotic homeostasis (Aihara, K.; Azuma, H.; Akaike, M.; Ikeda, Y.; Yamashita, M.; Sudo, T.; Hayashi, H.; Yamada, Y.; Endoh, F.; Fujimura, M.; Yoshida, T.; Yamaguchi, H.; Hashizume, S.; Kato, M.; Yoshimura, K.; Yamamoto, Y.; Kato, S.; Matsumoto, T. J. Biol. Chem., 2004, 279, 35798-35802). Vitamin D receptor activators have been show to alter the expression and activity of proteins important for coagulation such as thrombomodulin, tissue factor, and plasminogen activator inhibitor 1 offering potential treatment in atherosclerotic diseases (Beer, T. M.; Venner, P. M.; Ryan, C. W.; Petrylak, D. P.; Chatta, G.; Ruether, J. D.; Chi, K. N.; Curd, J. G.; DeLoughery, T. G. British Journal of Haematology, 2006, 135, 392-394 and Ohsawa, M.; Koyama, T.; Yamamoto, K.; Hirosawa, S.; Kamei, S.; Kamiyama, R. Circulation, 2000, 102, 2867-2872). The renin-angiotensin II system is central in the regulation of blood pressure and elevated renin levels lead to hypertension, and cardiac hypertrophy. Vitamin D receptor activators directly suppress renin gene transcription in a vitamin D receptor-dependent mechanism offering a control mechanism for this system (Li, Y. C.; Qiao, G.; Uskokovic, M.; Xiang, W.; Zheng, W.; Kong, J. Journal of Steroid Biochemistry & Molecular Biology, 2004, 89-90, 397-392). Patients with chronic kidney disease receiving maintenance hemodialysis often suffer cardiovascular complications of which ischemic heart disease as a result of left ventricular hypertrophy is the most prominent. Hyperparathyroidism is a contributor and even partial control with a vitamin D receptor activator results in regression of myocardial hypertrophy without changes in other hemodynamic parameters (Park, C. W.; Oh, Y. S.; Shin, Y. S.; Kim, C. -M.; Kim, Y. -S.; Kim, S. Y.; Choi, E. J.; Chang, Y. S.; Bang, B. K. American Journal of Kidney Diseases, 1999, 33, 73-81).

The vitamin D receptor is expressed on most cell types of the immune system and in particular in modulating T cell responses. Currently vitamin D receptor activators are used topically to treat psoriasis. Animal models are suggestive that vitamin D receptor activators can be beneficial in the treatment of arthritis, autoimmune diabetes, experimental allergic encephalomyelitis, inflammatory bowel disease, or systemic lupus erythematosus suggesting the expansion of therapeutic utility in humans (Adorini, L. Cellular Immunology, 2005, 233, 115-124).

A number of signaling pathways involved with cancer are affected by vitamin D receptor activators. They are prominently, although with a great deal of heterogeneity, responsible for antiproliferative, anti-angiogenic, and pro-differentiation effects in a broad range of cancers mediated through both genomic and non-genomic mechanisms (Deeb, K. K.; Trump, D. L.; Johnson, C. S. Nature Reviews Cancer, 2007, 7, 684-700). The role of vitamin D metabolism seems to be important in the regulation of cell proliferation in the prostate (Lou, Y. -R.; Qiao, S.; Talonpoika, R.; Syvala, H.; Tuohimaa, P. Journal of Steroid Biochemistry and Molecular Biology, 2004, 92, 317-3250). There is an association of suppression of the autocrine growth factors IL-6 and IL-8 by vitamin D receptor activators and the development of Kaposi sarcoma (Masood, R.; Nagpal, S.; Zheng, T.; Cai, J.; Tulpule, A.; Smith, D. L.; Gill, P. S. Blood, 2000, 96, 3188-3194). Vitamin D analogs exert a differentiating effect on leukemia cells (James, S. Y.; Williams, M. A.; Newland, A. C.; Colston, K. W. Gen. Pharmac., 1999, 32, 143-154).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.01 µg to about 150 mg. More preferable doses can be in the range of from about 0.010 µg to about 10 mg. If desired, the effective daily dose can be divided into multiple doses for purposes of administration. Consequently, single dose compositions may contain such amounts or submultiples thereof to make up the daily dose.

Methods of Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: 9-BBN for 9-borabicyclo[3.3.1]nonane; BCA for bicinchoninic acid; BUN for blood urea nitrogen; CASMC for coronary artery smooth muscle cell; DAST for (diethylamino)sulfur trifluoride; DIBAL for diisobutylaluminum hydride; DMEM for Dulbecco modified Eagle's minimal essential medium; DTT for dithiothreitol; Et$_2$AlCl for diethylaluminum chloride; GC for gas chromatography; HOAC for acetic acid; HPLC for high-pressure liquid chromatography; LiHMDS for lithium bis(trimethylsilyl)amide; MsCl for methanesulfonyl chloride; NBT for nitroblue tetrazolium; nBuLi for n-butyllithium; Ncor1 for nuclear receptor co-repressor 1; PA % for peak area percent; PBS-T for phosphate buffered saline containing TWEEN 20; PCR for polymerase chain reaction; PMA for phorbol 12-myrystate 13-acetate; PPAR for peroxisome proliferator-activated receptor; PPTS for pyridinium p-toluenesulfonate; psi for pounds per square inch; PVDF for polyvinylidine fluoride; RPMI for Roswell Park Memorial Institute; SDS-PAGE for sodium dodecyl sulfate polyacrylamide gel electrophoresis; TBAF for tetra-n-butylammonium fluoride; TBDPS-Cl for t-butyldiphenylsilyl chloride; TBS-Cl for t-butyldimethylsilyl chloride; TBS-imidazole for t-butyldimethylsilyl imidazole; TBS-OTf for t-butyldimethylsilyl trifluoromethanesulfonate; TES-Cl for triethylsilyl chloride; TMP for 2,2,6,6-tetramethylpiperidine; Tris for trishydroxymethylaminomethane; TWEEN 20 for polyoxoethylenesorbitan monolaurate; VDR for vitamin D receptor; wt % for weight percent.

Compounds having Formula (I) may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary. Certain groups can be substituted as described within the scope of this invention as would be known to one skilled in the art. Representative procedures are shown in, but are not limited to, Schemes 1-7.

As outlined in Scheme 1, compounds of formula (1) wherein X is described herein can be oxidized with such agents as pyridinium chlorochromate on alumina or pyridinium dichromate with pyridinium p-toluenesulfonate in a solvent such as dichloromethane at a temperature from 0° C. to 30° C. over a period of 12 to 48 hours to furnish compounds of formula (2). Compounds of formula (2) may be reacted with anions of compounds of formula (3). The anions of formula (3) are prepared by reacting compounds of formula (3) with bases such as lithium bis(trimethylsilyl)amide or lithium diisopropylamide in a solvent such as tetrahydrofuran or dioxane over a temperature range of −78° C. to 0° C. in a period of 1-24 hours.

Scheme 1

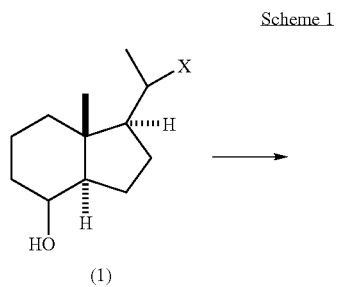
(1)

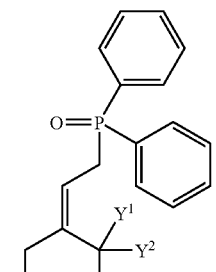
(2)

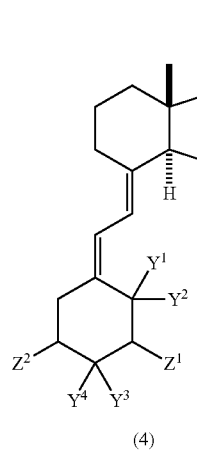
(3)
LiHMDS

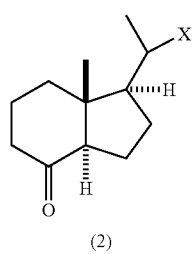
(4)

Scheme 2

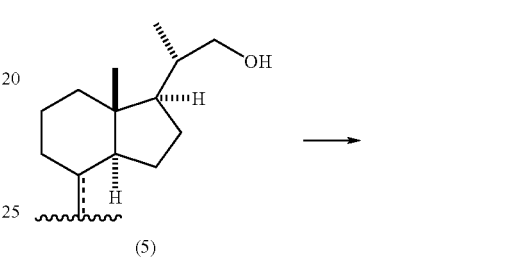
(5)

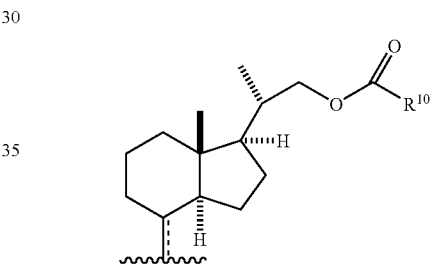
(6)

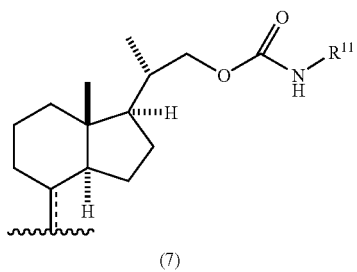
(7)

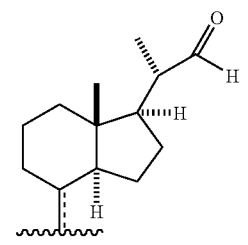
(8)

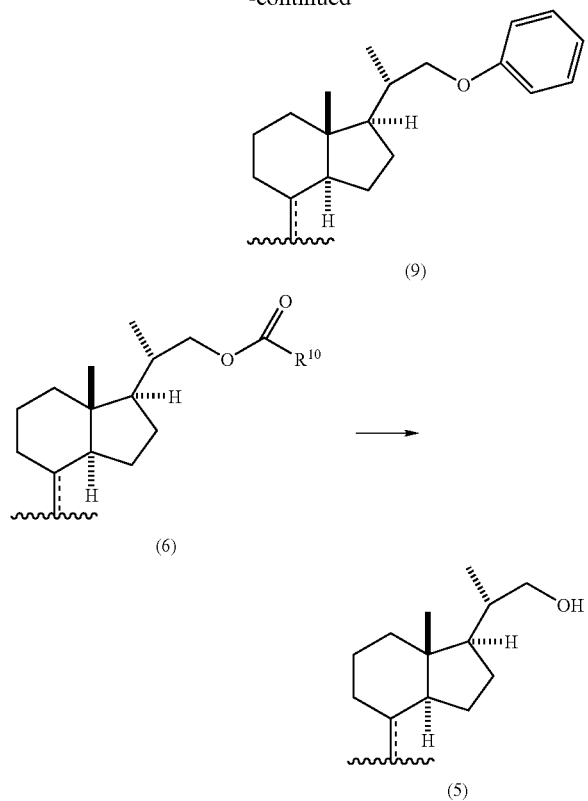

Compounds of formula (5) are representative of compounds (1), (2), and (4) shown in Scheme 1 wherein X is —CH₂OH and the functionality appended to the bottom of the C-ring ($\sim$) is either a hydroxyl group, a protected hydroxyl group, an oxo group, or the diene and A-ring exemplified by a compound of formula (4). A compound of formula (5) can be modified to furnish compounds with diverse functionality.

For example, compounds of formula (5) may be esterified by reacting with an acid chloride of formula $R^{10}C(O)Cl$, wherein $R^{10}$ is an alkyl group, in the presence of a base such as pyridine in a solvent like dichloromethane in a temperature range of 0° C. to 30° C. over a period of 6 to 48 hours to furnish esters of formula (6). Alternatively, compounds of formula (5) may be esterified by reacting with a carboxylic acid of formula $R^{10}CO_2H$, wherein $R^{10}$ is a hydroxylalkyl group, in the presence of triphenyl phosphine and di-tert-butylazodicarboxylate in a solvent such as toluene at a temperature range from 30 to 100° C. over a period of 1 to 24 hours.

Carbamates of formula (7) may be prepared from compounds of formula (5) by exposure to an isocyanate, $R^{11}NCO$ wherein $R^{11}$ is an alkyl group, in a mixture of solvents such as dimethylformamide and toluene at a temperature between 50 and 110° C. over 1 to 5 days.

Compounds of formula (5) may be oxidized to aldehydes of formula (8) with an oxidant such as tetra-n-propyl ammonium perruthenate and N-methylmorpholine oxide in the presence of 4 Å molecular sieves in a solvent such as dichloromethane over a period of 1 to 24 hours in a temperature range of 10 to 30° C.

Compounds of formula (5) may also be converted to ethers of formula (9) under Mitsunobu conditions. For example, compounds of formula (5) may be reacted with phenol in the presence of triphenylphosphine and di-tert-butylazodicarboxylate in a solvent such as toluene at a temperature range from 30 to 100° C. over a period of 0.5 to 24 hours.

Esters of formula (6) may at times serve as protecting groups for the hydroxy moiety of compounds of formula (5). Deprotection to expose the hydroxy group may be achieved by reduction with reagents such as lithium aluminum hydride in solvents such as ether or tetrahydrofuran at a temperature initially at approximately −78° C. for 5 to 30 minutes and then with gradual warming to 0 to 25° C. for 0.5 to 6 hours.

Scheme 3

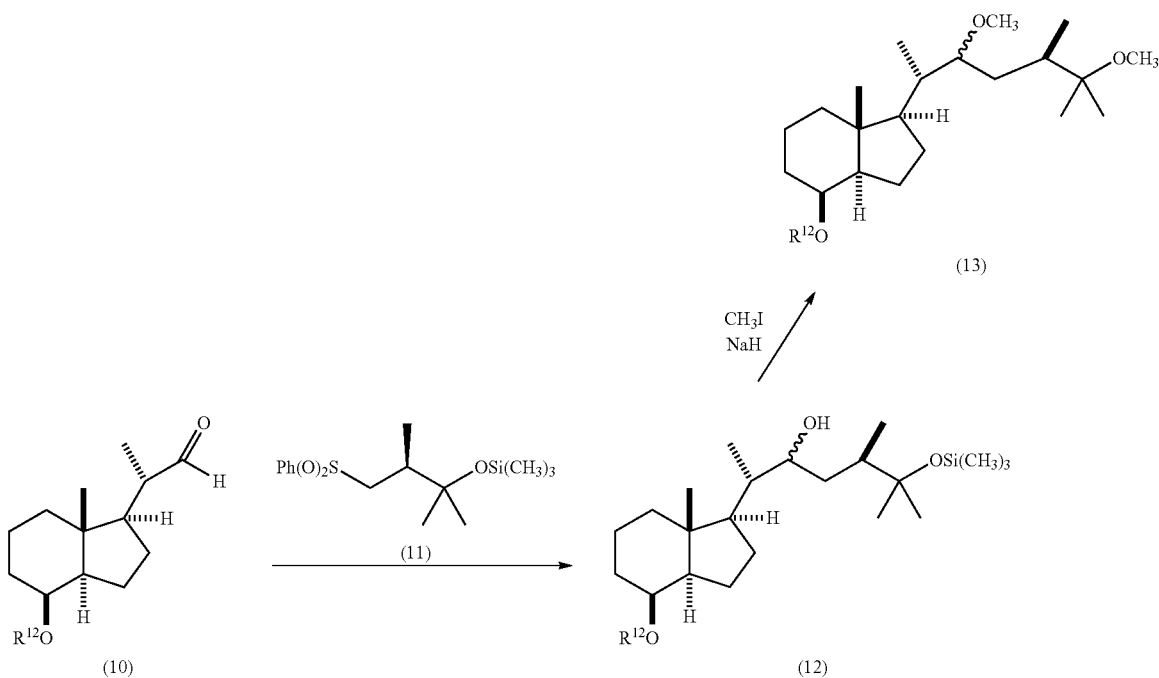

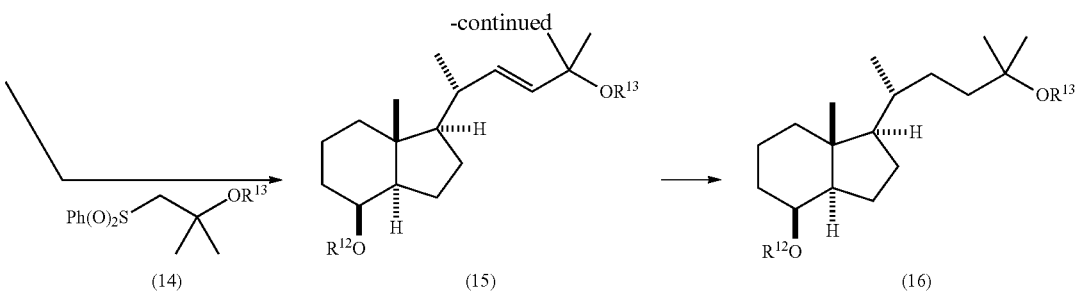

(14)  (15)  (16)

Aldehydes of formula (10), wherein $R^{12}$ is a silyl protecting group such as t-butyldimethylsilyl or t-butyldiphenylsilyl, can be reacted with sulfones of formulas (11) and (14) under conditions described in Kutner, A.; et al. Journal of Organic Chemistry 1988, 53, 3450-3457 to furnish compounds of formulas (12) and (15), respectively.

Compounds of formula (12) were then transformed to compounds of formula (13) by treatment with excess methyl iodide in the presence of sodium hydride in a solvent such as tetrahydrofuran at or near ambient temperature over a period of 6 to 48 hours.

Compounds of formula (15), wherein $R^{13}$ is either hydrogen or a trimethylsilyl group, are reduced with hydrogen in the presence of a catalyst such as platinum on carbon in a solvent such as acetic acid or in the presence of a catalyst such as palladium on carbon in a solvent such as ethyl acetate to furnish compounds of formula (16).

Scheme 4

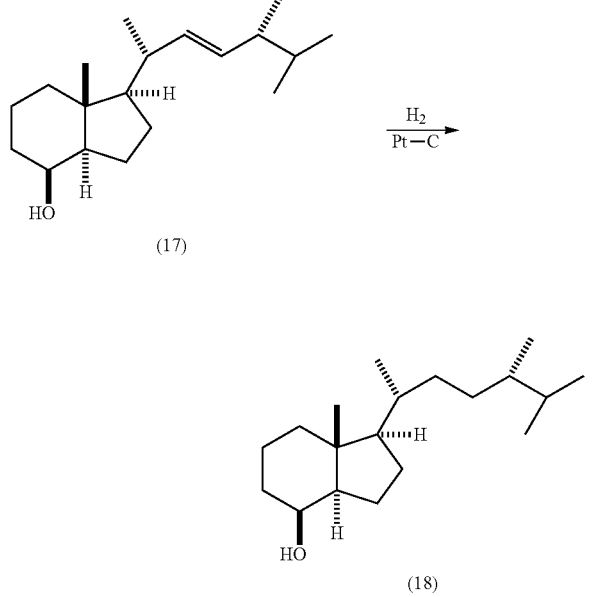

(17)

(18)

Compounds of formula (17) were reduced to compounds of formula (18) in the presence of hydrogen and a catalyst such as platinum on carbon in a solvent such as acetic acid.

Scheme 5

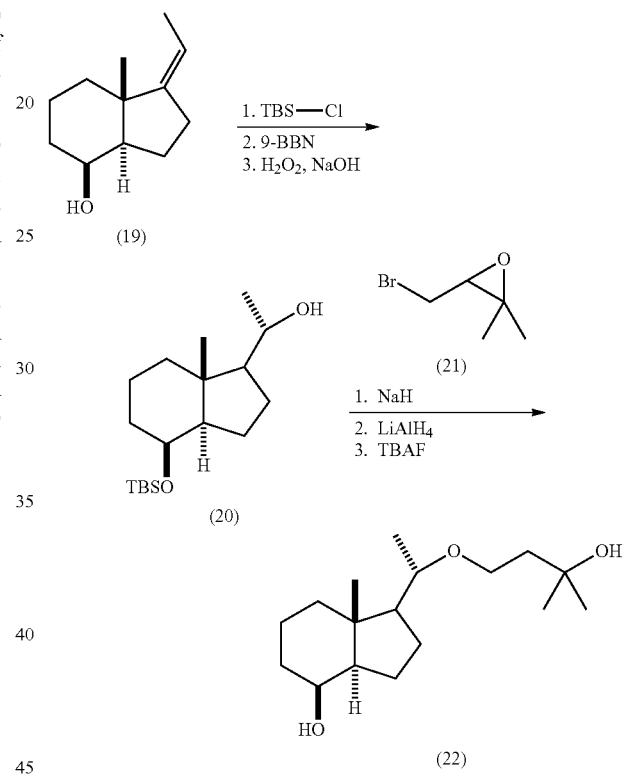

(19)

(20)

(21)

(22)

Compounds of formula (19) can be converted to compounds of formula (20) by passage through the following sequence. First the hydroxy moiety in compounds of formula (19) are protected as the corresponding t-butyldimethylsilyl ether by exposure to t-butyldimethylsilyl chloride in the presence of imidazole in solvent such as dimethylformamide initially at or near ambient temperature for approximately 4 hours and then at an increased temperature of 30 to 80° C. for an additional 8 to 48 hours. The alkene is then treated with 9-borabicyclo[3.3.1]nonane in a solvent such as tetrahydrofuran for 2 to 24 hours at a temperature from 35 to 60° C. Subsequent treatment at or near 0° C. with aqueous sodium hydroxide and peroxide provides compounds of formula (20).

Compounds of formula (20) are transformed to compounds of formula (22) through the following synthetic sequence. The hydroxy group of compounds of formula (20) is alkylated with compounds of formula (21) by treatment with a base such as sodium hydride in a solvent such as tetrahydrofuran at or near the reflux temperature for a period of 0.5 to 8 hours. Upon cooling to ambient temperature, treatment with lithium aluminum hydride over 2 to 16 hours stereoselectively opens the epoxide to the corresponding tertiary carbinol. The sequence to prepare compounds of formula (22) is completed by removal of the t-butyldimethylsilyl protecting group by exposure to tetra-n-butylammonium fluoride in tetrahydrofuran at a temperature between 60 and 80° C. for 8 to 24 hours.

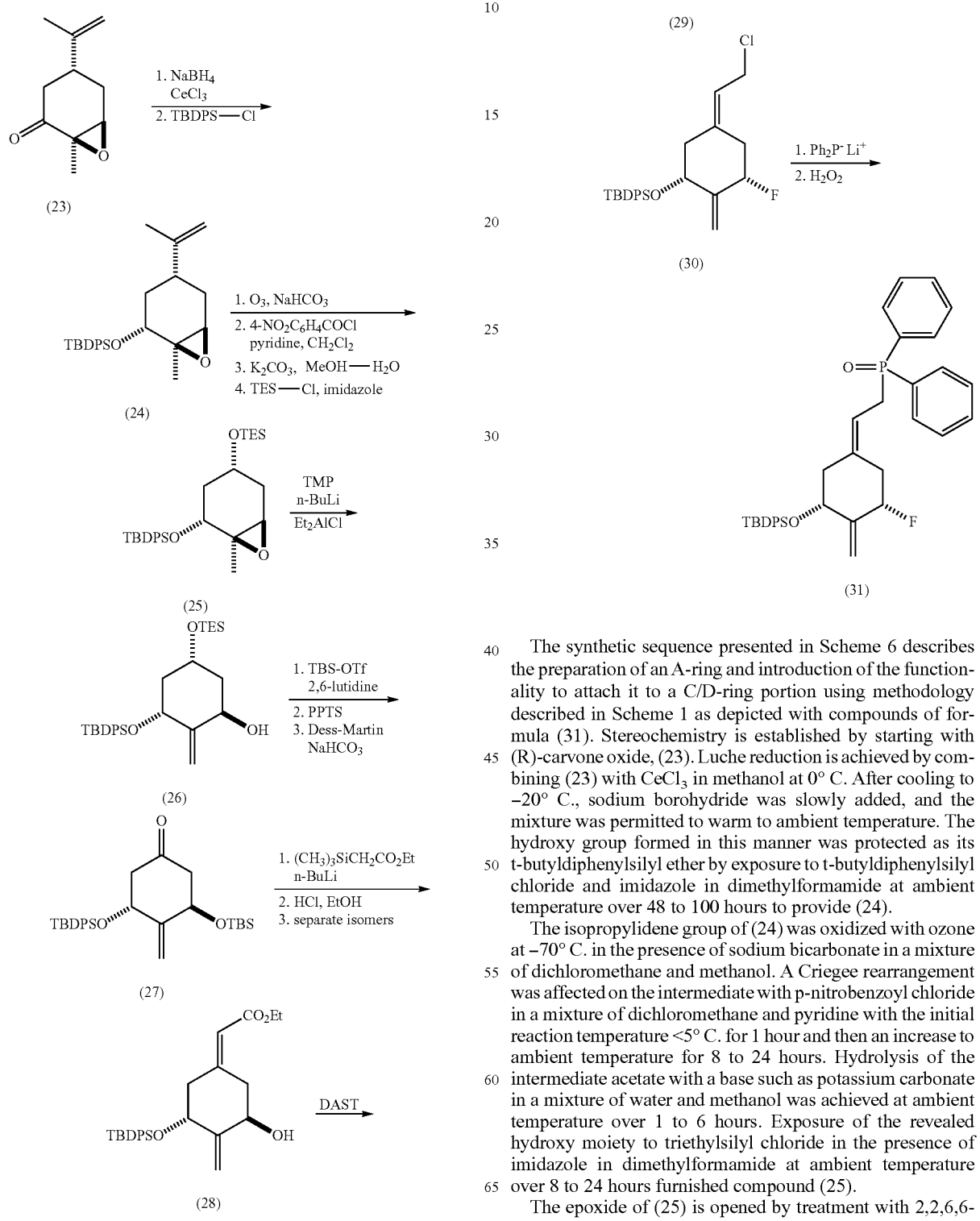

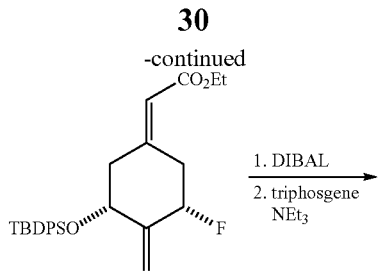

The synthetic sequence presented in Scheme 6 describes the preparation of an A-ring and introduction of the functionality to attach it to a C/D-ring portion using methodology described in Scheme 1 as depicted with compounds of formula (31). Stereochemistry is established by starting with (R)-carvone oxide, (23). Luche reduction is achieved by combining (23) with $CeCl_3$ in methanol at 0° C. After cooling to −20° C., sodium borohydride was slowly added, and the mixture was permitted to warm to ambient temperature. The hydroxy group formed in this manner was protected as its t-butyldiphenylsilyl ether by exposure to t-butyldiphenylsilyl chloride and imidazole in dimethylformamide at ambient temperature over 48 to 100 hours to provide (24).

The isopropylidene group of (24) was oxidized with ozone at −70° C. in the presence of sodium bicarbonate in a mixture of dichloromethane and methanol. A Criegee rearrangement was affected on the intermediate with p-nitrobenzoyl chloride in a mixture of dichloromethane and pyridine with the initial reaction temperature <5° C. for 1 hour and then an increase to ambient temperature for 8 to 24 hours. Hydrolysis of the intermediate acetate with a base such as potassium carbonate in a mixture of water and methanol was achieved at ambient temperature over 1 to 6 hours. Exposure of the revealed hydroxy moiety to triethylsilyl chloride in the presence of imidazole in dimethylformamide at ambient temperature over 8 to 24 hours furnished compound (25).

The epoxide of (25) is opened by treatment with 2,2,6,6-tetramethylpiperidine and n-butyllithium in the presence of diethylaluminum chloride in a solvent such as toluene at 0° C. with gradual warming over several hours to ambient temperature to give allylic alcohol (26).

Allylic alcohol (26) can be transformed to the corresponding t-butyldimethylsilyl ether by exposure to t-butyldimethylsilyl trifluoromethanesulfonate in the presence of a base such as 2,6-lutidine in a solvent such as dichloromethane at 0° C. Selective removal of the triethylsilyl protecting group is achieved by treatment with pyridinium p-toluenesulfonate in ethanol at ambient temperature over 1-5 hours. The revealed hydroxy group can then be oxidized to the corresponding ketone with Dess-Martin reagent (1,1,1-tris(acetyloxy)-1,1-dihydro-1,2-benziodoxol-3-(1H)-one in the presence of a base like sodium bicarbonate in a solvent such as dichloromethane at 0° C. supplying compound (27).

Ketone (27) can be converted to α,β-unsaturated ester (28) by reacting (27) with ethyl trimethylsilylacetate and n-butyllithium in a solvent such as tetrahydrofuran at −78° C. for 4 to 8 hours. The t-butyldimethylsilyl ether is selectively removed by treatment with concentrated hydrochloric acid in ethanol at ambient temperature for 8 to 24 hours to provide a mixture of alkenes which can be chromatographically separated to furnish (28).

The hydroxy group of (28) can be reacted with (diethylamino)sulfur trifluoride in dichloromethane at −78° C. for 20 to 120 minutes to supply the fluoride (29).

The α,β-unsaturated ester of (29) can be reduced with diisobutylaluminum hydride in a mixture of dichloromethane and toluene at −78° C. for 10 to 60 minutes to provide the corresponding allylic alcohol. Subsequent treatment with triphosgene in the presence of triethylamine at 0° C. for 30 to 60 minutes followed by gradual warming to ambient temperature over 1 to 3 hours to yield the allylic chloride (30).

Allylic chloride (30) can be treated with the lithium anion of diphenylphosphine in tetrahydrofuran at −60° C. for 1 to 4 hours. Oxidation to the corresponding diphenylphosphine oxide was achieved with either exposure to air or with aqueous hydrogen peroxide in dichloromethane at 0° C. over 0.5 to 3 hours to supply compound (31).

Scheme 7

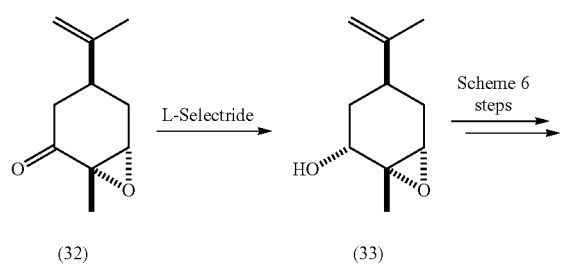

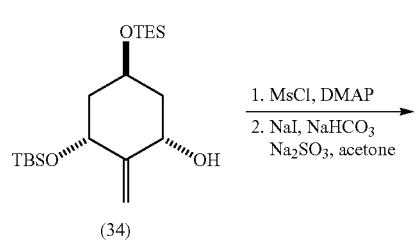

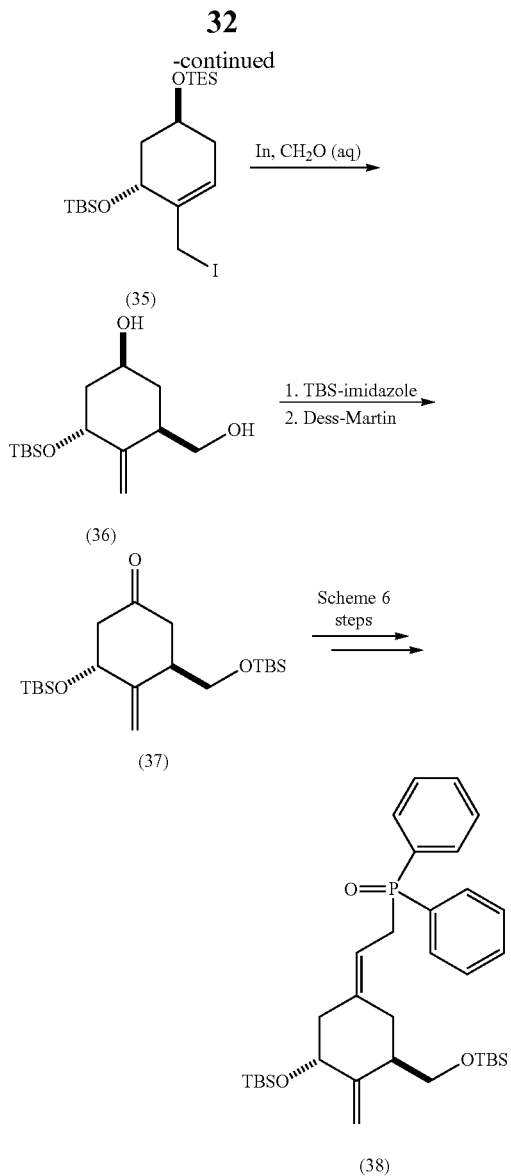

(S)-Carvone oxide (32) can be stereoselectively reduced with L-Selectride® at −78° C. over 5 to 12 hours in a solvent such as tetrahydrofuran to give the alcohol (33). This product can be transformed by the steps described in Scheme 6 to provide the allylic alcohol (34).

Allylic alcohol (34) can be converted to the corresponding mesylate by treatment with methanesulfonyl chloride in the presence of dimethylaminopyridine in dichloromethane at 0° C. for 3 to 8 hours. Subsequent treatment with sodium iodide in the presence of sodium bicarbonate and sodium sulfite in acetone gives the allylic iodide (35).

Compound (36) can be made from compound (35) by exposure to indium in the presence of formaldehyde in a mixture of tetrahydrofuran and water.

Selective protection of the primary hydroxy group of compound (36) can be achieved with treatment with t-butyldimethylsilyl imidazole in dichloromethane at ambient temperature for 24 to 48 hours. Oxidation of the secondary hydroxy group can then be carried out with an oxidant such as Dess-Martin reagent in a solvent such as dichloromethane at ambient temperature for 1 to 8 hours to obtain ketone (37).

Ketone (37) can be converted to diphenylphosphine oxide (38) by reaction sequences described in Scheme 6.

The compounds and processes of the present invention will be better understood in connection with the following Examples, which are intended as an illustration of and not a limitation upon the scope of the invention. Exemplary methods to synthesize these novel compounds according to the present invention are now described. Generally speaking, the examples demonstrate novel syntheses useful for making a wide variety of Vitamin D compounds, including the novel and inventive compounds according to the present invention. Thus, according to some embodiments of the present invention, fragments of desired Vitamin D compounds were made, fragments were modified additionally if desired and then eventually coupled to form the desired Vitamin D compounds.

EXAMPLES

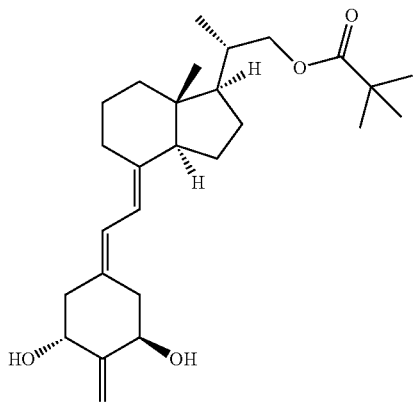 [SMILES: C=C1[C@H](O)CC(=C/C=C2\CCC[C@]3(C)[C@@H]([C@H](C)COC(=O)C(C)(C)C)CC[C@@H]23)C[C@H]1O]

Example 1

(2S)-2-[(1R,3R,7E, 17β)-1,3-dihydroxy-2-methylene-9,10-secoestra-5,7-dien-17-yl]propyl pivalate Example 1A

[2-((3R,5R)-3,5-bis{[tert-butyl(diphenyl)silyl]oxy}-4-methylenecyclohexylidene)ethyl](diphenyl)phosphine oxide The title compound was prepared through minor modification of the procedures described by DeLuca and Sicinski in WO98/41500.

Example 1 B (1R,3aR,4S,7aR)-1-[(1S)-2-hydroxy-1-methylethyl]-7a-methyloctahydro-1H-inden-4-ol The title compound was prepared from Vitamin D2 according to the procedures described by Sardina et al. in J. Org. Chem. 1986, 51(8), 1264-1269.

Example 1C (2S)-2-[(1R,3aR,4S,7aR)-4-hydroxy-7a-methyloctahydro-1H-inden-1-yl]propyl pivalate The compound of Example 1B (1.57 g, 6.7 mmol) was dissolved in 10 mL of dichloromethane and 5 mL of pyridine; the solution was cooled to 0° C., and 0.94 mL of pivaloyl chloride was added dropwise over 5 minutes. The resultant mixture was stirred at 0° C. for 4 hours, then it was warmed to ambient temperature overnight. The reaction was quenched with water, and the mixture was concentrated in vacuo with the bath maintained below ambient temperature. The crude material was partitioned between ether and 0.5 N aqueous HCl; the organic phase was washed with 0.5 N aqueous HCl, then brine, and dried over $Na_2SO_4$. The solvents were removed in vacuo; the residue was purified by chromatography on an Analogix Intelliflash 280™, eluting with a gradient of 10% to 20% ethyl acetate in hexanes to supply the titled compound (1.25 g, 63%).

Example 1D (2S)-2-[(1R,3aR,7aR)-7a-methyl-4-oxooctahydro-1H-inden-1-yl]propyl pivalate The compound of Example 1C (1.1 g, 3.7 mmol) was dissolved in 5 mL of dichloromethane and cooled to 0° C.; 4.1 g of pyridinium dichromate was added, followed by 30 mg of pyridinium p-toluenesulfonate. The resultant mixture was stirred for 8 hours at 0° C.; an additional 1.8 g of pyridinium dichromate and 20 mg of pyridinium p-toluenesulfonate were added, and the mixture was allowed to warm to ambient temperature overnight. The mixture was diluted with ether and filtered through a pad of diatomaceous earth with an ether wash. The filtrate was washed with 1 N aqueous HCl, and then filtered through a plug of silica gel. The crude product was purified by chromatography on an Analogix Intelliflash 280™, eluting with a gradient of 10% to 15% ethyl acetate in hexanes to furnish the titled compound (1.0 g, 94%).

Example 1E (2S)-2-[(1R,3R,7E,17β)-1,3-dihydroxy-2-methylene-9,10-secoestra-5,7-dien-17-yl]propyl pivalate Note: The following sequence was performed in a darkened hood. The compound of Example 1A (64 mg, 0.077 mmol) was combined with the compound of Example 1D (32 mg, 0.11 mmol), and the resultant mixture was dried by azeotroping twice with 1 mL of toluene. Tetrahydrofuran (2 mL) was added, and the solution was cooled to −78° C. A solution of lithium bis(trimethylsilyl)amide (0.6M in tetrahydrofuran; 0.40 mL) was added dropwise in two portions, producing a yellow-orange color that fades over 20 minutes. The solution was warmed to 0° C. and stirred at this temperature for 20 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was purified by chromatography on an Analogix Intelliflash 280™, eluting with a gradient from 0% to 6% ethyl acetate in hexanes. The product (61 mg) was dissolved in 2 mL of 1 N tetra-n-butylammonium fluoride in tetrahydrofuran; 0.25 mL of acetic acid was added, and the mixture was warmed to 70° C. overnight. The reaction mixture was partitioned between ethyl acetate and water. The organic phase was washed with brine and dried over $Na_2SO_4$. The solvents were removed in vacuo, and the residue was purified by chromatography on an Analogix IntelliFlash 280™, eluting with a gradient from 25% to 40% ethyl acetate in hexanes to supply the titled compound (21 mg). $^1$H NMR (500 MHz, $CD_2Cl_2$) δ ppm 6.33 (d, J=11.0 Hz, 1 H) 5.90 (d, J=11.3 Hz, 1 H) 5.06 (d, J=5.8 Hz, 2 H) 4.35-4.50 (m, 2 H)

4.04 (dd, J=10.7, 3.4 Hz, 1 H) 3.79 (dd, J=10.7, 7.0 Hz, 1 H) 2.82 (s, 1 H) 2.76 (dd, J=13.1, 4.3 Hz, 1 H) 2.55 (dd, J=13.1, 4.0 Hz, 1 H) 2.40-2.50 (m, 1 H) 2.01 (dd, J=12.4, 3.8 Hz, 2 H) 1.90 (s,1 H) 1.65-1.78 (m, 4 H) 1.32-1.40 (m, 4 H) 1.24-1.33 (m, 1 H) 1.23-1.34 (m, 3 H) 1.13-1.23 (m, 9 H) 0.96-1.06 (m, 3 H) 0.58 (s, 3 H); MS (+DCI) m/z 448 (M+NH$_4$)$^+$.

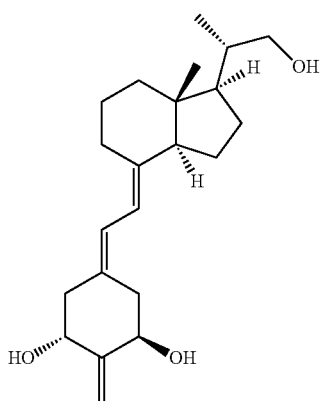 [SMILES: C=C1[C@H](O)CC(=C/C=C2\CCC[C@]3(C)[C@@H]([C@H](C)CO)CC[C@@H]23)C[C@H]1O]

Example 2

(1R,3R,7E,17β)-17-[(1S)-2-hydroxy-1-methylethyl]-2-methylene-9,10-secoestra-5,7-diene-1,3-diol Example 2A (2S)-2-((1R,3R,7E, 17β)-1,3-bis{[tert-butyl(diphenyl)silyl]oxy}-2-methylene-9,10-secoestra-5,7-dien-17-yl)propyl pivalate Note: The following sequence was performed in a darkened hood. The compound of Example 1A (64 mg, 0.077 mmol) was combined with the compound of Example 1D (32 mg, 0.11 mmol), and the resultant mixture was dried by azeotroping twice with 1 mL of toluene. Tetrahydrofuran (2 mL) was added, and the solution was cooled to −78 ° C. A solution of lithium bis(trimethylsilyl)amide (0.6 M in tetrahydrofuran; 0.40 mL) was added dropwise in two portions, producing a yellow-orange color that fades over 20 minutes. The solution was warmed to 0° C. and stirred at this temperature for 20 minutes. The reaction was quenched by addition of 1 mL of 1 N aqueous NH$_4$Cl, and the mixture was extracted with ethyl acetate. The organic extract was washed with brine and dried over Na$_2$SO$_4$. The solvents were removed in vacuo, and the residue was purified by chromatography on an Analogix Intelliflash 280™, eluting with a gradient from 0% to 6% ethyl acetate in hexanes.

Example 2B (1R,3R,7E,17β)-17-[(1S)-2-hydroxy-1-methylethyl]-2-methylene-9,10-secoestra-5,7-diene-1,3-diol Note: The following sequence was performed in a darkened hood. The compound of Example 2A (70 mg, 0.77 mmol) was dissolved in 1.5 mL of ether and cooled to −78° C. A solution of lithium aluminum hydride in tetrahydrofuran (1.0 M, 0.62 mL) was added; the mixture was stirred for 10 minutes, then it was warmed to 0° C. for 50 minutes. The reaction was quenched by cautious addition of ethyl acetate, followed by a solution of Rochelle's salt. After stirring for 15 minutes, the mixture was extracted with ethyl acetate; the organic extract was washed with brine and dried over Na$_2$SO$_4$. The solvents were removed in vacuo. A sample of this material (19 mg) was combined with 1.5 mL of 1 N tetra-n-butylammonium fluoride in tetrahydrofuran and 0.2 mL of acetic acid, and heated at 70° C. overnight. The reaction mixture was partitioned between ethyl acetate and water. The organic phase was washed with brine and dried over Na$_2$SO$_4$. The solvents were removed in vacuo, and the residue was purified by chromatography on an Analogix Intelliflash 280™, eluting with a gradient from 50% to 66% ethyl acetate in hexanes. Product containing fractions were combined and concentrated in vacuo to supply the titled compound (4 mg). $^1$H NMR (400 MHz, CD$_2$Cl$_2$) δ ppm 6.31 (d, J=11.2 Hz, 1H), 5.88 (d, J=11.2 Hz, 1H), 5.03-5.06 (m, 2H), 4.37-4.45 (m, 2H), 3.60 (dd, J=10.4, 3.2 Hz,1H), 3.33 (dd, J=10.4, 6.8 Hz, 1H), 2.78-2.87 (m, 1H), 2.74 (dd, J=13.2, 4.3 Hz, 1H), 2.53 (dd, J=13.2, 4.1 Hz, 1H), 2.24-2.32 (m, 2H), 1.96-2.06 (m, 2H), 1.78-1.94 (m, 2H), 1.60-1.74 (m, 3H), 1.44-1.60 (m, 4H), 1.28-1.40 (m, 4H), 1.03 (d, J=6.5 Hz, 3H), 0.56 (s, 3H); MS (+DCI) m/z 364 (M+NH$_4$)$^+$.

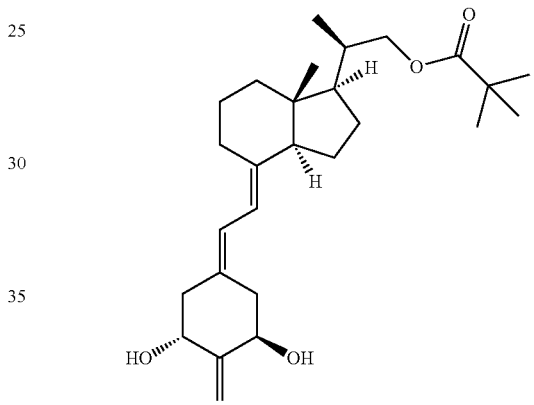

Example 3

(2R)-2-[(1R,3R,7E,17β)-1,3-dihydroxy-2-methylene-9,10-secoestra-5,7-dien-17-yl]propyl pivalate Example 3A (2S)-2-[(1R,3aR,7aR)-7a-methyl-4-oxooctahydro-1H-inden-1-yl]propanal Vitamin D$_2$ (30.04 g, 75.7 mmol) was dissolved in 1050 mL of methanol (35 mL/g) and 10.5 mL of pyridine (1% of methanol). The resulting solution, purged with nitrogen, was cooled to −70° C. Some of the vitamin D$_2$ precipitated from solution upon cooling. Ozone was bubbled through the cold, well-stirred slurry, which gradually became a solution, until the blue color of excess ozone persisted in the methanol solution. The excess ozone was purged from solution with a nitrogen stream. Trimethyl phosphite (77 mL, 652.8 mmol) was added over the course of 13 minutes with the temperature climbing from −75.1 to −69.5° C. The cooling bath was removed and the reaction was warmed to room temperature (1.5 hours). GC weight/weight analysis of the reaction mixture showed 71.9% keto-aldehyde, Example 3A. The solvent was removed by distillation on the rotary evaporator to give 98.03 g of a thick oil. The oil was transferred to a separatory funnel using 500 mL of saturated brine and 500 mL of tert-butyl methyl ether. After separation of the layers the aqueous layer was extracted with an additional 2×500 mL of tert-butyl methyl ether. The combined organic extracts were dried over sodium sulfate and concentrated to give 50.20 g of oil. GC analysis showed 75.13% of the titled keto-aldehyde and five impurities ranging from 1.27 to 4.97% (disregarding the trimethyl phosphate). The oil was dissolved in 500 mL of methanol and stripped down on the rotary evaporator. The process was repeated with another 500 mL of methanol, 300 mL of n-butanol, and 500 mL of methanol to give 57.04 g of oil. This material was dissolved in 500 mL tert-butyl methyl ether and washed with 3×100 mL of saturated, aqueous sodium bicarbonate. The aqueous washes were combined and back-extracted with 200 mL of tert-butyl methyl ether. An emulsion at the interface was extracted with ethyl acetate. The organic solutions were dried over sodium sulfate and concentrated to give 24.40 g of crude titled keto-aldehyde from the tert-butyl methyl ether and 1.53 g of crude titled keto-aldehyde from the ethyl acetate. $^1$H NMR showed that they were of comparable purity, so they were combined and used without further purification for the epimerization described in the next step. GC showed approximately 4 PA % trimethylphosphate remaining in the crude keto-aldehyde. $^1$H NMR (400 MHz, CDCl$_3$) δ 0.69 (s, 3H, 18-H$_3$),1.17 (d, J=6.86 Hz, 3H, 21-H$_3$), 2.47 (dd, J=7.41, 11.66 Hz,1H, 14-H), 9.60 (d, J=2.88 Hz, 1H, 22-H); $^{13}$C NMR (100 MHz, CDCl$_3$) δ13.18 (CH$_3$), 13.80 (CH$_3$),19.82 (CH$_2$), 24.18 (CH$_2$), 26.70 (CH$_2$), 38.82 (CH$_2$), 41.11 (CH$_2$), 49.26, 50.13 (C-13), 51.60, 61.10, 203.35 (C-22), 210.35 (C-8); GC: (Column: RTX-5,1.5 µm, 30 m×0.53 mm ID; Inlet 110° C., Detector 250° C.; Oven program: 100 to 250° C.@6° C./minute, then to 275° C.@10° C./minute and hold 5 minute@275° C.; Column 10 psi head pressure@40° C.; split flow of 36 mL/minute purge 10 mL/minute) Retention time for keto-aldehyde Example 3A:~16.5 minutes.

Example 3B (2R)-2-[(1R,3aR,7aR)-7a-methyl-4-oxooctahydro-1H-inden-1-yl]propanal (3B) and (2S)-2-[(1R,3aR,7aR)-7a-methyl-4-oxooctahydro-1H-inden-1-yl]propanal (3A)

The crude keto-aldehyde (Example 3A, 25.93 g, 75.73 mmol theoretical) was dissolved in 155 mL of tert-butyl methyl ether and put under a nitrogen atmosphere. Pyrrolidine (0.65 mL, 7.9 mmol) was added, and the solution was stirred at room temperature and monitored by GC. After 15.5 hours the epimer ratio was 0.3:1 (3B:3A). Another 0.65 mL of pyrrolidine was added. After another 24 hours the epimer ratio was 1.3:1. Twenty four hours later the epimer ratio was 1.79:1. The solution was stirred for an additional 72 hours. At that point the epimer ratio was 1.86:1. The reaction was carried directly to the reduction. $^1$H NMR (400 MHz, CDCl$_3$) δ 0.64 (s, 3H, 18-H$_3$), 1.08 (d, J=6.86 Hz, 3H, 21-H$_3$), 2.49 (dd, J=6.79, 11.73 Hz,1H, 14-H), 9.56 (d, J=4.80 Hz,1H, 22-H); GC: (Column: RTX-5, 1.5µm, 30 m×0.53 mm ID; Inlet 110° C., Detector 250° C.; Oven program: 100 to 250° C.@6° C./minute, then to 275° C.@10° C./minute and hold 5 minutes@275° C.; Column 10 psi head pressure@40° C.; split flow of 36 mL/minute purge 10 mL/minute) Retention time for epimeric keto-aldehyde (3B):~15.9 minutes.

Example 3C (1R,3aR,4S,7aR)-1-[(1R)-2-hydroxy-1-methylethyl]-7a-methyloctahydro-1H-inden-4-ol (3C') and (1R,3aR,4S,7aR)-1-[(1S)-2-hydroxy-1-methylethyl]-7a-methyloctahydro-1H-inden-4-ol (3C")

The tert-butyl methyl ether solution of keto-aldehyde epimers (75.73 mmol theoretical) from the epimerization reaction above (155 mL tert-butyl methyl ether) was cooled in an ice bath, then diluted with 225 mL of methanol. The solution was maintained at 0° C. under a nitrogen atmosphere. Sodium borohydride (10.3 g, 272.6 mmol) was added in portions to the reaction solution. After the addition, the cooling bath was removed, allowing the reaction to warm to room temperature. Once it had reached room temperature (one hour) the reaction was cooled back to 0° C. Over a 10 minute period 160 mL of 1N HCl was added and the reaction was warmed to room temperature. The solvent was removed under vacuum on the rotary evaporator. The residue was partitioned between 100 mL of saturated brine and 200 mL of ethyl acetate. The pH was adjusted to 2 using 1N HCl. The layers were separated and the aqueous layer was extracted with another 2×100 mL of ethyl acetate. The organic layers were combined and washed with saturated brine and dried over sodium sulfate. The solution was concentrated on the rotary evaporator, then chased with methylene chloride. The residue was pumped down using a vacuum pump to give 16.6 g of oil. $^1$H NMR of a sample showed the epimer ratio to be 1.84:1 (3C':3C"). The diol mixture was chromatographed on two 330 g Biotage 65M™ columns eluting with an ethyl acetate:hexane gradient.

First fraction: 7.06 g containing 93.73 PA % diol 3C', 2.65 PA % diol 3C", and 1.67% (1S,3aR,4S,7aR)-1-[(1S)-1-hydroxyethyl]-7a-methyloctahydro-1H-inden-4-ol.

Second fraction: 4.66 g containing 21.31 PA % diol 3C', 77.22 PA % diol 3C", and 1.47% of an unknown.

Diol 3C': $^1$H NMR (400 MHz, CDCl$_3$) δ 0.96 (s, 3H, 18-H$_3$), 0.96 (d, J=6.72 Hz, 3H, 21-H$_3$), 3.45 (dd, J=6.86, 10.57 Hz, 1H, 22-H), 3.71 (dd, J=3.57, 10.70 Hz, 1H, 22-H), 4.08 (bd q, J=2.70 Hz, 1H, 8-H); $^{13}$C NMR (100 MHz, CDCl$_3$) δ14.24 (CH$_2$), 16.90 (CH$_2$), 17.76, 22.64, 26.84, 33.80, 37.65 (CH$_2$), 40.00, 41.85 (C-13), 52.64 (CH$_2$), 53.00 (CH$_2$), 66.75 (C-8), 69.27 (C-22); GC: (Column: RTX-5, 1.5 µm, 30 m×0.53 mm ID; Inlet 110° C., Detector 250° C.; Oven program: 100 to 250° C.@6° C./minute, then to 275° C.@10° C./minute and hold 5 minutes. 275° C.; Column 10 psi head pressure@40° C.; split flow of 36 mL/minute purge 10 mL/minute) Retention time for diol 3C':~17.3 minutes.

Example 3D (1R,3aR,4S,7aR)-1-[(1R)-2-hydroxy-1-methylethyl]-7a-methyloctahydro-1H-inden-4-ol A diol mixture from the above step (Example 3C':3C", 1.86:1 12.2 g, potency: 93% combined both epimers), vinyl acetate (14.8 g, 3 equivalents) and Lipase AK (lot#56-678-AS, 3.0 g, 25 wt %, Amano Enzyme USA, Elgin, Ill.) in tert-butyl methyl ether (40 mL, 32.8 mL/g diol) were mixed at 9° C. for 6.5 hours then at 6° C. for 15.5 hours.

Ratio of unnatural diol (3D)/unnatural acetate/natural acetate by NMR: 62.1%/2.5%/35.4%. By GC: 59.2%/2.7%/36.9%.

Potency of crude: 53.97% of unnatural diol.

39.24% of natural acetate plus unnatural acetate.

This mixture was purified on a Biotage 65M™ column. The isolated unnatural diol was then recrystallized with hexane-tert-butyl methyl ether (95:5) to yield the titled compound (6.395 g, 67.6%).

Example 3E (2R)-2-[(1R,3aR,4S,7aR)-4-hydroxy-7a-methyloctahydro-1H-inden-1-yl]propyl pivalate The compound of Example 3D (0.58 g, 2.7 mmol) was dissolved in 4 mL of dichloromethane and 2 mL of pyridine; the solution was cooled to 0° C., and 0.39 mL of pivaloyl chloride was added dropwise over 5 minutes. The resultant mixture was stirred at 0° C. for 2.5 hours, then it was quenched with water, and the mixture was concentrated in vacuo with the bath maintained below ambient temperature. The crude material was partitioned between ether and 0.5 N aqueous HCl; the organic phase was washed with 0.5 N aqueous HCl, then brine, and dried over $Na_2SO_4$. The solvents were removed in vacuo; the residue (0.96 g) was carried forward without further purification.

Example 3F (2R)-2-[(1R,3aR,7aR)-7a-methyl-4-oxooctahydro-1H-inden-1-yl]propyl pivalate The crude compound of Example 3E (0.96 g) was dissolved in 19 mL of dichloromethane and cooled to 0° C.; 3.1 g of pyridinium dichromate was added, followed by 22 mg of pyridinium p-toluenesulfonate. The resultant mixture was stirred for 1.5 hours at 0° C.; an additional 1.3 g of pyridinium dichromate and 20 mg of pyridinium p-toluenesulfonate were added, and the mixture was allowed to warm to ambient temperature overnight. The mixture was diluted with ether and filtered through a pad of diatomaceous earth with an ether wash. The filtrate was washed with 1 N aqueous HCl, and then filtered through a plug of silica gel. The crude product was purified by chromatography on an Analogix IntelliFlash 280™, eluting with a gradient of 8% to 15% ethyl acetate in hexanes. Fractions containing the titled compound were combined and concentrated in vacuo (0.77 g, 96%, 2 steps).

Example 3G (2R)-2-[(1R,3R,7E,17β)-1,3-dihydroxy-2-methylene-9,10-secoestra-5,7-dien-17-yl]propyl pivalate Note: The following sequence was performed in a darkened hood. The compound of Example 1A (30 mg, 0.036 mmol) was combined with the compound of Example 3F (23 mg, 0.08 mmol), and the resultant mixture was dried by azeotroping twice with 1 mL of toluene. Tetrahydrofuran (2 mL) was added, and the solution was cooled to −78° C. A solution of lithium bis(trimethylsilyl)amide (1 M in tetrahydrofuran; 0.33 mL) was added dropwise in three portions, producing a yellow-orange color that fades over 30 minutes. The solution was warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was purified by chromatography on an Analogix Intelliflash 280™, eluting with a gradient from 0% to 4% ethyl acetate in hexanes. The product (22 mg) was dissolved in 1.5 mL of 1 N tetra-n-butylammonium fluoride in tetrahydrofuran; 0.2 mL of acetic acid were added, and the mixture was warmed to 70° C. overnight. The reaction mixture was partitioned between ethyl acetate and water. The organic phase was washed with brine and dried over $Na_2SO_4$. The solvents were removed in vacuo, and the residue was purified by chromatography on an Analogix IntelliFlash 280™, eluting with a gradient from 10% to 38% ethyl acetate in hexanes. Product containing fractions were combined and concentrated in vacuo to supply the titled compound (5.7 mg). $^1$H NMR (500 MHz, $CD_2Cl_2$) δ ppm 6.33 (d, J=11.2 Hz, 1H), 5.89 (d, J=11.2 Hz, 1H), 5.04-5.07 (m, 2H), 4.38-4.48 (m, 2H), 4.15 (dd, J=10.7, 3.5 Hz, 1H), 3.82 (dd, J=10.8, 6.7 Hz, 1H), 2.80-2.85 (m, 1H), 2.77 (dd, J=13.1, 4.5 Hz, 1H), 2.52-2.57 (m, 1H), 2.24-2.32 (m, 2H), 2.02-2.08 (m, 1H), 1.88-1.97 (m, 1H), 1.83-1.87 (m, 1H), 1.74-1.81 (m, 1H), 1.64-1.73 (m, 4H), 1.58-1.64 (m, 1H), 1.47-1.56 (m, 3H), 1.28-1.41 (m, 3H), 1.19 (s, 9H), 0.96 (d, J=6.6 Hz, 3H), 0.59 (s, 3H); MS (+ESI) m/z 448 $(M+NH_4)^+$.

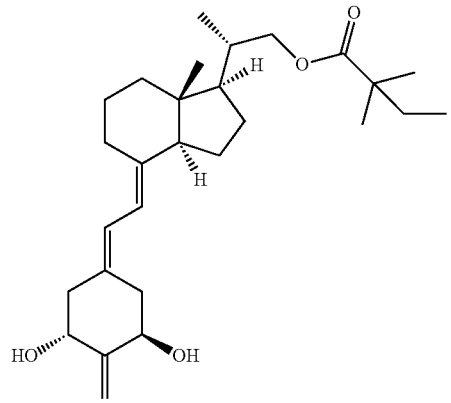 [SMILES: C=C1[C@H](O)CC(=C/C=C2\CCC[C@]3(C)[C@@H]([C@H](C)COC(=O)C(C)(C)CC)CC[C@@H]23)C[C@H]1O]

Example 4

(2S)-2-[(1R,3R,7E,17β)-1,3-dihydroxy-2-methylene-9,10-secoestra-5,7-dien-17-yl]propyl 2,2-dimethylbutanoate Example 4A (2S)-2-((1R,3R,7E,17β)-1,3-bis{[tert-butyl(diphenyl)silyl]oxy}-2-methylene-9,10-secoestra-5,7-dien-17-yl)propan-1-ol Note: The following sequence was performed in a darkened hood. The compound of Example 2A (70 mg, 0.77 mmol) was dissolved in 1.5 mL of ether and cooled to −78° C. A solution of lithium aluminum hydride in tetrahydrofuran (1.0 M, 0.62 mL) was added; the mixture was stirred for 10 minutes, and then warmed to 0° C. for 50 minutes. The reaction was quenched by cautious addition of ethyl acetate, followed by a solution of Rochelle's salt. After stirring for 15 minutes, the mixture was extracted with ethyl acetate; the organic extract was washed with brine and dried over $Na_2SO_4$. The solvents were removed in vacuo providing the titled compound (74 mg).

Example 4B (2S)-2-[(1R,3R,7E,17β)-1,3-dihydroxy-2-methylene-9,10-secoestra-5,7-dien-17-yl]propyl 2,2-dimethylbutanoate Note: The following sequence was performed in a darkened hood. The compound of Example 4A (29 mg, 0.03 mmol) was dissolved in 2.5 mL of 1,2-dichloroethane; triethylamine (120 μL) was added, and the solution was cooled to 0° C. 2,2-Dimethylbutyryl chloride (90 mg) was added, followed by a catalytic quantity of 4-dimethylaminopyridine, and the mixture was warmed slowly to ambient temperature. After 2 hours, the solvents were removed in vacuo, and the residue was partitioned between, ethyl acetate and 1 N aqueous HCl. The organic extract was washed with brine and dried over $Na_2SO_4$. The solvents were removed in vacuo, and the residue was purified by chromatography on an Analogix Intelliflash 280™, eluting with a gradient from 0% to 6% ethyl acetate in hexanes. The product (34 mg) was dissolved in 1.5 mL of 1 N tetra-n-butylammonium fluoride in tetrahydrofuran; 0.2 mL of acetic acid were added, and the mixture was warmed to 70° C. overnight. The reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 30% to 45% ethyl acetate in hexanes. Fractions containing the titled compound were combined and concentrated in vacuo (4.7 mg). $^1$H NMR (500 MHz, $CD_2Cl_2$) δ ppm 6.33 (d, J=11.2 Hz,1H), 5.90 (d, J=11.2 Hz, 1H), 5.05-5.07 (m, 2H), 4.38-4.48 (m, 2H), 4.04 (dd, J=10.6, 3.2 Hz, 1H), 3.79 (dd, J=10.7, 6.9 Hz,1H), 2.80-2.86 (m, 1H), 2.76 (dd, J=13.2, 4.5 Hz,1H), 2.55 (dd, J=13.3, 4.0 Hz,1H), 2.25-2.33 (m, 2H), 1.98-2.08 (m, 2H), 1.83-1.96 (m, 1H), 1.63-1.77 (m, 5H), 1.51-1.63 (m, 2H), 1.56 (q, J=7.5 Hz, 2H), 1.31-1.48 (m, 4H), 1.14 (s, 6H), 1.04 (d, J=6.6 Hz, 3H), 0.84 (t, J=7.5 Hz, 3H), 0.58 (s, 3H); MS (+DCI) m/z 462 $(M+NH_4)^+$.

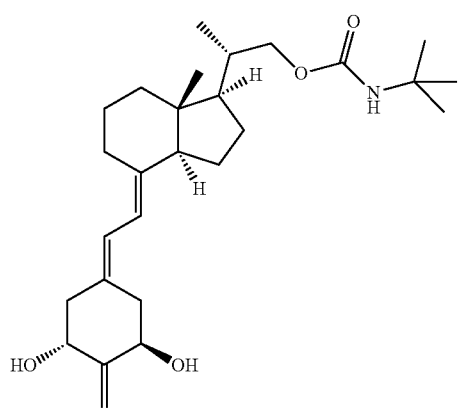 [SMILES: C=C1[C@H](O)CC(=C/C=C2\CCC[C@]3(C)[C@@H]([C@H](C)COC(=O)NC(C)(C)C)CC[C@@H]23)C[C@H]1O]

Example 5

(2S)-2-[(1R,3R,7E,17β)-1,3-dihydroxy-2-methylene-9,10-secoestra-5,7-dien-17-yl]propyl tert-butylcarbamate Note: The following sequence was performed in a darkened hood. The compound of Example 4A (20 mg, 0.02 mmol) was dissolved in 1 mL of 1:1 toluene:dimethylformamide; tert-butyl isocyanate (0.2 mL) was added in three portions over a period of three days, while the mixture is heated at 100-105° C. The solvents were removed in vacuo, and the residue was purified by chromatography on an Analogix Intelliflash 280™, eluting with a gradient of 0% to 20% ethyl acetate in hexanes. This material was dissolved in 1.5 mL of 1 N tetra-n-butylammonium fluoride in tetrahydrofuran, 0.2 mL of acetic acid were added, and the mixture was warmed overnight at 70° C. The reaction mixture was partitioned between 3:2 ethyl acetate/hexanes and water. The organic phase was washed with brine and dried over $Na_2SO_4$. The solvents were removed in vacuo, and the residue was purified by chromatography on an Analogix Intelliflash 280™, eluting with a gradient from 25% to 45% ethyl acetate in hexanes. Product containing fractions were combined and concentrated in vacuo to supply the titled compound (1.7 mg). $^1$H NMR (500 MHz, $CD_2Cl_2$) δ ppm 6.33 (d, J=11.3 Hz, 1 H) 5.89 (d, J=11.3 Hz, 1 H) 5.06 (d, J=6.4 Hz, 2 H) 4.66 (s, 1 H) 4.34-4.49 (m, 2 H) 3.95-4.06 (m, 1 H) 3.63-3.77 (m, 1 H) 2.70-2.91 (m, 2 H) 2.55 (dd, J=13.4, 4.0 Hz, 2 H) 2.20-2.38 (m, 5 H) 1.94-2.05 (m, 2 H) 1.83-1.96 (m, 2 H) 1.52-1.62 (m, 2 H) 1.33-1.47 (m, 4 H) 1.26-1.33 (m, 9 H) 0.98-1.06 (m, 3 H) 0.57 (s, 3 H).

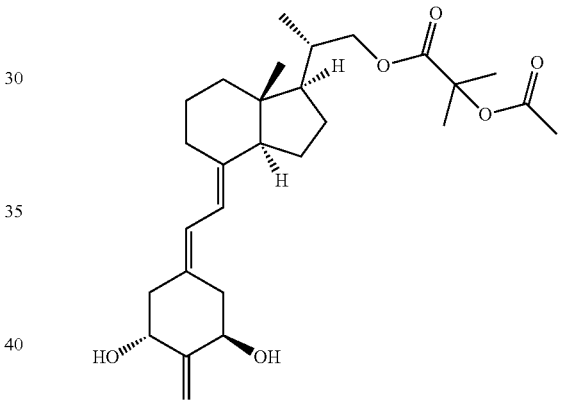

Example 6

(2S)-2-[(1R,3R,7E,17β)-1,3-dihydroxy-2-methylene-9,10-secoestra-5,7-dien-17-yl]propyl 2-(acetyloxy)-2-methyl propanoate

Example 6A

[2-((3R,5R)-3,5-bis{[tert-butyl(dimethyl)silyl]oxy}-4-methylenecyclohexylidene)ethyl](diphenyl)phosphine oxide The title compound was prepared using the procedures described by DeLuca and Sicinski in WO98/41500.

Example 6B (2S)-2-((1R,3R,7E,17β)-1,3-bis{[tert-butyl(dimethyl)silyl]oxy}-2-methylene-9,10-secoestra-5,7-dien-17-yl)propyl pivalate Note: The following sequence was performed in a darkened hood. The compound of Example 6A (64 mg, 0.077 mmol) was combined with the compound of Example 1D (32 mg, 0.11 mmol), and the resultant mixture was dried by azeotroping twice with 1 mL of toluene. Tetrahydrofuran (2 mL) was added, and the solution was cooled to −78° C. A solution of lithium bis(trimethylsilyl)amide (0.6 M in tetrahydrofuran; 0.40 mL) was added dropwise in two portions, producing a yellow-orange color that fades over 20 minutes. The solution was warmed to 0° C. and stirred at this temperature for 20 minutes. The reaction was quenched by addition of 1 mL of 1 N aqueous NH$_4$Cl, and the mixture was extracted with ethyl acetate. The organic extract was washed with brine and dried over Na$_2$SO$_4$. The solvents were removed in vacuo, and the residue was purified by chromatography on an Analogix Intelliflash 280™, eluting with a gradient from 0% to 6% ethyl acetate in hexanes.

Example 6C (2S)-2-((1R,3R,7E,17β)-1,3-bis{[tert-butyl(dimethyl)silyl]oxy}-2-methylene-9,10-secoestra-5,7-dien-17-yl)propan-1-ol Note: The following sequence was performed in a darkened hood. The compound of Example 6B (70 mg, 0.77 mmol) was dissolved in 1.5 mL of ether and cooled to −78° C. A solution of lithium aluminum hydride in tetrahydrofuran (1.0 M, 0.62 mL) was added; the mixture was stirred for 10 minutes, then it was warmed to 0° C. for 50 minutes. The reaction was quenched by cautious addition of ethyl acetate, followed by a solution of Rochelle's salt. After stirring for 15 minutes, the mixture was extracted with ethyl acetate; the organic extract was washed with brine and dried over Na$_2$SO$_4$. The solvents were removed in vacuo to provide the titled compound (74 mg).

Example 6D (2S)-2-[(1R,3R,7E,17β)-1,3-dihydroxy-2-methylene-9,10-secoestra-5,7-dien-17-yl]propyl 2-(acetyloxy)-2-methyl propanoate Note: The following sequence was performed in a darkened hood. The compound of Example 6C (31 mg, 0.054 mmol) was dissolved in 2 mL of 1,2-dichloroethane; triethylamine (75 μL, excess) was added, followed by 62 μL of acetoxyisobutyryl chloride and a catalytic quantity of 4-dimethylaminopyridine. After 2 hours, the solvents were removed in vacuo, and the residue was partitioned between ether and 1 N aqueous HCl. The organic extract was washed with brine and dried over Na$_2$SO$_4$. The solvents were removed in vacuo, and the residue was purified by chromatography on an Analogix IntelliFlash 280™, eluting with a gradient from 0% to 8% ethyl acetate in hexanes. The product (40 mg) was dissolved in 2 mL of 1 N tetra-n-butylammonium fluoride in tetrahydrofuran and stirred at ambient temperature for 2.5 hours. The reaction mixture was partitioned between 3:1 ethyl acetate/hexanes and water. The organic phase was washed with brine and dried over Na$_2$SO4. The solvents were removed in vacuo, and the residue was purified by chromatography on an Analogix Intelliflash 280™, eluting with a gradient from 30% to 50% ethyl acetate in hexanes to furnish the titled compound (3.6 mg). $^1$H NMR (400 MHz, CD$_2$Cl$_2$) δ ppm 6.33 (d, J=11.0 Hz, 1 H) 5.89 (d, J=11.4 Hz, 1 H) 5.06 (d, J=4.6 Hz, 2 H) 4.34-4.49 (m, 2 H) 4.00-4.13 (m, 1 H) 3.85 (dd, J=10.7, 6.8 Hz, 1 H) 2.70-2.90 (m, 2 H) 2.55 (dd, J=13.2, 4.0 Hz, 1 H) 2.22-2.38 (m, 2 H) 1.96-2.08 (m, 5 H) 1.84-1.93 (m, 2 H) 1.65-1.76 (m, 4 H) 1.55-1.62 (m, 2 H) 1.55-1.60 (m, 1 H) 1.49-1.57 (m, 6 H) 1.30-1.46 (m, 3 H) 0.97-1.06 (m, 3 H) 0.58 (s, 3 H); MS (+DCI) m/z 492 (M+NH$_4$)$^+$.

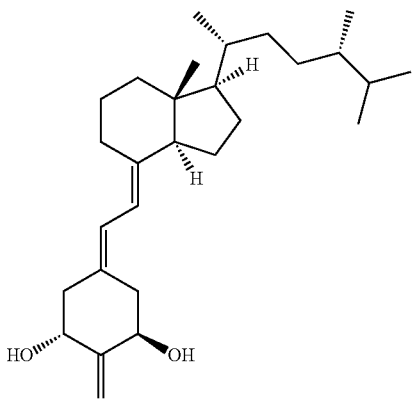 [SMILES: C=C1[C@H](O)CC(=C/C=C2\CCC[C@]3(C)[C@@H]([C@H](C)CC[C@H](C)C(C)C)CC[C@@H]23)C[C@H]1O]

Example 7

(1R,3R,7E)-2-methylene-17-[(1R,4S)-1,4,5-trimethylhexyl]-9,10-secoestra-5,7-diene-1,3-diol Example 7A (1R,3aR,4S,7aR)-7a-methyl-1-[(1R,2E,4R)-1,4,5-trimethylhex-2-enyl]octahydro-1H-inden-4-ol The title compound was prepared by applying the procedures developed by Toh and Okamura in J. Org. Chem. 1983, 48, 1414, but using Vitamin D2 as the starting material. In this manner 20.6 g (52 mmol) of Vitamin D2 was converted to 4.75 g of the desired product (33% overall yield for four-step sequence).

Example 7B (1R,3aR,4S,7aR)-7a-methyl-1-[(1R,4S)-1,4,5-trimethylhexyl]octahydro-1H-inden-4-ol The compound of Example 7A (400 mg, 1.4 mmol) was dissolved in 20 mL of acetic acid and hydrogenated using a 10% platinum on carbon catalyst. After purging with nitrogen and filtering to remove catalyst, the solvent was removed in vacuo, and the residue was partitioned between ethyl acetate and saturated aqueous sodium bicarbonate. The organic phase was washed with brine and dried over sodium sulfate. The solvents were removed in vacuo, and the residue was purified by chromatography on an Analogix Intelliflash 280™, eluting with a gradient from 5% to 30% ethyl acetate in hexanes to furnish the titled compound, 390 mg.

Example 7C (1R,3aR,7aR)-7a-methyl-1-[(1R,4S)-1,4,5-trimethylhexyl]octahydro-4H-inden-4-one The compound of Example 7B (66 mg, 0.25 mmol) was dissolved in 5 mL of dichloromethane and cooled to 0° C.; 370 mg of pyridinium dichromate and 2 mg of pyridinium p-toluenesulfonate were added, and the resultant mixture was shaken at ambient temperature for 4 hours. The reaction was filtered first through a pad of diatomaceous earth, then through a pad of silica gel, with ethyl acetate washes. The combined filtrate was concentrated and purified by chromatography on an Analogix Intelliflash 280™, eluting with 10% ethyl acetate in hexanes to provide the titled compound, 56 mg.

Example 7D (1R,3R,7E)-2-methylene-17-[(1R,4S)-1,4,5-trimethylhexyl]-9,10-secoestra-5,7-diene-1,3-diol Note: The following sequence was performed in a darkened hood. The compound of Example 6A (20 mg, 0.034 mmol) was combined with the compound of Example 7C (19 mg, 0.068 mmol), and the resultant mixture was dried by azeotroping twice with 1 mL of toluene. Tetrahydrofuran (1 mL) was added, and the solution was cooled to −78° C. A solution of lithium bis(trimethylsilyl)amide (1M in tetrahydrofuran; 0.30 mL) was added dropwise in two portions, producing a yellow-orange color that fades over 20 minutes. The solution was warmed to 0° C. and stirred at this temperature for 20 minutes. The reaction was quenched by addition of 1 mL of 1 N aqueous ammonium chloride, and the mixture was extracted with ethyl acetate. The organic extract was washed with brine and dried over sodium sulfate. The solvents were removed in vacuo, and the residue was purified by chromatography on an Analogix Intelliflash 280™, eluting with 2% ethyl acetate in hexanes. The product (10 mg) was dissolved in 0.3 mL of 1 N tetra-n-butylammonium fluoride in tetrahydrofuran and stirred overnight at ambient temperature. The reaction mixture was partitioned between 3:1 ethyl acetate/hexanes and water. The organic phase was washed with brine and dried over sodium sulfate. The solvents were removed in vacuo, and the residue was purified by chromatography on an Analogix Intelliflash 280™, eluting with 30% ethyl acetate in hexanes providing the titled compound, 6 mg. $^1$H NMR (400 MHz, $CD_2Cl_2$) δ ppm 6.33 (d, J=11.4 Hz, 1 H) 5.88 (d, J=11.0 Hz, 1 H) 5.06 (d, J=4.3 Hz, 2 H) 4.34-4.51 (m, 2 ) 2.83 (d, J=4.3 Hz, 2 H) 2.78 (d, J=4.6 Hz, 2 H) 2.55 (dd, J=13.2, 4.0 Hz, 1 H) 2.21-2.43 (m, 4 H) 1.97-2.08 (m, 2 H) 1.82-1.99 (m, 2 H) 1.52-1.63 (m, 3 H) 1.31-1.47 (m, 4 H) 1.18-1.34 (m, 3 H) 0.83-0.93 (m, 6 H) 0.73-0.83 (m, 6 H) 0.55 (s, 3 H); MS (DCI+) m/z 432 (M+$NH_4$)$^+$.

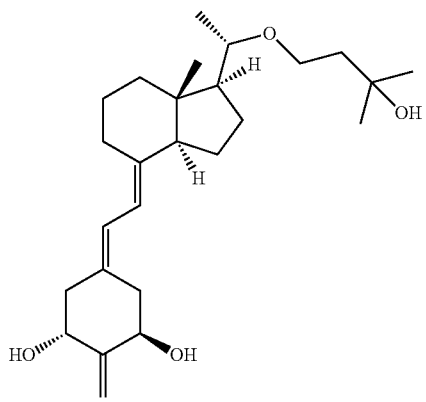 [SMILES: C=C1[C@H](O)CC(=C/C=C2\CCC[C@]3(C)[C@@H]([C@H](C)OCCC(C)(C)O)CC[C@@H]23)C[C@H]1O]

Example 8

(1R,3R,7E,17β)-17-[(1S)-1-(3-hydroxy-3-methylbutoxy)ethyl]-2-methylene-9,10-secoestra-5,7-diene-1,3-diol Example 8A (1Z,3aR,4S,7aS)-1-ethylidene-7a-methyloctahydro-1H-inden-4-ol The titled compound was prepared according to the procedures described by Daniewski and Liu in J. Org. Chem. 2001, 66(2), 626-628.

Example 8B tert-butyl{[(1Z,3aR,4S,7aS)-1-ethylidene-7a-methyloctahydro-1H-inden-4-yl]oxy}dimethylsilane The compound of Example 8A (0.74 g, 4.1 mmol) was dissolved in 4 mL of dimethylformamide; 0.4 g of imidazole was added, followed by 0.7 g of tert-butyldimethylsilyl chloride. The resultant mixture was stirred at ambient temperature for 4 hours; equal portions of tert-butyldimethylsilyl chloride and imidazole were added, and the mixture was heated overnight at 60° C. Water was added; the mixture was stirred at ambient temperature for 30 minutes, and then extracted with ether. The organic phase was washed sequentially with 1 N aqueous $H_3PO_4$, water, and brine, and dried over $Na_2SO_4$. The solvents were removed in vacuo, and the residue was purified by chromatography on an Analogix Intelliflash 280™, eluting with a gradient of 0% to 10% ethyl acetate in hexanes. The titled compound was isolated contaminated with some unreacted starting material (0.31 g, 42%).

Example 8C (1S)-1-((1S,3aR,4S,7aR)-4-{[tert-butyl(dimethyl)silyl]oxy}-7a-methyloctahydro-1H-inden-1-yl)ethanol The compound of Example 8B (1.9 g, 6.4 mmol) was taken up in a solution of 9-borabicyclo[3.3.1]nonane (9-BBN) (0.5 M in tetrahydrofuran; 28 mL); the mixture was warmed at 45° C. for 5 hours, then cooled to 0° C. and quenched by the addition of a combination of 8 mL of 2 N NaOH and 4 mL of 30% hydrogen peroxide solution. The resultant solution was warmed to ambient temperature and stirred overnight. The reaction mixture was extracted with ethyl acetate; the organic phase was washed with brine and dried over $Na_2SO_4$. The solvents were removed in vacuo, and the residue was purified by chromatography on an Analogix Intelliflash 280™, eluting with a gradient of 10% to 90% ethyl acetate in hexanes to furnish the titled compound (quantitative).

Example 8D 3-(bromomethyl)-2,2-dimethyloxirane

The title compound was prepared according to the procedure described by Shimizu and coworkers in Org. Proc. Res. & Dev. 2005, 9, 278-287.

Example 8E

4-{[(1S)-1-((1S,3aR,4S,7aR)-4-{[tert-butyl(dimethyl)silyl]oxy}-7a-methyloctahydro-1H-inden-1-yl)ethyl]oxy}-2-methylbutan-2-ol The compound of Example 8C (1.1 g, 3.5 mmol) was dissolved in 5 mL of tetrahydrofuran; sodium hydride (0.28 g of 60% oil dispersion) was added, and the mixture was stirred at ambient temperature for 10 minutes while gas evolution ceased. The compound of Example 8D (1.2 g) was added, and the mixture was heated at reflux for 60 minutes. The mixture was cooled to ambient temperature, and 6.5 mL of 1 N lithium aluminum hydride solution in tetrahydrofuran was added dropwise. (Caution: after a brief induction period, this reaction proceeds with a vigorous exotherm.) The mixture is stirred for 2 hours as the exotherm subsides, then the reaction was quenched by the addition of 10 mL of ethyl acetate (more exothermic reaction ensues). Standard Fieser workup provides a gelatinous mass which is stirred with solid $Na_2SO_4$ for 2 hours, then filtered through a pad of diatomaceous earth washing with ethyl acetate. The combined washes were concentrated in vacuo, and the residue was purified by chromatography on an Analogix Intelliflash 280™, eluting with a gradient of 10% to 80% ethyl acetate in hexanes. The more polar fraction is recovered starting alcohol; the less-polar mixed fractions are re-chromatographed on an Analogix Intelliflash 280™, eluting with a gradient of 0% to 40% ethyl acetate in hexanes to give the titled compound (0.80 g, 57%).

Example 8F (1S,3aR,4S,7aS)-1-[(1S)-1-(3-hydroxy-3-methylbutoxy)ethyl]-7a-methyloctahydro-1H-inden-4-ol The compound of Example 8E (230 mg, 0.58 mmol) is dissolved in 8 mL of 1 N tetra-n-butylammonium fluoride in tetrahydrofuran and warmed overnight at 80° C. The reaction mixture is partitioned between ether and water; the organic phase was washed with brine and dried over $Na_2SO_4$. The solvents were removed in vacuo, and the residue was purified by chromatography on an Analogix Intelliflash 280™, eluting with a gradient of 0% to 50% ethyl acetate in hexanes to isolate the titled compound (140 mg, 85%).

Example 8G (1S,3aR,7aR)-1-[(1S)-1-(3-hydroxy-3-methylbutoxy)ethyl]-7a-methyloctahydro-4H-inden-4-one The compound of Example 8F (70 mg, 0.25 mmol) was dissolved in 1.5 mL of dichloromethane; 350 mg of pyridinium dichromate and 15 mg of pyridinium p-toluenesulfonate were added, and the resultant mixture was stirred overnight at ambient temperature. Solvents were removed in vacuo; the residue was taken up in ethyl acetate and filtered through diatomaceous earth washing with ethyl acetate. The filtrate was concentrated and the residue was purified by chromatography on an Analogix Intelliflash 280™, eluting with a gradient of 10% to 40% ethyl acetate in hexanes, to isolate the titled compound (65 mg, 73%).

Example 8H (1R,3R,7E,17β)-17-[(1S)-1-(3-hydroxy-3-methylbutoxy)ethyl]-2-methylene-9,10-secoestra-5,7-diene-1,3-diol Note: The following sequence was performed in a darkened hood. The compound of Example 6A (50 mg, 0.088 mmol) was combined with the compound of Example 8G (32 mg, 0.09 mmol), and the resultant mixture was dried by azeotroping twice with 1 mL of toluene. Tetrahydrofuran (1.5 mL) was added, and the solution was cooled to −78° C. A solution of lithium bis(trimethylsilyl)amide (1 M in tetrahydrofuran; 0.20 mL) was added dropwise in two portions, producing a yellow-orange color that fades over 20 minutes. The solution was warmed to 0° C. and stirred at this temperature for 15 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo; the residue was dissolved in 1.5 mL of 1 N tetra-n-butylammonium fluoride in tetrahydrofuran and stirred overnight at ambient temperature. The reaction mixture was partitioned between ethyl acetate and water. The organic phase was washed with brine and dried over $Na_2SO_4$. The solvents were removed in vacuo, and the residue was purified by chromatography on an Analogix IntelliFlash 280™, eluting with a gradient of 10% to 100% ethyl acetate in hexanes to provide the titled compound (18 mg). $^1$H NMR (500 MHz, $CD_2Cl_2$) δ ppm 6.32 (d, J=11.3 Hz, 1 H) 5.90 (d, J=11.3 Hz, 1 H) 5.06 (d, J=7.0 Hz, 2 H) 4.33-4.50 (m, 2 H) 3.75-3.90 (m, 1 H) 3.41-3.55 (m, 2 H) 3.26 (dd, J=7.9, 6.1 Hz, 1 H) 2.69-2.89 (m, 2 H) 2.55 (dd, J=13.1, 4.0 Hz, 1 H) 2.21-2.39 (m, 2 H) 1.96-2.04 (m, 3 H) 1.89 (dd, J=15.4, 2.9 Hz, 2 H) 1.50-1.65 (m, 6 H) 1.31 (d, J=4.3 Hz, 1 H) 1.14-1.27 (m, 12 H) 0.54 (s, 3 H); MS (+ESI) m/z 441 (M+Na)$^+$.

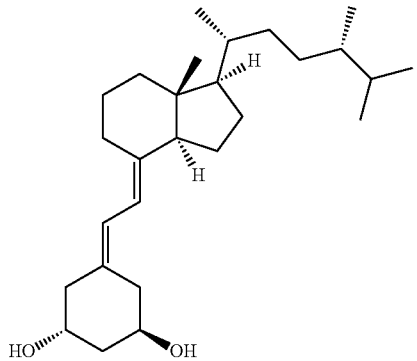 [SMILES: CC(C)[C@@H](C)CC[C@@H](C)[C@H]1CC[C@H]2/C(=C/C=C3C[C@@H](O)C[C@H](O)C3)CCC[C@]12C]

Example 9

(1R,3R,7E)-17-[(1R,4S)-1,4,5-trimethylhexyl]-9,10-secoestra-5,7-diene-1,3-diol

Example 9A

[2-((3R,5R)-3,5-bis{[tert-butyl(dimethyl)silyl]oxy}cyclohexylidene)ethyl](diphenyl)phosphine oxide The title compound was prepared according to the procedures described by DeLuca et al. in EP 516410 B1.

Example 9B (1R,3R,7E)-17-[(1R,4S)-1,4,5-trimethylhexyl]-9,10-secoestra-5,7-diene-1,3-diol Note: The following sequence was performed in a darkened hood. The compound of Example 9A (20 mg, 0.034 mmol) was combined with the compound of Example 7C (20 mg, 0.07 mmol), and the resultant mixture was dried by azeotroping twice with 1 mL of toluene. Tetrahydrofuran (1 mL) was added, and the solution was cooled to −78° C. A solution of lithium bis(trimethylsilyl)amide (1M in tetrahydrofuran; 0.20 mL) was added dropwise in two portions, producing a yellow-orange color that fades over 20 minutes. The solution was warmed to 0° C. and stirred at this temperature for 20 minutes. The reaction was quenched by addition of 1 mL of 1 N aqueous NH$_4$Cl, and the mixture was extracted with ethyl acetate. The organic extract was washed with brine and dried over Na$_2$SO$_4$. The solvents were removed in vacuo, and the residue was dissolved in 1 mL of 0.5 N tetra-n-butylammonium fluoride in tetrahydrofuran and stirred overnight at ambient temperature. The reaction mixture was partitioned between 3:1 ethyl acetate/hexanes and water. The organic phase was washed with brine and dried over Na$_2$SO$_4$. The solvents were removed in vacuo, and the residue was purified by chromatography on an Analogix Intelliflash 280™, eluting with a gradient of 50% to 60% ethyl acetate in hexanes to furnish the titled compound (6 mg). $^1$H NMR (500 MHz, CD$_2$Cl$_2$) δ ppm 6.28 (d, J=11.3 Hz, 1 H) 5.86 (d, J=11.3 Hz, 1 H) 3.90-4.15 (m, 2 H) 2.61-2.85 (m, 2 H) 2.45 (dd, J=13.3, 3.5 Hz, 1 H) 2.11-2.26 (m, 2 H) 1.98-2.05 (m, 4 H) 1.81-1.94 (m, 4 H) 1.72-1.79 (m, 1 H) 1.61-1.72 (m, 4 H) 1.29-1.36 (m, 3 H) 1.22-1.38 (m, 7 H) 0.76-0.89 (m, 9 H) 0.54 (s, 3 H); MS (+ESI) m/z 420 (M+NH$_4$)$^+$.

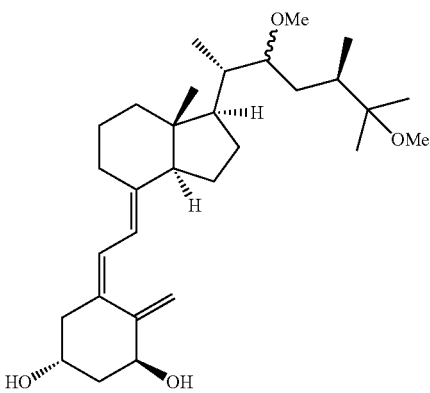 [SMILES: C=C1/C(=C\C=C2/CCC[C@]3(C)[C@@H]([C@H](C)C(C[C@@H](C)C(C)(C)OC)OC)CC[C@@H]23)C[C@@H](O)C[C@@H]1O]

Example 10

(1S,3R,5Z,7E,24R)-22,25-dimethoxy-9,10-secoergosta-5,7,10-triene-1,3-diol

Example 10A

[(2Z)-2-((3S,5R)-3,5-bis{[tert-butyl(dimethyl)silyl]oxy}-2-methylenecyclohexylidene)ethyl](diphenyl)phosphine oxide The title compound was prepared according to the procedures described by Radinov and coworkers in J. Org. Chem. 2002, 67(5), 1580-1587.

Example 10B (3S)-2,3-dimethyl-4-(phenylsulfonyl)butan-2-ol

The title compound was prepared according to the procedures described by Kutner et al. in J. Org. Chem. 1988, 53, 3450-3457.

Example 10C trimethyl{[(2S)-1,1,2-trimethyl-3-(phenylsulfonyl)propyl]oxy}silane

The compound of Example 10B (0.95 g, 3.9 mmol) was dissolved in 3 mL of dimethylformamide; 1 mL of 1-(trimethylsilyl)imidazole was added, and the resultant solution was stirred overnight at ambient temperature, then heated at 80° C. for 8 hours. The crude mixture was partitioned between ethyl acetate and water; the organic phase was washed with brine and dried over Na$_2$SO$_4$. The solvents were removed in vacuo, and the residue was purified by chromatography on an Analogix Intelliflash 280™, eluting with a gradient of 0% to 20% ethyl acetate in hexanes to provide the titled compound (1.18 g, 96%).

Example 10D (2S)-2-((1R,3aR,4S,7aR)-4-{[tert-butyl(dimethyl)silyl]oxy}-7a-methyloctahydro-1H-inden-1-yl)propyl pivalate The compound of Example 1B (5.05 g, 24 mmol) was dissolved in 35 mL of dichloromethane and 15 mL of pyridine; the solution was cooled to 0° C., and 3.3 mL of pivaloyl chloride was added dropwise over 5 minutes. The resultant mixture was stirred at 0° C. for 4 hours, and then the reaction mixture was warmed to ambient temperature over 30 minutes. The reaction was quenched with water, and the mixture was concentrated in vacuo with the bath maintained below ambient temperature. The crude material was partitioned between ether and 0.5 N aqueous HCl; the organic phase was washed with 0.5 N aqueous HCl, then brine, and dried over Na$_2$SO$_4$. The solvents were removed in vacuo; the residue was dissolved in 15 mL of dimethylformamide. Imidazole (2.0 g) and tert-butyldimethylsilyl chloride (4.0 g) were added, and the resultant mixture was stirred at ambient temperature for 4 days, and then warmed to 60° C. for 4 hours. Solvents were removed in vacuo; the residue was partitioned between ethyl acetate and 1.5 N aqueous HCl. The organic phase was washed with brine and dried over Na$_2$SO$_4$. The solvents were removed in vacuo, and the residue was purified by chromatography on an Analogix Intelliflash 280™, eluting with a gradient of 0% to 60% ethyl acetate in hexanes to provide the titled compound (6.45 g, 66%).

Example 10E (2S)-2-((1R,3aR,4S,7aR)-4-{[tert-butyl(dimethyl)silyl]oxy}-7a-methyloctahydro-1H-inden-1-yl)propan-1-ol The compound of Example 10D (6.45 g, 16 mmol) was dissolved in 30 mL of ether and cooled to −30° C.; 35 mL of a 1 N solution of lithium aluminum hydride in ether was added at a rate so as to maintain a constant temperature and a modest rate of gas evolution. The mixture was stirred at −30° C. for 10 minutes, and then it was warmed to 0° C. for 1 hour. The reaction was quenched by the careful addition of ethyl acetate (Caution! Vigorous gas evolution) and stirred for 10 minutes, then quenched with a solution of Rochelle's salt. The resultant mixture was partitioned between ethyl acetate and water; the organic phase was washed with brine and dried over Na$_2$SO$_4$. The solvents were removed in vacuo, and the residue was purified by chromatography on an Analogix Intelliflash 280™, eluting with a gradient of 5% to 30% ethyl acetate in hexanes.

Example 10F (2S,5R)-2-((1R,3aR,4S,7aR)-4-{[tert-butyl(dimethyl)silyl]oxy}-7a-methyloctahydro-1H-inden-1-yl)-5,6-dimethyl-6-[(trimethylsilyl)oxy]heptan-3-ol The compound of Example 10E (200 mg, 0.61 mmol) was dissolved in 2 mL of dichloromethane; 100 mg of 4 Å molecular sieves were added, followed by 15 mg of tetrapropylammonium perruthenate and 75 mg of 4-methylmorpholine N-oxide. The mixture was stirred for 2 hours at ambient temperature, and then filtered through diatomaceous earth to removed solids. The crude product was purified by silica gel chromatography using an Analogix IntelliFlash™ 40, eluting with a gradient of 5% to 30% ethyl acetate in hexanes. The compound of Example 10C (200 mg, 0.63 mmol) was combined with this aldehyde according to the coupling procedure described by Kutner et al. in J. Org. Chem. 1988, 53, 3450-3457. The named product, the result of desulfurization without elimination, was isolated after chromatographic purification using an Analogix Intelliflash 280™, eluting with a gradient of 0% to 50% ethyl acetate in hexanes.

Example 10G tert-butyl({(1R,3aR,4S,7aR)-1-[(1S,4R)-2,5-dimethoxy-1,4,5-trimethylhexyl]-7a-methyloctahydro-1H-inden-4-yl}oxy)dimethylsilane The compound of Example 10F (50 mg, 0.1 mmol) was dissolved in 0.5 mL of dry tetrahydrofuran; 20 mg of NaH (60% oil dispersion; in excess) was added, followed (after gas evolution had ceased) by 0.1 mL (excess) of iodomethane. The resultant mixture was stirred overnight at ambient temperature, then quenched with water and extracted with ethyl acetate. The organic phase was washed with brine and dried over $Na_2SO_4$. The solvents were removed in vacuo, and the residue was purified by chromatography on an Analogix Intelliflash 280™, eluting with a gradient of 0% to 20% ethyl acetate in hexanes to provide the titled compound (43 mg, 94%).

Example 10H.

(1R,3aR,4S,7aR)-1-[(1S,4R)-2,5-dimethoxy-1,4,5-trimethylhexyl]-7a-methyloctahydro-1H-inden-4-ol The compound of Example 10G (42 mg, 0.093 mmol) was dissolved in 1.5 mL of 1 N tetra-n-butylammonium fluoride in tetrahydrofuran, and warmed overnight at 80° C. The reaction mixture was partitioned between ethyl acetate and water; the organic phase was washed with brine and dried over $Na_2SO_4$. The solvents were removed in vacuo, and the residue was purified by chromatography on an Analogix Intelliflash 280™, eluting with a gradient of 0% to 25% ethyl acetate in hexanes to provide the titled compound (27 mg, 86%).

Example 10I (1R,3aR,7aR)-1-[(1S,4R)-2,5-dimethoxy-1,4,5-trimethylhexyl]-7a-methyloctahydro-4H-inden-4-one The compound of Example 10H (27 mg, 0.079 mmol) was dissolved in 1 mL of dichloromethane; 150 mg of pyridinium dichromate and 10 mg of pyridinium p-toluenesulfonate were added, and the resultant mixture was stirred overnight at ambient temperature. Diatomaceous earth (~500 mg) was added, and the solvents were removed in vacuo. The residue was taken up in ethyl acetate and loaded onto a plug of silica. Elution with a gradient of 50% to 100% ethyl acetate in hexanes, and concentration of the combined eluate, gave a product which was carried forward without further purification.

Example 10J (1S,3R,5Z,7E,24R)-22,25-dimethoxy-9,10-secoergosta-5,7,10-triene-1,3-diol Note: The following sequence was performed in a darkened hood. The compound of Example 10A (20 mg, 0.035 mmol) was combined with the compound of Example 10I (12 mg, 0.036 mmol) in 1 mL of toluene; the solvent was removed in vacuo to dry the reagents thoroughly. The residue was taken up in 1.5 ml of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. An additional 0.05 mL of the lithium bis(trimethylsilyl)amide reagent was added; the resultant mixture was stirred at −78° C. for 1 hour, then warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was dissolved in 1 mL of 1 N tetra-n-butylammonium fluoride in tetrahydrofuran. After stirring overnight at ambient temperature, the reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 10% to 100% ethyl acetate in hexanes, followed by a solvent hold at 100% ethyl acetate to furnish the titled compound (1.2 mg). $^1$H NMR (400 MHz, $CD_2Cl_2$) δ ppm 6.37 (d, J=11.0 Hz, 1 H) 6.03 (d, J=11.4 Hz, 1 H) 4.38 (dd, J=4.3 Hz, 1 H) 4.09-4.24 (m, 2 H) 3.25-3.34 (m, 3 H) 3.17-3.21 (m, 1 H) 3.07-3.16 (m, 3 H) 2.86 (s,1 H) 2.55 (d, J=3.1 Hz, 1 H) 2.27 (dd, J=13.3, 6.3 Hz, 1 H) 1.59-1.79 (m, 7 H) 1.42-1.54 (m, 4 H) 1.18-1.34 (m, 5 H) 1.01-1.13 (m, 7 H) 0.81-1.00 (m, 9 H) 0.51-0.63 (m, 3 H).

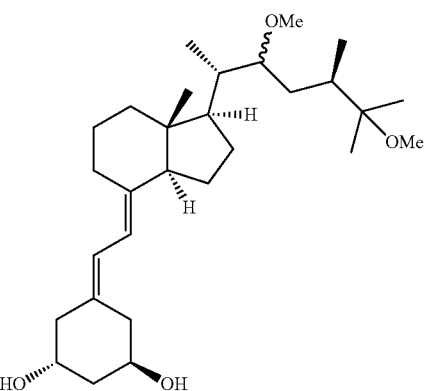 [SMILES: COC(C[C@@H](C)C(C)(C)OC)[C@@H](C)[C@H]1CC[C@H]2/C(=C/C=C3C[C@@H](O)C[C@H](O)C3)CCC[C@]12C]

Example 11

(1R,3R,7E,17β)-17-[(1S,4R)-2,5-dimethoxy-1,4,5-trimethylhexyl]-9,10-secoestra-5,7-diene-1,3-diol Note: The following sequence was performed in a darkened hood. The compound of Example 9A (20 mg, 0.035 mmol) was combined with the compound of Example 10I (12 mg, 0.036 mmol) in 1 mL of toluene; the solvent was removed in vacuo to dry the reagents thoroughly. The residue was taken up in 1.5 ml of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. An additional 0.05 mL of the lithium bis(trimethylsilyl)amide reagent was added; the resultant mixture was stirred at −78° C. for 1 hour, then warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was dissolved in 1 mL of 1 N tetra-n-butylammonium fluoride in tetrahydrofuran. After stirring overnight at ambient temperature, the reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 10% to 100% ethyl acetate in hexanes, followed by a solvent hold at 100% ethyl acetate to provide the titled compound (4.4 mg). $^1H$ NMR (400 MHz, $CD_2Cl_2$) δ ppm 6.29 (d, J=11.4 Hz, 1 H) 5.87 (d, J=11.4 Hz, 1 H) 4.02 (d, J=26.7 Hz, 1 H) 3.29 (s, 3 H) 3.17-3.27 (m, 1 H) 3.12 (s, 3 H) 2.75-2.90 (m, 1 H) 2.63-2.73 (m, 1 H) 2.44 (d, J=3.7 Hz, 2 H) 2.18 (d, J=5.5 Hz, 2 H) 1.82-2.03 (m, 4 H) 1.61-1.70 (m, 2 H) 1.60-1.81 (m, 7 H) 1.34-1.59 (m, 6 H) 1.19-1.40 (m, 3 H) 1.07 (s, 6 H) 0.82-0.96 (m, 3 H) 0.56 (s, 3 H).

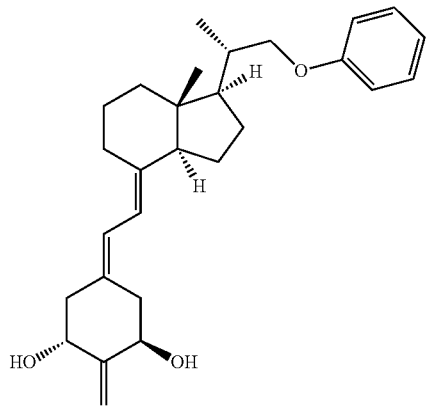 [SMILES: C=C1[C@H](O)CC(=C/C=C2\CCC[C@]3(C)[C@@H]([C@H](C)COc4ccccc4)CC[C@@H]23)C[C@H]1O]

Example 12

(1R,3R,7E,17β)-2-methylene-17-[(1S)-1-methyl-2-phenoxyethyl]-9,10-secoestra-5,7-diene-1,3-diol Note: The following sequence was performed in a darkened hood. The compound of Example 6C (16 mg, 0.028 mmol) was combined with 8 mg of phenol and 20 mg of triphenylphosphine in 2 mL of toluene, followed by 18 mg of di-tert-butyl azodicarboxylate. The mixture was purged with argon and heated at 85° C. for 4 hours. After solvent removal in vacuo, the residue was purified by chromatography on an Analogix IntelliFlash 280™, eluting with a gradient from 0% to 5% ethyl acetate in hexanes. The product (6 mg) was dissolved in 1.5 mL of 1 N tetra-n-butylammonium fluoride in tetrahydrofuran. After stirring for 3 hours at ambient temperature, the reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 25% to 45% ethyl acetate in hexanes to provide the titled compound (4 mg). $^1H$ NMR (500 MHz, $CD_2Cl_2$) δ ppm 7.20-7.37 (m, 2 H) 6.76-7.01 (m, 3 H) 6.34 (d, J=11.0 Hz, 1 H) 5.90 (d, J=11.3 Hz, 1 H) 5.06 (d, J=5.5 Hz, 2 H) 4.32-4.54 (m, 2 H) 3.94 (dd, J=3.1 Hz, 1 H) 3.69 (dd, J=7.3 Hz, 1 H) 2.69-2.94 (m, 2 H) 2.55 (dd, J=13.4, 4.0 Hz, 2 H) 2.19-2.39 (m, 3 H) 1.98-2.14 (m, 4 H) 1.81-1.99 (m, 3 H) 1.64-1.77 (m, 2 H) 1.49-1.66 (m, 2 H) 1.27-1.35 (m, 1 H) 0.85-1.02 (m, 3 H) 0.61 (s, 3 H); MS (+DCI) m/z 440 $(M+NH_4)^+$.

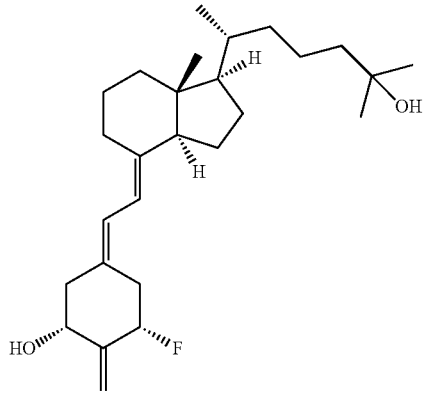 [SMILES: C=C1[C@H](O)C/C(=C/C=C2\CCC[C@]3(C)[C@@H]([C@H](C)CCCC(C)(C)O)CC[C@@H]23)C[C@@H]1F]

Example 13

(1R,3S,5Z,7E,17β)-3-fluoro-17-[(1R)-5-hydroxy-1,5-dimethylhexyl]-2-methylene-9,10-secoestra-5,7-dien-1-ol

Example 13A tert-butyl{[(1R,2R,4R,6R)-4-isopropenyl-1-methyl-7-oxabicyclo[4.1.0]hept-2-yl]oxy}diphenylsilane (R)-Carvone oxide (106 g, 640 mmol, Prepared as described for the enantiomer by Klein and Ohloff in Tetrahedron 1963, 19, 1091-1099) was dissolved in 120 mL of methanol, and the solution was added to a solution of $CeCl_3$ (heptahydrate; 119 g, 320 mmol) in 1.5 L of methanol, pre-cooled to 0° C. The flask was rinsed with 60 mL of methanol, and the mixture was cooled to −20° C. A solution of $NaBH_4$ (2 M in triglyme, 175 mL) was added over 1 hour. After stirring for 30 minutes at −20° C., 720 mL of water was added, and the mixture was allowed to warm to ambient temperature. The organic solvent was removed in vacuo; 800 mL of ethyl acetate was added, followed by sufficient 2 N aqueous HCl (~100 mL) to bring the pH of the solution to ~5.5. The aqueous phase was decanted, and the organic phase was washed with brine and dried over $Na_2SO_4$. The solution was concentrated in vacuo to produce a triglyme solution of the crude alcohol. Dimethylformamide (300 mL) was added, followed by imidazole (70 g, 1000 mmol) and tert-butyldiphenylsilyl chloride (236 g, 1000 mmol). The mixture was allowed to stir at ambient temperature for 84 hours, with an additional 50 mL of dimethylformamide added after 24 hours to improve solubility. The mixture was cooled in an ice bath, 30 mL of water was added, and stirring was continued for 30 minutes. The reaction was partitioned between heptane and water; the organic phase was washed sequentially with water and brine, and dried over $MgSO_4$. After concentrating in vacuo, the crude product was purified by flash chromatography, eluting with a gradient of 1:5 to 1:4 dichloromethane in hexanes to provide the titled compound (206 g, 79%).

Example 13B (1R,3R,5R,6R)-5-{[tert-butyl(diphenyl)silyl]oxy}-6-methyl-7-oxabicyclo[4.1.0]heptan-3-ol A mixture of the compound of Example 13A (34 g, 92 wt %, 77 mmol) and $NaHCO_3$ (3.3 g, 39 mmol) in 300 mL dichloromethane and 60 mL methanol was cooled to ←70° C. and treated with ozone (7-8 psi, 90 volts, 4 slpm) until a persistent blue color was observed. After purging with nitrogen to remove the color, the reaction was warmed to ~0° C., then filtered through paper and concentrated. After chasing with 2×100 mL benzene, 300 mL of dichloromethane and 60 mL of pyridine were added and the reaction was cooled to <5° C. p-Nitrobenzoyl chloride (22.2 g, 120 mmol) was added and stirred for 1 hour, then the bath was removed and the reaction stirred at ambient temperature overnight. The resulting suspension was concentrated in vacuo to a thick slurry, and then diluted with ethyl acetate, and the solids were removed by filtration. The filtrate was washed with 250 mL of saturated aqueous sodium bicarbonate, then with 100 mL each of 2 N HCl, 1 N HCl, and 2 N HCl, and with 200 mL each of 1 N HCl, saturated aqueous sodium bicarbonate, and brine. The organic layer was dried over $MgSO_4$, filtered and concentrated to yield the crude ester. A sample of this product (20.6 g, 32 mmol) was dissolved in 115 mL methanol; 15 mL water was added, followed by 11.0 g of $K_2CO_3$. After 2 hours, the reaction was quenched with 6.5 mL of acetic acid, and then concentrated in vacuo. The residue was treated with 100 mL water, and then extracted sequentially with 150 mL and 100 mL of ethyl acetate. The combined organic layers were washed with 100 mL each of saturated aqueous sodium bicarbonate, then 10% aqueous NaCl, then 20% aqueous NaCl. The ethyl acetate layer was dried over $MgSO_4$, filtered and concentrated. Chromatography (Isco CombiFlash® system, Analogix RS 300 300 g column, 1:9 ethyl acetate: dichloromethane for 5 minutes, then to 12:88 over 35 minutes, then hold for 10 minutes) provided the title compound (10.3 g, 91 wt %, 76%).

Example 13C tert-butyl({(1R,2R,4R,6R)-1-methyl-4-[(triethylsilyl)oxy]-7-oxabicyclo[4.1.0]hept-2-yl}oxy)diphenylsilane The compound of Example 13B (16.0 g, 42 mmol) was dissolved in 20 mL of dimethylformamide; 7.1 g of imidazole (100 mmol, 2.5 equivalents) was added, followed by 10.5 mL of chlorotriethylsilane. The resultant mixture was stirred overnight at ambient temperature, then was diluted with water and extracted with ethyl acetate. The organic phase was concentrated washed with brine and dried over $Na_2SO_4$. After concentrating in vacuo, the residue was purified by flash chromatography, eluting with a gradient from 50% to 100% dichloromethane in hexanes to provide the titled compound (14.0 g, 90%).

Example 13D (1R,3R,5R)-3-{[tert-butyl(diphenyl)silyl]oxy}-2-methylene-5-[(triethylsilyl)oxy]cyclohexanol 2,2,6,6-Tetramethylpiperidine (47 mL) was dissolved in 250 mL of toluene; n-butyllithium (2.5 M in hexanes, 113 mL) was added, and the resultant mixture was stirred for 40 minutes. Diethylaluminum chloride (1.0 M in hexanes, 289 mL) was added, and stirring was continued for 1 hour. The solution was cooled to 0° C.; the compound of Example 13C (34.9 g, 70 mmol) was dissolved in 100 mL of toluene and added over 5 minutes. The mixture was stirred for 3 hours, warming slowly to ambient temperature. The reaction was quenched by the addition of a saturated aqueous $NH_4Cl$ solution; after stirring for 5 minutes, 2 N aqueous HCl solution was added to bring the pH to ~1.5. The mixture was extracted with ethyl acetate; the organic phase was washed sequentially with water and brine, and dried over $Na_2SO_4$. The solvents were removed in vacuo to produce the titled compound, which was carried forward without further purification.

Example 13E (3R,5R)-3-{[tert-butyl(dimethyl)silyl]oxy}-5-{[tert-butyl(diphenyl)silyl]oxy}-4-methylenecyclohexanone The compound of Example 13D (8.5 g, 17 mmol) was dissolved in 50 mL of dichloromethane; 4.4 mL of 2,6-lutidine was added, and the resultant solution was cooled to 0° C. tert-Butyldimethylsilyl trifluoromethanesulfonate (5.9 mL) was added, and the mixture was stirred for 1 hour. The reaction was quenched by the addition of saturated aqueous $NH_4Cl$, the solvents were removed in vacuo, and the residue was partitioned between ethyl acetate and water. The organic phase was washed with 1 N aqueous HCl, then brine, and dried over $Na_2SO_4$. The solvents were removed in vacuo; the residue was purified by chromatography on an Analogix IntelliFlash 280™, eluting with a gradient of 2% to 5% ethyl acetate in hexanes. The product (9.3 g) was dissolved in 75 mL of ethanol; pyridinium p-toluenesulfonate (390 mg) was added, and the mixture was stirred at ambient temperature for 1 hour. The solvents were removed in vacuo; the residue was purified by chromatography on an Analogix Intelliflash 280™, eluting with a gradient of 9% to 17% ethyl acetate in hexanes. A sample of this product (5.8 of 6.8 g) was dissolved in 30 mL of dichloromethane; 3.0g of $NaHCO_3$ was added, and the mixture was cooled to 0° C. Dess-Martin reagent (5.9 g) was added, and stirring was continued for 2 hours. The solvents were removed in vacuo, and the residue was partitioned between ethyl acetate and water. The organic phase was washed with 1 N aqueous HCl, then brine, and dried over $Na_2SO_4$. The organic phase was passed through a plug of silica gel and concentrated in vacuo, giving the titled compound (5.5 g, 71%).

Example 13F ethyl (2E)-((3R,5R)-3-{[tert-butyl(diphenyl)silyl]oxy}-5-hydroxy-4-methylenecyclohexylidene)acetate A solution of diisopropylamine (1.2 mL, 9.4 mmol) in 10 mL of tetrahydrofuran was cooled to −78° C.; n-butyllithium (2.5 M in hexanes, 3.6 mL) was added, followed after 5 minutes by ethyl trimethlysilylacetate (1.7 mL). The resultant solution was stirred at −78° C. for 30 minutes, and then a solution of the compound of Example 13E (2.0 g, 4 mmol) in 10 mL of tetrahydrofuran was added over 5 minutes. Stirring was continued for 4 hours. The reaction was quenched by the addition of saturated aqueous $NH_4Cl$; the mixture was warmed to ambient temperature, the partitioned between ethyl acetate and water. The organic phase was washed with 1 N aqueous HCl and brine, and dried over $Na_2SO_4$. The solvents were removed in vacuo; the residue was purified by chromatography on an Analogix IntelliFlash 280™, eluting with a gradient of 5% to 10% ethyl acetate in hexanes. The product (1.9 g) was dissolved in 17 mL of ethanol; 1.3 mL of concentrated HCl was added, and the resultant solution was stirred overnight at ambient temperature. The solvents were removed in vacuo, the residue was taken up in saturated aqueous sodium bicarbonate and extracted with ethyl acetate. The organic phase was concentrated in vacuo and purified by chromatography on an Analogix Intelliflash 280™, eluting with a gradient of 2% to 3% dichloromethane in acetonitrile. The title compound was isolated as the slower-eluting material (0.62 g).

Example 13G ethyl (2Z)-((3R,5S)-3-{[tert-butyl(diphenyl)silyl]oxy}-5-fluoro-4-methylenecyclohexylidene)acetate The compound of Example 13F (96 mg, 0.22 mmol) was dissolved in 2 mL of dichloromethane, and the resultant solution was cooled to −78° C. (Diethylamino)sulfur trifluoride (DAST, 0.12 mL) was added; the mixture was stirred for 30 minutes, then quenched by addition of saturated aqueous sodium bicarbonate solution. The mixture was warmed to ambient temperature; the organic phase was dried over $Na_2SO_4$. The solvents were removed in vacuo; the residue was purified by chromatography on an Analogix Intelliflash 280™, eluting with 10% ethyl acetate in hexanes to give the titled compound (42 mg, 44%).

Example 13H (2Z)-2-((3R,5S)-3-{[tert-butyl(diphenyl)silyl]oxy}-5-fluoro-4-methylenecyclohexylidene)ethanol The compound of Example 13G (40 mg, 0.09 mmol) was dissolved in 1 mL of 1:1 dichloromethane/toluene and cooled to −78° C. Diisobutylaluminum hydride (1 M in hexanes, 0.36 mL) was added, and the mixture was stirred for 20 minutes. The reaction was quenched by the addition of water; the mixture was warmed to ambient temperature, and then acidified to pH~2 by addition of concentrated HCl. The mixture was extracted with ethyl acetate; the organics were washed with brine and dried over $Na_2SO_4$. The solvents were removed in vacuo; the residue was purified by chromatography on an Analogix Intelliflash 280™, eluting with 17% ethyl acetate in hexanes to give the titled compound (25 mg, 68%).

Example 13I

[(2Z)-2-((3R,5S)-3-{[tert-butyl(diphenyl)silyl]oxy}-5-fluoro-4-methylenecyclohexylidene)ethyl](diphenyl)phosphine oxide The compound of Example 13H (180 mg, 0.44 mmol) was dissolved in 2 mL of hexanes; 85 mg (0.28 mmol) of triphosgene was added, and the mixture was cooled to 0° C. Triethylamine (0.22 mL, 1.5 mmol) was added dropwise over 2 minutes; the reaction mixture was stirred for 30 minutes, and then warmed to ambient temperature over 1 hour. Additional hexanes (3 mL) were added, and the reaction mixture was washed sequentially with cold 3% aqueous HCl, water, and brine. The organic phase was dried over $Na_2SO_4$; the solvents were removed in vacuo to furnish crude allylic chloride.

Diphenylphosphine (0.72 g, 7 equivalents) was dissolved in 2 mL of tetrahydrofuran, and the solution was cooled to 0° C. A solution of n-butyllithium (2.5 M in hexanes) was added, and the mixture was stirred for 5 minutes. In the meantime, the above intermediate allylic chloride was dissolved in 1 mL of tetrahydrofuran and cooled to −60° C. The anion solution was added over 5 minutes, and the resultant mixture was stirred at −60° C. for 1 hour. The reaction was quenched with water; the mixture was warmed to ambient temperature and extracted with ethyl acetate. The organic phase was washed with 1 N aqueous HCl and brine, and dried over $Na_2SO_4$. The solvents were removed in vacuo; the residue was purified by chromatography on an Analogix IntelliFlash 280™, eluting with a gradient of 40% to 50% ethyl acetate in hexanes to supply the titled compound (200 mg, 76%).

Example 13J (1R,3aR,7aR)-1-{(1R)-1,5-dimethyl-5-[(trimethylsilyl)oxy]hexyl}-7a-methyloctahydro-4H-inden-4-one The title compound was prepared according to the procedures described by Kiegiel, Wovkulich, and Uskokovic in Tetrahedron Lett. 1991, 32(43), 6057.

Example 13K (1R,3S,5Z,7E,17β)-3-fluoro-17-[(1R)-5-hydroxy-1,5-dimethylhexyl]-2-methylene-9,10-secoestra-5,7-dien-1-ol Note: The following sequence was performed in a darkened hood. The compound of Example 13I (20 mg, 0.034 mmol) was combined with the compound of Example 13J (12 mg, 0.056 mmol) in 1 mL of toluene; the solvent was removed in vacuo to dry the reagents thoroughly. The residue was taken up in 1 mL of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. The resultant mixture was stirred at −78° C. for 1 hour, then warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was dissolved in 1 mL of 1 N tetra-n-butylammonium fluoride in tetrahydrofuran. After stirring overnight at ambient temperature, the reaction mixture was partitioned between ethyl acetate and water. The organic phase was washed with brine and dried over $Na_2SO_4$. The solvents were removed in vacuo, and the residue was purified by chromatography on an Analogix IntelliFlash 280™, eluting with a gradient from 20% to 50% ethyl acetate in hexanes to provide the titled compound (6 mg). $^1$H NMR (500 MHz, $CD_2Cl_2$) δ ppm 6.25-6.41 (m, 1 H) 5.98-6.13 (m, 1 H) 5.16-5.26 (m, 2 H) 4.91 (d, 1 H) 4.02-4.22 (m, 1 H) 2.87-3.05 (m, 1 H) 2.60 (dd, J=12.8, 4.6 Hz, 1 H) 2.42-2.53 (m, 3 H) 2.40 (d, J=15.3 Hz, 1 H) 2.13-2.32 (m, 4 H) 2.00 (s,1 H) 1.80-1.95 (m, 2 H) 1.66-1.79 (m, 2 H) 1.55-1.66 (m, 4 H) 1.27-1.45 (m, 6 H) 1.10-1.25 (m, 9 H) 0.91-1.01 (m, 3 H); MS (+DCI) m/z 436 $(M+NH_4)^+$.

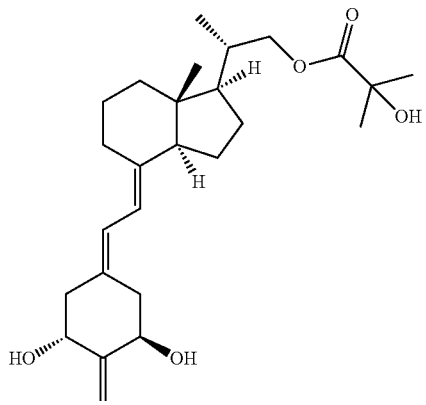 [SMILES: C=C1[C@H](O)CC(=C/C=C2\CCC[C@]3(C)[C@@H]([C@H](C)COC(=O)C(C)(C)O)CC[C@@H]23)C[C@H]1O]

Example 14

(2S)-2-[(1R,3R,7E,17β)-1,3-dihydroxy-2-methylene-9,10-secoestra-5,7-dien-17-yl]propyl 2-hydroxy-2-methylpropanoate The compound of Example 6C (20 mg, 0.034 mmol) was combined with 11 mg (3 equivalents) of 2-hydroxyisobutyric acid and 25 mg (2.8 equivalents) of triphenylphosphine in 1.5 mL of toluene; 22 mg (2.8 equivalents) of di-tert-butyl azodicarboxylate was added, the resultant solution was flushed with argon and heated at 70° C. for 1.5 hours. The mixture was concentrated and purified by chromatography on an Analogix Intelliflash 280™, eluting with a gradient from 5% to 12% ethyl acetate in hexanes. The crude intermediate (21 mg of 25 mg total) was dissolved in 2 mL of 1 N tetra-n-butylammonium fluoride in tetrahydrofuran. After stirring for 3 hours at ambient temperature, the reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 45% to 68% ethyl acetate in hexanes to provide the titled compound (5.1 mg). $^1$H NMR (500 MHz, $CD_2Cl_2$) δ ppm 6.33 (d, J=11.3 Hz, 1 H) 5.90 (d, J=11.3 Hz, 1 H) 5.06 (d, J=5.8 Hz, 1 H) 4.36-4.52 (m, 2 H) 4.16 (dd, J=10.7, 3.4 Hz, 1 H) 3.92 (dd, J=10.7, 7.0 Hz, 1 H) 2.83 (dd, J=12.1, 3.8 Hz, 1 H) 2.76 (dd, J=13.1, 4.6 Hz, 1 H) 2.55 (dd, J=13.1, 4.0 Hz, 1 H) 2.21-2.35 (m, 2 H) 2.02-2.11 (m, 2 H) 1.95-2.04 (m, 2 H) 1.85-1.94 (m, 1 H) 1.64-1.81 (m, 4 H) 1.49-1.65 (m, 4 H) 1.37-1.45 (m, 9 H) 1.04 (d, J=6.7 Hz, 3 H) 0.58 (s, 3 H); MS (+DCI) m/z 364 $(M+NH_4)^+$.

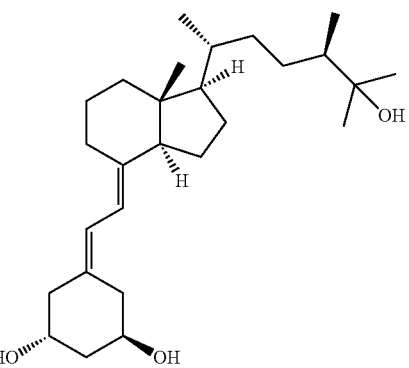

Example 15

(1R,3R,7E,17β)-17-[(1R,4R)-5-hydroxy-1,4,5-trimethylhexyl]-9,10-secoestra-5,7-diene-1,3-diol Example 15A tert-butyl(dimethyl)[((1R,3aR,4S,7aR)-7a-methyl-1-{(1R,2E,4R)-1,4,5-trimethyl-5-[(trimethylsilyl)oxy]hex-2-enyl}octahydro-1H-inden-4-yl)oxy]silane and (3R,4E,6R)-6-((1R,3aR,4S,7aR)-4-{[tert-butyl(dimethyl)silyl]oxy}-7a-methyloctahydro-1H-inden-1-yl)-2,3-dimethylhept-4-en-2-ol The compound of Example 10E (200 mg, 0.61 mmol) was dissolved in 2 mL of dichloromethane; 100 mg of 4 Å molecular sieves were added, followed by 15 mg of tetrapropylammonium perruthenate and 75 mg of 4-methylmorpholine N-oxide. The mixture was stirred for 2 hours at ambient temperature, and then filtered through diatomaceous earth to removed solids. The crude product was purified by silica gel chromatography using an Analogix IntelliFlash™ 40, eluting with a gradient of 5% to 30% ethyl acetate in hexanes. The compound of Example 10C (200 mg, 0.63 mmol) was combined with this aldehyde according to the coupling procedure described by Kutner et al. in J. Org. Chem. 1988, 53, 3450-3457. The named product was isolated as a mixture of trimethylsilyl ether (Fraction A) and hydroxyl (Fraction B) after chromatographic purification using an Analogix IntelliFlash 280™, eluting with a gradient of 0% to 50% ethyl acetate in hexanes. These products were combined and carried forward to the next step.

Example 15B (1R,3aR,4S,7aR)-1-[(1R,2E,4R)-5-hydroxy-1,4,5-trimethylhex-2-enyl]-7a-methyloctahydro-1H-inden-4-ol The mixed fractions of Example 15A were dissolved in 2 mL of 1 N tetra-n-butylammonium fluoride in tetrahydrofuran; the resultant solution was stirred at ambient temperature for 2 hours, warmed overnight at 60° C., and then heated to 80° C. for 3 hours. The reaction was quenched with water and extracted with ethyl acetate. The organic phase was washed with brine and dried over $Na_2SO_4$. The solvents were removed in vacuo, and the residue was purified by chromatography on an Analogix Intelliflash 280™, eluting with a gradient of 10% to 40% ethyl acetate in hexanes to provide the titled compound (72 mg).

Example 15C (1R,3aR,4S,7aR)-1-[(1R,4R)-5-hydroxy-1,4,5-trimethylhexyl]-7a-methyloctahydro-1H-inden-4-ol The compound of Example 15B (89 mg) was dissolved in acetic acid and hydrogenated over 10% platinum on carbon. After purging with nitrogen, the mixture was filtered through a pad of diatomaceous earth to remove catalyst and concentrated in vacuo to give material that was carried forward to the next step without further purification.

Example 15D (1R,3aR,7aR)-7a-methyl-1-{(1R,4R)-1,4,5-trimethyl-5-[(trimethylsilyl)oxy]hexyl}octahydro-4H-inden-4-one The compound of Example 15C (73 mg, 0.25 mmol) was dissolved in 1 mL of dichloromethane; 150 mg of pyridinium dichromate and 10 mg of pyridinium p-toluenesulfonate were added, and the resultant mixture was stirred overnight at ambient temperature. The solvents were removed in vacuo; the residue was taken up in ethyl acetate and filtered through a pad of diatomaceous earth. The solvents were removed in vacuo, and the residue was dissolved in 1 mL of dimethylformamide. 1-(Trimethylsilyl)imidazole (100 mg) was added, and the solution was warmed to 50° C. for 3 hours. Solvents were removed in vacuo, and the residue was purified by chromatography on an Analogix Intelliflash 280™, eluting with a gradient from 10% to 40% ethyl acetate in hexanes to provide the titled compound (72 mg, 79%).

Example 15E (1R,3R,7E,17β)-17-[(1R,4R)-5-hydroxy-1,4,5-trimethylhexyl]-9,10-secoestra-5,7-diene-1,3-diol Note: The following sequence was performed in a darkened hood. The compound of Example 9A (57 mg, 0.1 mmol) was combined with the compound of Example 15D (36 mg, 0.1 mmol) in 1 mL of toluene; the solvent was removed in vacuo to dry the reagents thoroughly. The residue was taken up in 1.5 mL of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. An additional 0.05 mL of the lithium bis(trimethylsilyl)amide reagent was added; the resultant mixture was stirred at −78° C. for 1 hour, then warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was dissolved in 1 mL of 1 N tetra-n-butylammonium fluoride in tetrahydrofuran. After warming at 50° C. for 5 hours, the reaction mixture was partitioned between ethyl acetate and water. The organic phase was washed with brine and dried over $Na_2SO_4$. The solvents were removed in vacuo, and the residue was purified by chromatography on an Analogix IntelliFlash 280™, eluting with a gradient from 0% to 100% ethyl acetate in hexanes, followed by a solvent hold at 100% ethyl acetate to provide the titled compound (13 mg). $^1H$ NMR (500 MHz, $CD_2Cl_2$) δ ppm 6.28 (d, J=11.3 Hz, 1 H) 5.86 (d, J=11.3 Hz, 1 H) 3.90-4.15 (m, 2 H) 2.75-2.87 (m, 1 H) 2.75-2.86 (m, 1 H) 2.67 (dd, J=13.1, 4.0 Hz, 1 H) 2.45 (dd, J=13.1, 3.4 Hz, 1 H) 2.10-2.26 (m, 2 H) 1.97-2.06 (m, 2 H) 1.81-1.94 (m, 2 H) 1.43-1.81 (m, 9 H) 1.23-1.39 (m, 3 H) 1.06-1.20 (m, 8 H) 0.81-1.00 (m, 9 H) 0.55 (s, 3 H); MS (+DCI) m/z 436 $(M+NH_4)^+$.

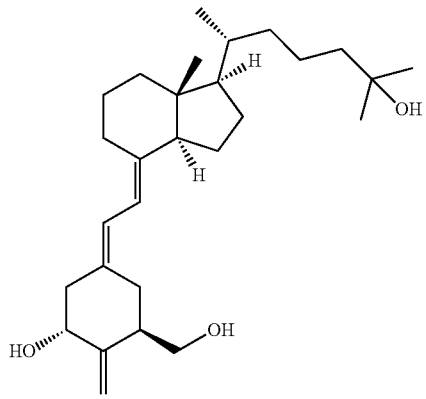 [SMILES: C=C1[C@H](CO)C/C(=C\C=C2/CCC[C@]3(C)[C@@H]([C@H](C)CCCC(C)(C)O)CC[C@@H]23)C[C@H]1O]

Example 16

(1R,3R,5E,7E,17β)-17-[(1R)-5-hydroxy-1,5-dimethylhexyl]-3-(hydroxymethyl)-2-methylene-9,10-secoestra-5,7-dien-1-ol

Example 16A (1R,2R,4R,6S)-4-isopropenyl-1-methyl-7-oxabicyclo[4.1.0]heptan-2-ol (S)-Carvone oxide (75.7 g, 455 mmol; prepared by procedure described by Klein and Ohloff in Tetrahedron 1963, 19, 1091-1099) was dissolved in 750 mL of tetrahydrofuran and cooled to −78° C. L-Selectride® (1 M in tetrahydrofuran, 708 mL, 708 mmol) was added over 71 minutes. After stirring an additional 4 hours, the reaction was quenched by the addition of 250 mL of methanol, and then warmed to ambient temperature overnight. The mixture was refluxed (about 63° C.) for 7 hours, and then cooled to ambient temperature and stirred overnight (16.5 hours including cooling). The mixture was concentrated in vacuo and chased with 250 mL of methanol. The crude product was washed twice with 300 mL of water. The combined aqueous washes were extracted three times with 250 mL each of tert-butyl methyl ether. The tert-butyl methyl ether extracts and another 500 mL of tert-butyl methyl ether were added to the crude product. The tert-butyl methyl ether solution was washed three times with 100 mL of water, once with 275 mL of brine, and then dried over $MgSO_4$. After filtration, the solution was concentrated in vacuo, dissolved in 450 mL of tetrahydrofuran and cooled to 3° C. 300 mL of 10% NaOH solution was added followed by 300 mL of 30% $H_2O_2$ solution. The resulting solution was stirred overnight at ambient temperature. After the two resulting layers were separated, 500 mL of tetrahydrofuran was added to the organic layer. The tetrahydrofuran solution was then washed twice with 250 mL of 18% aqueous $NaHSO_3$ solution. Tetrahydrofuran was removed in vacuo, and 1000 mL of tert-butyl methyl ether was added to the concentrate. The tert-butyl methyl ether solution was washed three times with 100 mL of water, then with 300 mL of brine, and dried over $MgSO_4$. The $MgSO_4$ was filtered off and the filtrate was concentrated to dryness under high vacuum. The product was purified on a 2.0 kg of Silica Gel 60 column with hexanes: tert-butyl methyl ether (from 4:1 to 13:7), to afford the titled compound (11.1 g, 14.5%).

Example 16B tert-butyl{[(1S,2R,4S,6S)-4-isopropenyl-1-methyl-7-oxabicyclo[4.1.0]hept-2-yl]oxy}dimethylsilane The compound of Example 16A (11.0 g, 65 mmol) in 66 mL of dimethylformamide was treated with 5.37 g (1.2 equivalents) of imidazole followed by 11.2 g (1.14 equivalents) of tert-butyldimethylsilyl chloride. The reaction was stirred for 20 hours at ambient temperature. The reaction solution was mixed with 200 mL of water and the resulting layers were separated. The aqueous layer was extracted three times with 120 mL each of tert-butyl methyl ether. The organic layers were combined, and washed twice with 125 mL each of 10% aqueous NaCl. The tert-butyl methyl ether solution was dried over MgSO$_4$ then filtered and concentrated in vacuo. The product was purified on 2.00 kg of Silica Gel 60 with a gradient of hexanes:tert-butyl methyl ether from 19:1 (8 L) to 9:1 (4 L) to afford 16.2 the titled compound (16.2 g, 91 %).

Example 16C (1S,3S,5R,6S)-5-{[tert-butyl(dimethyl)silyl]oxy}-6-methyl-7-oxabicyclo[4.1.0]hept-3-yl acetate The compound of Example 16B (14.0 g, 50 mmol) was dissolved in 405 mL of dichloromethane and 85 mL of methanol; 2.15 g (25.6 mmol, 0.52 equivalents) of NaHCO$_3$ was added. The mixture was cooled below −70° C., and O$_3$ was bubbled through the reaction mixture until it remained blue (about 35 minutes). Excess O$_3$ was removed by bubbling N$_2$ through the reaction mixture at below −70° C. until it turned colorless. The reaction mixture was warmed to ambient temperature; the solid NaHCO$_3$ was filtered off and rinsed with 60 mL of dichloromethane. The combined filtrate and rinses were concentrated to a viscous oil, which was chased with 425 mL of benzene to remove residual methanol. The resulting oil was dissolved in 400 mL of dichloromethane and 80 mL of pyridine. The solution was cooled to −10° C. and 4-nitrobenzoyl chloride (11.6 gm, 61.4 mmol, 1.24 equivalents) dissolved in 80 mL of dichloromethane was added to the solution over 10 minutes. The temperature was maintained at below −6° C. during the addition. The reaction solution was cooled to below −10° C. and stirred at this temperature overnight. The reaction solution was warmed up to 44° C. and stirred for 3 hours. After cooling to ambient temperature, the reaction was concentrated in vacuo and the residue was dissolved in 600 mL of ethyl acetate. The ethyl acetate solution was washed four times with 100 mL of water, and then concentrated to a thick slurry which was triturated with 100 mL of hexanes. The solids were filtered off and washed three times with 65 mL each of hexanes. The combined hexane filtrate and washes were concentrated and filtered. 400 mL of Hexanes were added to the filtrate; the resultant solution was washed three times with 100 mL of water, then with 100 mL of 10% NaCl, dried over MgSO$_4$, filtered and concentrated. The resulting crude material was purified on 2.00 kg of Silica Gel 60 using hexanes:tert-butyl methyl ether=9:1 (24.0 L) to afford the titled compound (8.35 g, 56%).

Example 16D (1S,3S,5R,6S)-5-{[tert-butyl(dimethyl)silyl]oxy}-6-methyl-7-oxabicyclo[4.1.0]heptan-3-ol The compound of Example 16C (9.20 g, 30.6 mmol) was dissolved in 105 mL of methanol. K$_2$CO$_3$ (10.1 g, 72.1 mmol, 2.35 equivalents) was added and the reaction mixture was stirred at ambient temperature for 2 hours. 6.60 mL (115 mmol, 3.77 equivalents) of acetic acid were added to the reaction mixture; after mixing for 10 minutes, the solids were filtered off and rinsed with 40 mL of methanol. The combined filtrate and rinses were concentrated to a residue which was mixed with 106 mL of water. The layers were separated, and the aqueous layer was extracted three times with 50 mL of ethyl acetate. The combined organic layers were washed twice with 45 mL of brine, dried over MgSO$_4$, filtered and concentrated to afford the titled compound (7.72 g, 98%).

Example 16E tert-butyl(dimethyl)({(1S,2R,4S,6S)-1-methyl-4-[(triethylsilyl)oxy]-7-oxabicyclo[4.1.0]hept-2-yl}oxy)silane The compound of Example 16D (4.71 g, 18.2 mmol) and imidazole (1.76 g, 25.6 mmol, 1.4 equivalents) were dissolved in 36 mL of dimethylformamide. Then chlorotriethylsilane (3.34 g, 21.9 mmol) was added, and the reaction was stirred at ambient temperature for 2 hours. 125 mL of Water was added to the reaction mixture. Two layers of liquors were obtained and about 6 g of upper layer was separated. Then the lower aqueous layer was extracted three times with 100 mL each of tert-butyl methyl ether. The combined organic layers were washed with 125 mL of 10% aqueous NaCl, dried over MgSO$_4$, filtered and concentrated in vacuo to afford the titled compound (6.71 g, 99%).

Example 16F (1S,3R,5S)-3-{[tert-butyl(dimethyl)silyl]oxy}-2-methylene-5-[(triethylsilyl)oxy]cyclohexanol Tetramethylpiperidine (9.66 g, 67.7 mmol) was dissolved in 76 mL of benzene and cooled below 0° C. n-Butyllithium (2.5 M in hexane, 27.5 mL, 68.8 mmol) was added to the benzene solution below 2.5° C. The resulting solution was stirred below 0° C. Et$_2$AlCl (1.8 M in toluene, 39 mL, 70.2 mmol) was added to the reaction below 3° C. followed by a rinse of 5.0 mL of benzene. The resulting solution was stirred at below 0° C. for 30 minutes. The compound of Example 16E (6.36 g, 17.1 mmol) dissolved in 25 mL of benzene was added to the reaction solution at below 1° C. over 10 minutes. 5.0 mL of Benzene was used as a rinse. The reaction was stirred at below 0° C. for 2.7 hours. The reaction mixture was quenched into 441 g of 17.2 wt % NH$_4$Cl solution (cooled to below 5° C.). 104 g of 10 wt % HCl solution was slowly added to the mixture, and pH was adjusted to 2.0. The layers were separated and the aqueous layer was extracted four times with 100 mL of ethyl acetate. The combined organic layers were washed three times with 100 mL of water, then 100 mL of 7.8 wt % NaHCO$_3$, and 100 mL of brine, and then dried over MgSO$_4$. Filtration and concentration in vacuo yielded the title compound (6.13 g, 96%).

Example 16G tert-butyl({(1R,5S)-2-(iodomethyl)-5-[(triethylsilyl)oxy]cyclohex-2-en-1-yl}oxy)dimethylsilane The compound of Example 16F (2.76 g, 7.4 mmol) and 4-dimethylaminopyridine (1.35 g, 11.1 mmol) were dissolved in 74 mL of dichloromethane and cooled to 0° C. Methanesulfonyl chloride (0.72 mL, 9.25 mmol) was added, and the reaction was stirred at ambient temperature for 4.5 hours. After dilution with additional dichloromethane, the reaction mixture was washed twice with 10% NaCl, then dried over $MgSO_4$, filtered and concentrated in vacuo. The residue was dissolved in 74 mL acetone, and $NaHCO_3$ (0.5 g), $Na_2SO_3$ (0.5 g) and NaI (4.5 g, 30 mmol) were added. The reaction was heated to 55° C. for 90 minutes, and then stirred overnight at ambient temperature. The mixture was diluted with 500 mL of tert-butyl methyl ether, washed twice with 250 mL of 8:1:1 10% NaCl:1 N $NaHCO_3$:1 M $Na_2SO_3$, then with brine. The resulting solution was dried over $MgSO_4$, filtered and concentrated in vacuo. Purification by silica gel chromatography (300 mL of $SiO_2$, elution with 1:1 dichloromethane:hexanes) afforded the title compound (2.52 g, 70%).

Example 16H (1S,3R,5R)-3-{[tert-butyl(dimethyl)silyl]oxy}-5-(hydroxymethyl)-4-methylenecyclohexanol The compound of Example 16G (2.5 g, 5.2 mmol) was dissolved in 20 mL of water and 30 mL of tetrahydrofuran. Indium powder (0.90 g) was added followed by formaldehyde (37% aqueous solution, 1.6 mL, 21 mmol). Two additional portions of indium (0.3 g each) were added to drive the reaction toward completion. The reaction was diluted with 180 mL of water and extracted twice with 250 mL each of ethyl acetate. The combined organic layers were washed sequentially with 5% $NaHCO_3$ and brine, then dried over $MgSO_4$, filtered and concentrated in vacuo. Purification by silica gel chromatography (200 mL of $SiO_2$, elution with a gradient of 1:1 to 3:1 ethyl acetate:hexanes) afforded the titled compound (0.97 g, 68%).

Example 16I (1S,3R,5R)-3-{[tert-butyl(dimethyl)silyl]oxy}-5-({[tert-butyl(dimethyl)silyl]oxy}methyl)-4-methylenecyclohexanol The compound of Example 16H (574 mg, 2.1 mmol) was dissolved in 35 mL of dichloromethane and tert-butyldimethylsilylimidazole (0.54 mL, 2.8 mmol) was added. After stirring overnight, the reaction was diluted with dichloromethane and washed twice with 10% NaCl, then dried over $MgSO_4$, filtered and concentrated in vacuo. After a second run using 340 mg of the starting diol, the combined unpurified product mixtures were purified by silica gel chromatography (200 mL of $SiO_2$, elution with a gradient of 1:4 ethyl acetate:hexanes to ethyl acetate) to afford the titled compound (940 mg) contaminated with a small amount of a regioisomeric bis-TBS ether.

Example 16J (3R,5R)-3-{[tert-butyl(dimethyl)silyl]oxy}-5-({[tert-butyl(dimethyl)silyl]oxy}methyl)-4-methylenecyclohexanone The compound of Example 16I (0.93 g, 2.4 mmol) was dissolved in 30 mL of dichloromethane and treated with 1.02 g (2.4 mmol) of Dess-Martin periodinane. After 2.5 hours, the reaction was diluted with additional dichloromethane and washed with 100 mL of 4:1 1 M $NaHCO_3$:1 M $Na_2SO_3$, then 100 mL of 9:1 20% NaCl:1 M $NaHCO_3$. The organic layer was dried over $MgSO_4$, filtered and concentrated in vacuo, then purified by silica gel chromatography (200 mL of $SiO_2$, elution with 1:4 ethyl acetate:hexanes) to afford the titled compound (794 mg, 85%).

Example 16K ethyl (2E)-[(3R,5R)-3-{[tert-butyl(dimethyl)silyl]oxy}-5-({[tert-butyl(dimethyl)silyl]oxy}methyl)-4-methylenecyclohexylidene]acetate n-Butyllithium (2.5 M in hexanes, 1.6 mL, 4 mmol) was added to a solution of diisopropylamine (0.56 mL, 4 mmol) in 5 mL of tetrahydrofuran at −78° C. After 30 minutes, ethyl trimethylsilylacetate (0.73 mL, 4 mmol) was added. After stirring 30 minutes, a solution of the compound of Example 16J (787 mg, 2 mmol) in 8 mL of tetrahydrofuran was added, followed by a rinse of 2 mL of tetrahydrofuran. After 2 hours, the reaction was quenched by the addition of 10 mL of saturated aqueous $NH_4Cl$. After warming to ambient temperature, the mixture was poured into 100 mL of 20% NaCl, then extracted twice with 100 mL of tert-butyl methyl ether. The combined tert-butyl methyl ether extracts were dried over $MgSO_4$, filtered and concentrated in vacuo. The residue was purified by silica gel chromatography (300 mL of $SiO_2$, elution with a gradient of 1:1 dichloromethane:hexanes to dichloromethane) to afford 538 mg (58% yield) of a ~4:1 mixture of isomers favoring the title compound (538 mg, 58%).

Example 16L (2E)-2-[(3R,5R)-3-{[tert-butyl(dimethyl)silyl]oxy}-5-({[tert-butyl(dimethyl)silyl]oxy}methyl)-4-methylenecyclohexylidene]ethanol The compound of Example 16K (589 mg, 1.3 mmol) was dissolved in 20 mL of toluene and 10 mL of dichloromethane and cooled in a dry ice/acetone bath. Diisobutylaluminum hydride (1 M in hexanes, 5.8 mL, 5.8 mmol) was added dropwise. After 1 hour, the reaction was quenched by the addition of 20 mL of 20% aqueous sodium potassium tartrate. To this mixture was added 25 mL of water followed by 6 mL of 2 N HCl. The resulting mixture was extracted three times with dichloromethane. The combined extracts were washed with 10% aqueous NaCl, dried over $MgSO_4$, filtered and concentrated in vacuo. Purification by silica gel chromatography (70 mL of $SiO_2$, elution with dichloromethane) afforded the titled compound (294 mg, 55%), contaminated with ~20% of an olefin isomer.

Example 16M

{(2E)-2-[(3R,5R)-3-{[tert-butyl(dimethyl)silyl]oxy}-5-({[tert-butyl(dimethyl)silyl]oxy}methyl)-4-methylenecyclohexylidene]ethyl}(diphenyl)phosphine oxide n-Butyllithium (2.5 M in hexanes, 0.62 mL, 1.55 mmol) was added to a solution of diphenylphosphine (0.30 mL, 1.73 mmol) in 3 mL of tetrahydrofuran at 0° C., creating a solution of lithium diphenylphosphide.

The compound of Example 16L (241 mg, 0.58 mmol) was dissolved in 6.2 mL tetrahydrofuran at 0° C. n-Butyllithium (2.5 M in hexanes, 0.24 mL, 0.61 mmol) was added, followed by a solution of toluenesulfonyl chloride (124 mg, 0.65 mmol) in 3 mL of tetrahydrofuran. The lithium diphenylphosphide solution was added dropwise until a red color persisted. After stirring for an additional 1 hour, the reaction was quenched with water, and then concentrated in vacuo. The residue was dissolved in 12 mL of dichloromethane, and 10% aqueous hydrogen peroxide (3 mL) was added at 0° C. After 1 hour, the reaction was poured into cold 1 M $Na_2SO_3$ and extracted twice with dichloromethane. The combined organic layers were washed with 20% aqueous NaCl, dried over $MgSO_4$, filtered and concentrated in vacuo. Purification by silica gel chromatography (120 mL of $SiO_2$, eluting with a gradient of 1:4 to 1:1 ethyl acetate:hexanes) afforded the titled compound (250 mg, 72%).

Example 16N (1R,3R,5E,7E,17β)-17-[(1R)-5-hydroxy-1,5-dimethylhexyl]-3-(hydroxymethyl)-methylene-9,10-secoestra-5,7-dien-1-ol Note: The following sequence was performed in a darkened hood. The compound of Example 16M (40 mg, 0.07 mmol) was combined with the compound of Example 13J (32 mg, 0.09 mmol) in 1 mL of toluene; the solvent was removed in vacuo to dry the reagents thoroughly. The residue was taken up in 1.5 ml of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. An additional 0.05 mL of the lithium bis(trimethylsilyl)amide reagent was added; the resultant mixture was stirred at −78° C. for 1 hour, then warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was dissolved in 1 mL of 1 N tetra-n-butylammonium fluoride in tetrahydrofuran. After warming at 50° C. for 4.5 hours, the reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 10% to 100% ethyl acetate in hexanes, followed by a solvent hold at 100% ethyl acetate to afford the titled compound (10.2 mg). $^1$H NMR (500 MHz, $CD_2Cl_2$) δ ppm 6.20 (d, J=11.3 Hz, 1 H) 6.04 (d, J=11.0 Hz, 1 H) 5.10 (s, 1 H) 4.88 (s,1 H) 4.21 (dd, J=7.6, 4.6 Hz, 1 H) 3.49-3.72 (m, 2 H) 2.59-2.73 (m, 1 H) 2.57 (dd, J=12.8, 4.6 Hz, 1 H) 2.43-2.52 (m, 2 H) 2.31 (dd, J=13.6, 6.6 Hz, 1 H) 2.23 (dd, J=12.8, 7.9 Hz, 1 H) 2.06-2.18 (m, 2 H) 1.81-1.93 (m, 1 H) 1.66-1.77 (m, 2 H) 1.55-1.66 (m, 6 H) 1.44-1.54 (m, 2 H) 1.31-1.44 (m, 5 H) 1.22-1.31 (m, 3 H) 1.13-1.22 (m, 9 H) 0.92-0.97 (m, 3 H); MS (+DCI) m/z 449 $(M+NH_4)^+$.

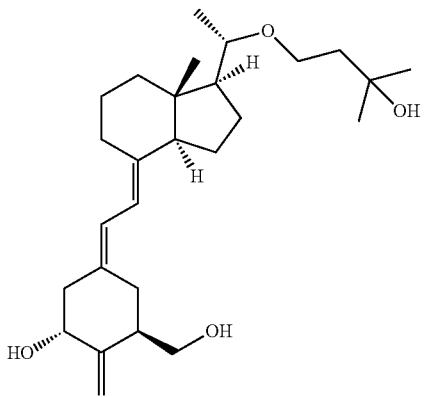 [SMILES: C=C1[C@H](CO)C/C(=C\C=C2/CCC[C@]3(C)[C@@H]([C@H](C)OCCC(C)(C)O)CC[C@@H]23)C[C@H]1O]

Example 17

(1R,3R,5E,7E,17β)-3-(hydroxymethyl)-17-[(1S)-1-(3-hydroxy-3-methylbutoxy)ethyl]-2-methylene-9,10-secoestra-5,7-dien-1-ol Note: The following sequence was performed in a darkened hood. The compound of Example 16M (40 mg, 0.07 mmol) was combined with the compound of Example 8G (35 mg, 0.1 mmol) in 1 mL of toluene; the solvent was removed in vacuo to dry the reagents thoroughly. The residue was taken up in 1.5 mL of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. An additional 0.05 mL of the lithium bis(trimethylsilyl)amide reagent was added; the resultant mixture was stirred at −78° C. for 1 hour, then warmed to 0° C. and stirred at this temperature for 30 minutes. The reaction was quenched by addition of 1 mL of 1 N aqueous $NH_4Cl$, and the mixture was extracted with ethyl acetate. The organic extract was washed with brine and dried over $Na_2SO_4$. The solvents were removed in vacuo, and the residue was dissolved in 1 mL of 1 N tetra-n-butylammonium fluoride in tetrahydrofuran. After warming at 50° C. for 5 hours, the reaction mixture was partitioned between ethyl acetate and water. The organic phase was washed with brine and dried over $Na_2SO_4$. The solvents were removed in vacuo, and the residue was purified by chromatography on an Analogix Intelliflash 280™, eluting with a gradient from 10% to 100% ethyl acetate in hexanes, followed by a solvent hold at 100% ethyl acetate to afford the titled compound (5 mg). $^1$H NMR (500 MHz, $CD_2Cl_2$) δ ppm 6.26 (d, J=11.3 Hz, 1 H) 5.86 (d, J=11.3 Hz, 1 H) 5.11 (s,1 H) 4.91 (s,1 H) 4.20 (dd, J=7.9, 4.9 Hz, 1 H) 3.74-3.90 (m, 1 H) 3.49-3.68 (m, 2 H) 3.42-3.51 (m, 2 H) 3.40-3.52 (m, 2 H) 3.26 (dd, J=7.9, 6.1 Hz, 1 H) 3.26 (dd, J=7.9, 6.1 Hz, 1 H) 2.82 (dd, J=12.2, 4.0 Hz, 1 H) 2.63-2.70 (m, 1 H) 2.58 (dd, J=12.8, 4.6 Hz, 1 H) 2.32-2.46 (m, 2 H) 2.22 (dd, J=12.4, 8.4 Hz, 2 H) 1.98-2.08 (m, 2 H) 1.63-1.76 (m, 6 H) 1.53-1.64 (m, 6 H) 1.10-1.24 (m, 9 H); MS (+DCI) m/z 450 $(M+NH_4)^+$.

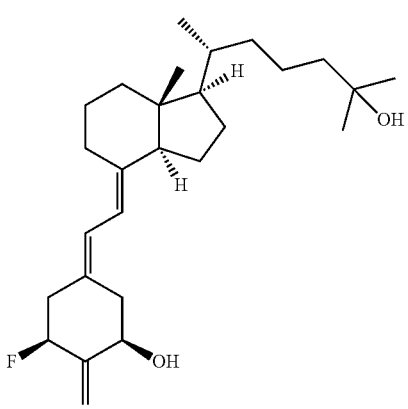 [SMILES: C=C1[C@H](O)C/C(=C\C=C2/CCC[C@]3(C)[C@@H]([C@H](C)CCCC(C)(C)O)CC[C@@H]23)C[C@@H]1F]

Example 18

(1R,3S,5E,7E,17β)-3-fluoro-17-[(1R)-5-hydroxy-1,
5-dimethylhexyl]-2-methylene-9,10-secoestra-5,7-
dien-1-ol

Example 18A methyl (2Z)-((3R,5R)-3-{[tert-butyl(diphenyl)silyl]
oxy}-5-hydroxy-4-methylenecyclohexylidene)ac-
etate A solution of diisopropylamine (1.2 mL, 9.4 mmol) in 10 mL of tetrahydrofuran was cooled to −78° C.; n-butyllithium (2.5 M in hexanes, 3.6 mL) was added, followed after 5 minutes by methyl trimethylsilylacetate (1.7 mL). The resultant solution was stirred at −78° C. for 30 minutes, and then a solution of the compound of Example 13E (2.0 g, 4 mmol) in 10 mL of tetrahydrofuran was added over 5 minutes. Stirring was continued for 4 hours. The reaction was quenched by addition of saturated aqueous NH$_4$Cl; the mixture was warmed to ambient temperature, and partitioned between ethyl acetate and water. The organic phase was washed with 1 N aqueous HCl and brine, and dried over Na$_2$SO$_4$. The solvents were removed in vacuo; the residue was purified by chromatography on an Analogix Intelliflash 280™, eluting with a gradient of 5% to 10% ethyl acetate in hexanes. The product (1.9 g) was dissolved in 17 mL of ethanol; 1.3 mL of concentrated HCl was added, and the resultant solution was stirred overnight at ambient temperature. The solvents were removed in vacuo, the residue was taken up in saturated aqueous sodium bicarbonate solution and extracted with ethyl acetate. The organic phase was concentrated in vacuo and purified by chromatography on an Analogix Intelliflash 280™, eluting with a gradient of 2% to 3% dichloromethane in acetonitrile to afford the titled compound (0.76 g).

Example 18B methyl (2E)-((3R,5S)-3-{[tert-butyl(diphenyl)silyl]
oxy}-5-fluoro-4-methylenecyclohexylidene)acetate The compound of Example 18A (600 mg, 0.23 mmol) was dissolved in 2.4 mL of dichloromethane, and the resultant solution was cooled to −78° C. (Diethylamino)sulfur trifluoride (DAST, 0.6 mL) was added; the mixture was stirred for 30 minutes, and then quenched by addition of saturated aqueous sodium bicarbonate solution. The mixture was warmed to ambient temperature; the organic phase was dried over Na$_2$SO$_4$. The solvents were removed in vacuo; the residue was purified by chromatography on an Analogix IntelliFlash 280™, eluting with a gradient of 5% to 7% ethyl acetate in hexanes, to give the titled compound, plus some mixed fractions.

Example 18C (2E)-2-((3R,5S)-3-{[tert-butyl(diphenyl)silyl]oxy}-
5-fluoro-4-methylenecyclohexylidene)ethanol The compound of Example 18B (130 mg, 0.3 mmol) was dissolved in 1 mL of 1:1 dichloromethane/toluene and cooled to −78° C. Diisobutylaluminum hydride (1 M in hexanes, 0.7 mL, 2.5 equivalents) was added, and the mixture was stirred for 30 minutes. Reaction was quenched by the addition of methanol, followed by saturated aqueous NH$_4$Cl; the mixture was warmed to ambient temperature and extracted with ethyl acetate. The organics were washed with brine and dried over Na$_2$SO$_4$. The solvents were removed in vacuo; the residue was purified by chromatography on an Analogix Intelliflash 280™, eluting with 15% ethyl acetate in hexanes, to give the titled compound (111 mg, 95%).

Example 18D

[(2E)-2-((3R,5S)-3-{[tert-butyl(diphenyl)silyl]oxy}-
5-fluoro-4-methylenecyclohexylidene)ethyl](diphe-
nyl)phosphine oxide The compound of Example 18C (110 mg, 0.27 mmol) was dissolved in 2 mL of hexanes; 54 mg (0.18 mmol) of triphosgene was added, and the mixture was cooled to 0° C. Triethylamine (0.14 mL, 0.95 mmol) was added dropwise over 2 minutes; the reaction mixture was stirred for 30 minutes, and then warmed to ambient temperature over 1 hour. Additional hexanes (3 mL) were added, and the reaction mixture was washed sequentially with cold 3% aqueous HCl, water, and brine. The organic phase was dried over Na$_2$SO$_4$; the solvents were removed in vacuo.

Diphenylphosphine (0.51 g) was dissolved in 2 mL of tetrahydrofuran, and the solution was cooled to 0° C. A solution of n-butyllithium (2.5 M in hexanes, 0.85 mL) was added, and the mixture was stirred for 5 minutes. In the meantime, the above intermediate allylic chloride was dissolved in 1 mL of tetrahydrofuran and cooled to −60° C. The anion solution was added over 5 minutes, and the resultant mixture was stirred at −60° C. for 1 hour. The reaction was quenched with water; the mixture was warmed to ambient temperature and extracted with ethyl acetate. The organic phase was washed with 1 N aqueous HCl and brine, and dried over Na$_2$SO$_4$. The solvents were removed in vacuo; the residue was purified by chromatography on an Analogix Intelliflash 280™, eluting with a gradient of 40% to 50% ethyl acetate in hexanes to afford the titled compound (160 mg, 76%).

Example 18E (1R,3S,5E,7E, 17β)-3-fluoro-17-[(1R)-5-hydroxy-1,
5-dimethylhexyl]-2-methylene-9,10-secoestra-5,7-
dien-1-ol Note: The following sequence was performed in a darkened hood. The compound of Example 18D (15 mg, 0.026 mmol) was combined with the compound of Example 13J (13 mg, 0.06 mmol) in 1 mL of toluene; the solvent was removed in vacuo to dry the reagents thoroughly. The residue was taken up in 1 mL of dry tetrahydrofuran and cooled to −78° C. A solution of lithium bis(trimethylsilyl)amide (1.0 M in tetrahydrofuran; 0.1 mL) was added dropwise, producing a yellow-orange color that fades over 20 minutes. The resultant mixture was stirred at −78° C. for 1 hour, then warmed to 0° C. and stirred at this temperature for 30 minutes. The reaction was quenched by addition of 1 mL of 1 N aqueous NH$_4$Cl, and the mixture was extracted with ethyl acetate. The organic extract was washed with brine and dried over Na$_2$SO$_4$. The solvents were removed in vacuo, and the residue was dissolved in 1 mL of 1 N tetra-n-butylammonium fluoride in tetrahydrofuran. After stirring overnight at ambient temperature, the reaction mixture was partitioned between ethyl acetate and water. The organic phase was washed with brine and dried over Na$_2$SO$_4$. The solvents were removed in vacuo, and the residue was purified by chromatography on an Analogix IntelliFlash 280™, eluting with a gradient from 20% to 27% ethyl acetate in hexanes to afford the titled compound (4 mg). $^1$H NMR (500 MHz, CD$_2$Cl$_2$) δ ppm 6.32 (d, J=11.3 Hz, 1 H) 6.08 (d, J=11.3 Hz, 1 H) 5.14-5.25 (m, 2 H) 4.75-5.01 (m, 1 H) 2.88 (dd, J=13.1, 4.6 Hz, 1 H) 2.61-2.75 (m, 1 H) 2.36-2.55 (m, 3 H) 2.13-2.27 (m, 3 H) 2.00 (s, 2 H) 1.81-1.91 (m, 2 H) 1.67-1.79 (m, 2 H) 1.56-1.67 (m, 4 H) 1.45-1.56 (m, 6 H) 1.35-1.45 (m, 2 H) 1.11-1.26 (m, 9 H) 0.84-0.92 (m, 3 H).

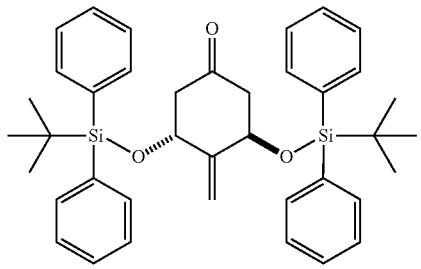

Example 19

(3R,5R)-3,5-Bis{[tert-butyl(diphenyl)silyl]oxy}-4-methylenecyclohexanone

Example 19A (1R,4R,6R)-4-Isopropenyl-1-methyl-7-oxabicyclo[4.1.0]heptan-2-one (R)-Carvone was epoxidized according to a modification of the method of E. Klein and G. Ohloff (*Tetrahedron*, 1963, 11, 1091-1099). Thus H$_2$O$_2$ (31%, 95 mL, 836 mmol, 1.3 equivalents) was added to a solution of (L)-carvone (100 mL, 640 mmol) in 650 mL of methanol at <5° C. After cooling to <0° C., 6N NaOH (10.5 mL, 63 mmol, 0.1 equivalents) was added. The reaction temperature was maintained at <5° C. After 5 hours, the reaction was diluted with 650 mL water, then quenched with 0.5 N KH$_2$PO$_4$ (250 mL) and 325 mL of 1 molal Na$_2$SO$_3$, keeping the temperature at <25° C. The reaction was extracted with 2×750 mL tert-butyl methyl ether. The combined tert-butyl methyl ether extracts were washed with 500 mL each of 20% aqueous NaCl then 10% then 25% to provide a clear organic layer which was dried over MgSO$_4$, then filtered and concentrated, then chased with 100 mL of methanol. The resulting solution assayed (GC) at 101.3 g (96%) of the titled compound, which contained 5% of the minor isomer. $^1$H NMR (400 MHz, CDCl$_3$) δ ppm 1.40 (s, 3 H) 1.70 (s, 3 H) 1.89 (ddd, J=14.75, 11.11, 1.17 Hz, 1 H) 2.02 (dd, J=17.56, 11.66 Hz, 1 H) 2.31 -2.41 (m, 1 H) 2.58 (ddd, J=17.56, 4.67, 1.37 Hz, 1 H) 2.65-2.76 (m, 1 H) 3.44 (dd, J=3.09, 1.03 Hz, 1 H) 4.70 (d, J=0.69 Hz, 1 H) 4.75-4.80 (m, 1 H).

Example 19B (1S,2R,4S,6R)-4-Isopropenyl-1-methyl-7-oxabicyclo[4.1.0]heptan-2-ol

A solution of CeCl$_3$·7H$_2$O (128 g, 343 mmol, 0.5 equivalents) in 1.5 L of methanol was cooled to <0° C. Example 19A (47 wt % solution in methanol, 242 g, 685 mmol) was added, and rinsed in with 60 mL of methanol. After cooling to <−20° C., NaBH$_4$ (2 M in triglyme, 190 mL, 380 mmol, 0.55 equivalents) was added over 23 minutes, maintaining the temperature <−20° C. After stirring an additional 25 minutes, the reaction was quenched with 720 mL of water. The methanol was removed by distillation, and 800 mL of isopropyl acetate was added. 2N HCl (100 mL) was added to bring the pH to ~5.5, after which layers were separated, and the aqueous layer was extracted with 400 mL of isopropyl acetate. The combined isopropyl acetate layers were washed with 500 mL of 5% NaCl, then 525 mL of 19:1 10% NaCl:10% NaHCO$_3$, then 500 mL of 20% NaCl. The organic solution was then dried over MgSO$_4$, filtered and concentrated to provide 193 g of an oil that assayed to 54.7 wt % (105.6 g assay, 92% yield) of the titled product.

Example 19C tert-butyl{[(1R,2R,4R,6R)-4-isopropenyl-1-methyl-7-oxabicyclo[4.1.0]hept-2-yl]oxy}diphenylsilane To a solution of Example 19B (54.7 wt %, 18.4 g, 60 mmol) and imidazole (6.94 g, 102 mmol, 1.7 equivalents) in 100 mL of dimethylformamide was added TBDPS-Cl (23.4 mL, 90 mmol, 1.5 equivalents). The reaction was stirred for 90 hours, and then cooled in an ice/water bath. Water (3 mL) was added, the bath was removed and the reaction was stirred for 15 minutes. The reaction was transferred to a separatory funnel with 110 mL of heptane and 55 mL of water, shaken and separated. More water (25 mL) was added to the aqueous layer, which was further extracted with 2×50 mL of heptane. The combined heptane extracts were washed with 2×100 mL of 10% NaCl, then dried over MgSO$_4$, filtered and concentrated in vacuo.

Chromatography (Isco CombiFlash® system, Analogix RS300 300 g column, 80:20 hexane:CH$_2$Cl$_2$ for 10 minutes, then 65:35 for 25 minutes, then 60:40 for 10 minutes) yielded 26.1 g of an oil that assayed to 83 wt % against a standard (21.6 g assay, 89% yield) of the titled compound.

Example 19D (1R,3R,5R,6R)-5-{[tert-butyl(diphenyl)silyl]oxy}-6-methyl-7-oxabicyclo[4.1.0]heptan-3-ol A mixture of Example 19C (34 g, 92 wt %, 77 mmol) and NaHCO$_3$ (3.3 g, 39 mmol, 0.5 equivalents) in 300 mL of CH$_2$Cl$_2$ and 60 mL of methanol was cooled to <−70° C. and treated with ozone (7-8 psi, 90 volts, 4 slpm) until a persistent blue color was observed. After purging with nitrogen until the color was removed, the reaction was warmed to ~0° C., then filtered through paper and concentrated.

After chasing with 2×100 mL of benzene, 300 mL of CH$_2$Cl$_2$ and 60 mL of pyridine were added and the reaction was cooled to <5° C. p-Nitrobenzoyl chloride (22.2 g, 120 mmol, 1.5 equiv.) was added, and the reaction mixture was stirred for 1 hour, then the bath was removed and the reaction stirred at ambient temperature overnight. The resulting suspension was concentrated on a rotovap to a thick slurry, and then diluted with ethyl acetate, and the solids were removed by filtration. The filtrate was washed with 250 mL of 1 molal NaHCO$_3$, then with 100 mL each of 2N HCl, 1 N HCl, and 2N HCl, and with 200 mL each of 1 N HCl, 1 molal NaHCO$_3$, and 20% NaCl. The organic layer was dried over MgSO$_4$, filtered and concentrated to yield 49.6 g of the acetate intermediate as an oil.

To a solution of acetate (20.6 g, 32 mmol theory) in 115 mL of methanol and 15 mL of water was added 11.0 g of K$_2$CO$_3$. After 2 hours, the reaction was quenched with 6.5 mL of HOAc, then concentrated. The residue was treated with 100 mL of water, and then extracted with 150 mL of ethyl acetate then 100 mL of ethyl acetate. The combined ethyl acetate layers were washed with 100 mL each of 1 molal NaHCO$_3$, then 10% NaCl, then 20% NaCl. The ethyl acetate layer was dried over MgSO$_4$, filtered and concentrated.

Chromatography (Isco CombiFlash® system, Analogix RS300 300 g column, 10:90 ethyl acetate:CH$_2$Cl$_2$ for 5 minutes, then to 12:88 over 35 minutes, then hold for 10 minutes) yielded 10.3 g of an oil that assayed to 91 wt % (76% yield) of the titled compound. $^1$H NMR (400 MHz, CDCl$_3$) δ ppm 1.12 (s, 9 H) 1.16 (s, 3 H) 1.64-1.74 (m, 1 H) 1.87 (dt, J=14.10, 4.48 Hz, 1 H) 2.09-2.18 (m, 2 H) 3.04 (t, J=1.92 Hz, 1 H) 3.72-3.90 (m, 2 H) 4.14-4.25 (m, 1 H) 7.33-7.52 (m, 6 H) 7.61-7.78 (m, 4 H).

Example 19E tert-butyl[((1R,2R,4R,6R)-4-{[tert-butyl(dimethyl) silyl]oxy}-1-methyl-7-oxabicyclo[4.1.0]hept-2-yl) oxy]diphenylsilane To a solution of Example 1D (8.6 g, 20.46 mmol) and imidazole (2.37 g, 34.86 mmol) in dimethylformamide (80 ml) at room temperature was added TBS-Cl (4.6 g, 30.51 mmol) in one portion. The reaction was stirred for 1 hour at which time HPLC showed <1% remaining starting material. The reaction was poured into water (150 ml) and the aqueous layer extracted with tert-butyl methyl ether (3×50 ml). The combined organic layers were washed with brine (50 ml), dried over Na$_2$SO$_4$ and concentrated in vacuo to an oil. The crude material was chromatographed with 5% ethyl acetate/ heptane to yield 11.48 g of the titled compound (99% yield, sample contains residual ethyl acetate) as an oil. $^1$H NMR (400 MHz, CDCl$_3$): δ −0.20 (s, 3H), −0.16 (s, 3H), 0.73 (s, 9H), 1.09 (s, 9H), 1.19-1.30 (m, 1H), 1.43 (s, 3H), 1.51-1.65 (m, 2H), 2.04 (s, ethyl acetate), 2.17-2.32 (M, 1H), 3.05 (s, 1H), 3.36-3.46 (m, 1H), 3.90-3.97 (dd, J=10.63, 5.97 Hz, 1H), 4.09-4.14 (q, ethyl acetate), 7.32-7.45 (m, 6H), 7.63-7.70 (m, 4H) ppm.

Example 19F (1R,3R,5R)-5-{[tert-butyl(dimethyl)silyl]oxy}-3-{[tert-butyl(diphenyl)silyl]oxy}-2-methylenecyclohexanol To a solution of 2,2,6,6-tetramethylpiperidine (4.55 g, 32.2 mmol) in benzene (40 mL) at −5° C. was added n-butyl-lithium (2.5 M in hexane, 12.9 mL, 32.2 mmol) dropwise over 20 minutes (−10<T<−5° C.). The reaction was stirred at 0 to −10° C. for 25 minutes and diethylaluminum chloride (17.9 mL, 32.2 mmol) added dropwise over 20 min (−10<T<0° C.). The reaction was maintained at 0--10° C. for 1 hour and 25 minutes and Example 19E (4.0 g, 8.05 mmol) in benzene (10 mL) was added dropwise over 10 minutes (−10<T<0° C.). The reaction was stirred for 75 minutes and poured into a mixture of saturated NH$_4$Cl (165 mL)/20% Rochelle's salt (42 mL)/ice (165 g). To the mixture was added ethyl acetate (300 mL) and 10% citric acid (75 mL) and the biphasic mixture stirred until gas evolution ceased (5 minutes). The layers were separated and the aqueous layer was extracted with ethyl acetate (2×200 mL). The combined organics were washed with 1M phosphate buffer (250 mL) then brine (250 mL), dried over Na$_2$SO$_4$ and concentrated in vacuo to an oil. The crude material was purified by silica gel chromatography (5% -10% ethyl acetate/hexane) then dried in vacuo at room temperature for one week to afford the titled compound (3.62 g, 90.5%) as an oil: $^1$H NMR (400 MHz, CDCl$_3$) δ ppm −0.14 (s, 3 H) −0.12 (s, 3 H) 0.77 (s, 9 H) 1.10 (s, 9 H) 1.17-1.19 (m, 1 H) 1.34 (q, J=11.43 Hz, 1 H) 1.38-1.46 (m, 1 H) 1.85-1.92 (m, 1 H) 1.99-2.06 (m, 1 H) 3.82-3.93 (m, 1 H) 4.41-4.47 (m, J=1.37 Hz, 1 H) 4.49-4.56 (m, 1 H) 5.00 (t, J=1.92 Hz, 1 H) 5.34 (t, J=2.06 Hz, 1 H) 7.30-7.44 (m, 6 H) 7.61-7.72 (m, 4 H); $^{13}$C NMR (100 MHz, CDCl$_3$) δ ppm −4.5, −4.3, 18.4, 19.7, 26.1, 27.3, 42.8, 46.4, 65.4, 68.2, 72.9, 108.8, 127.26, 127.30, 129.3, 129.4, 133.5, 134.0, 135.3, 135.5, 150.8; HRMS (ESI) [MNa$^+$] calculated for C$_{29}$H$_{44}$O$_3$Si$_2$ 519.2721, found 519.2729; Anal. calculated for C$_{29}$H$_{44}$O$_3$Si$_2$: C 70.11, H 8.93. Found: C 69.93, H 9.27.

Example 19G

[((3R,5R)-3,5-bis{[tert-butyl(diphenyl)silyl]oxy}-4-methylenecyclohexyl)oxy](tert-butyl)dimethylsilane To Example 19F (0.65 g, 1.31 mmol) in dimethylformamide (6 ml) at room temperature was added imidazole (0.31 g, 4.58 mmol) and TBDPS-Cl (1.08 g, 3.92 mmol), and the reaction mixture was stirred for 3 days. The reaction was poured into water (50 ml) and extracted with tert-butyl methyl ether (3×50 ml). The combined organic extraction layers were washed with water (2×) and brine (2×), dried over MgSO$_4$, and concentrated to an oil. The crude material was chromatographed with 5% ether/hexane to yield 0.92 g (95%) of the titled compound as a colorless oil. $^1$H NMR (400 MHz, CDCl$_3$) δ −0.16 (s, 6H), 0.74 (s, 9H), 0.92 (s, 9H), 1.12 (s, 9H), 1.17 (ddd, J=13.07, 10.94, 2.47 Hz, 1H), 1.30 (q, J=11.43 Hz, 1H), 1.68-1.77 (m, 1H), 1.81-1.90 (m, 1H), 3.90-4.02 (m, 1 H), 4.38 (t, J=2.74 Hz, 1H), 4.63-4.72 (m, 2H) 5.23-5.30 (m, 1H), 7.28-7.44 (m, 12H), 7.54-7.59 (m, 4H), 7.65-7.73 (m, 4H).

Example 19H (3R,5R)-3,5-bis{[tert-butyl(diphenyl)silyl]oxy}-4-methylenecyclohexanol To a suspension of Example 19G (1.05 g, 1.43 mmol)) in ethanol (8 mL) was added concentrated HCl (104 μL, 1.28 mmol) in ethanol (2 mL), and the reaction mixture was stirred at room temperature for 3 hours. The reaction was poured into 1M NaHCO$_3$ (35 mL) and extracted with tert-butyl methyl ether (3×35 mL). The combined organics were washed with brine (35 mL), dried over Na$_2$SO$_4$ and concentrated to an oil. The crude material was purified by silica gel chromatography (5% ethyl acetate/hexane) then dried in vacuo at room temperature for one week to afford the titled compound (0.74 g, 83%) as a white solid: $^1$H NMR (400 MHz, CDCl$_3$) δ ppm 1.01 (s, 9 H) 1.02 (s, 9 H) 1.60-1.85 (m, 4 H) 2.46 (s, 1 H) 3.96-4.06 (m, 1 H) 4.63 (dd, J=6.79, 4.05 Hz, 1 H) 4.74 (t, J=5.35 Hz, 1 H) 4.85 (s, 1 H) 4.91 (s, 1 H) 7.27-7.45 (m, 12 H) 7.56-7.67 (m, 8 H); $^{13}$C NMR (100 MHz, CDCl$_3$) δ 19.5, 19.6, 27.2, 27.3, 44.6, 67.0, 70.4, 107.9, 127.21, 127.24, 127.3, 129.33, 129.35, 129.5, 132.6, 133.2, 133.4, 133.9, 135.44, 135.48, 135.54, 135.6, 149.9; HRMS (ESI) [MNa+] calcd for C$_{39}$H$_{48}$O$_3$Si$_2$ 643.3034, found 643.3022; Anal. calcd for C$_{39}$H$_{48}$O$_3$Si$_2$: C 75.43, H 7.79. Found: C 75.50, H 7.97.

Example 19 I (3R,5R)-3,5-bis{[tert-butyl(diphenyl)silyl]oxy}-4-methylenecyclohexanone To a solution of Example 19H (0.50 g, 0.805 mmol) in CH$_2$Cl$_2$ (7 mL) was added Dess-Martin periodinane (0.376 g, 0.886 mmol) and the suspension was stirred at room temperature for 3.5 hours. The reaction was diluted with CH$_2$Cl$_2$ (10 mL) and washed with 3:1 1M NaHCO$_3$: 1M Na$_2$SO$_3$ (10 mL) followed by 3:1 ½ saturated brine: 1M NaHCO$_3$ (10 mL). The organic layer was dried over Na$_2$SO$_4$ and concentrated in vacuo to a white solid. The crude material was purified by silica gel chromatography (5% ethyl acetate/hexane) then dried in vacuo at room temperature for one week to afford the titled compound (0.49 g, 98%) as a white solid: $^1$H NMR (400 MHz, CDCl$_3$) δ ppm 0.99 (s, 18 H) 2.29-2.49 (m, 4 H) 4.74-4.80 (m, 2 H) 5.17 (t, J=1.07 Hz, 2 H) 7.29-7.36 (m, 8 H) 7.36-7.45 (m, 4 H) 7.54-7.63 (m, 8 H); $^{13}$C NMR (100 MHz, CDCl$_3$) δ 19.5, 27.2, 51.2, 70.9, 109.2, 127.3, 127.4, 129.5, 129.6, 132.7, 133.1, 135.40, 135.43, 148.6, 205.8; HRMS (ESI) [M+Na$^+$] calcd for C$_{39}$H$_{46}$O$_3$Si$_2$ 641.2878, found 641.2869; [M+NH$_4^+$] calcd 636.3324, found 636.3313; Anal. calcd for C$_{39}$H$_{46}$O$_3$Si$_2$: C 75.68, H 7.49. Found: C 75.48, H 7.59.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection, and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids. The term "pharmaceutically acceptable salts," as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, citrate, digluconate, ethanesulfonate, glycerophosphate, heptanoate, hexanoate, fumarate, hydrochloride, hydrobromide, hydroiodide, hydroxybutyrate, 2-hydroxyethanesulfonate (isethionate), lactate, malate, maleate, methanesulfonate, nicotinate, 2-naphthalenesulfonate, oxalate, pamoate, pectinate, persulfate, phenylacetate, 3-phenylpropionate, picrate, pivalate, propionate, salicylate, succinate, sulfate, tartrate, thiocyanate, phosphate, glutamate, carbonate, p-toluenesulfonate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide or alkyl triflate, for example with methyl iodide, methyl triflate, benzyl iodide, or cyclopentyl iodide. They also can be prepared by reaction of the compound with an acid such as hydrochloric acid and an alcohol such as ethanol or methanol, or with an alcohol and a coupling agent such as 1-(3-dimethylaminopropyl)-3-ethylcarbodiimide hydrochloride (EDAC), or 1,3-dicyclohexylcarbodiimide (DCC).

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine or dialkylamine, for example with methylamine, diethylamine, or piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need may be converted through in vivo biotransformation into compounds of formula (I).

Method of Use

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in a pharmaceutically acceptable salt. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds of the invention may be administered alone, or in combination with one or more other compounds of the invention, or in combination (i.e. co-administered) with one or more additional pharmaceutical agents. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

The total daily dose of the compounds of this invention administered to a human or animal ranges from about 0.01 µg to about 150 mg. More preferable doses can be in the range of from about 0.01 µg to about 10 mg. If desired, the effective daily dose can be divided into multiple doses for purposes of administration. Consequently, single dose compositions may contain such amounts or submultiples thereof to make up the daily dose.

Determination of Biological Activity

Figure 3:
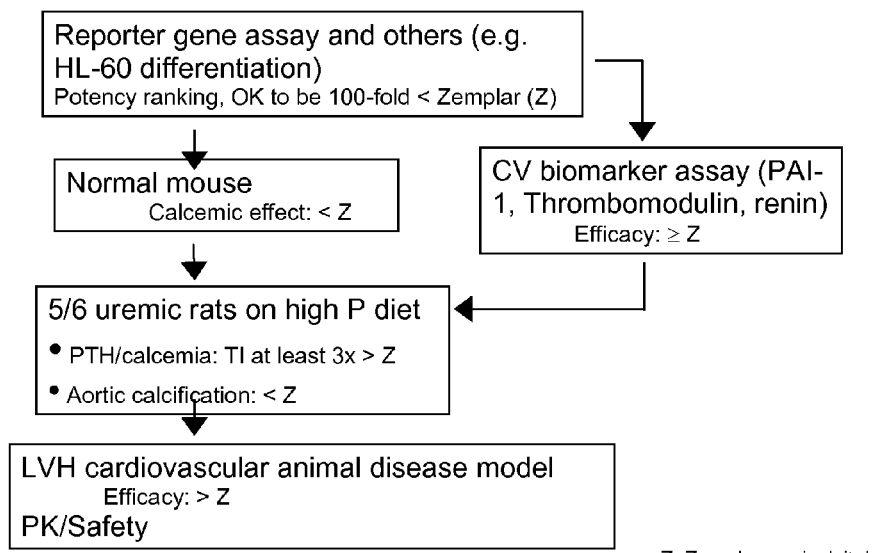
FIG. 3 schematically illustrates a flow chart identifying the various in vitro and/or in vivo assays conducted on the compounds according to the present invention to assess biological activity.

Biological activity of the compounds was assessed to identify potential compounds having desirable biochemical characteristics, using paricalcitol as a reference. FIG. 3 illustrates the flow chart of how these assessments were carried out. Compound activity was assessed first, using in vitro binding to Vitamin D nuclear receptor, a reporter gene assay, and HL-60 differentiation. Compounds according to the invention were ranked according to potency compared to paricalcitol. Compounds found, as a result of one or more of these assays, to have potencies of down to about 100-fold less than paricalcitol were selected for additional assessment.

Compounds were next evaluated using normal mice to determine calcemic effect and in appropriate cell lines to determine impact on cardiovascular biomarkers, specifically plasminogen activator inhibitor-1 (PAI-1), thrombomodulin, thrombospondin-1, and renin in cardiomyocytes. Renin activity was also evaluated in As4.1 cells. It was desired to identify compounds having a lesser calcemic effect than paricalcitol in the mouse and an efficacy greater than paricalcitol in the biomarker assays.

To provide an indication of therapeutic index, compounds were next evaluated in a rat model of kidney disease for PTH suppression and calcemia. The goal was to identify compounds having a therapeutic index (TI) at least three times that of paricalcitol and those that did not contribute to aortic (or soft tissue) calcification to a greater extent than paricalcitol.

Finally, an in vivo model of left ventricular hypertrophy was used to determine the potential to treat cardiovascular disease. With calcification of the circulatory system, hypertension develops. A thickening of the mycocardium of the left ventricle results as the heart has to pump harder to maintain flow in the vasculature. Efficacy greater than paricalcitol was desired.

Each of these activity assessments is described in greater detail below, but those skilled in the art will be familiar with them and recognize them as conventional techniques.

VDR Binding

In vitro binding of selected compounds according to the invention to VDR was assessed using the following procedure. Purified recombinant full-length human Vitamin D nuclear receptor (commercially available from PanVera/Invitrogen (Carlsbad, Calif.) Part Number P2190) was diluted in VDR binding buffer (50 mM Tris (pH 7.5), 5 mM DTT, 300 mM KCl, 0.01 % TWEEN 20). Immediately prior to assay, [$^3$H]-Calcitriol (1α, 25-dihydroxy[23,24(n)-$^3$H]cholecalciferol, Amersham Biosciences, Piscataway, N.J.; product code TRK588-5UCl) was diluted in binding buffer in a siliconized Eppendorf tube. Each test compound was then serially diluted in binding buffer to concentrations appropriate for the assay, as one skilled in the art can determine. A diluted test compound or positive control (paricalcitol, commercially available as ZEMPLAR, from Abbott Laboratories, Illinois) was added to each well of a 96-well microtiter plate (Wallac Isoplate Part 1450-516, commercially available from Perkin-Elmer Co., Boston, Mass.) followed by the [$^3$H]-Calcitriol (1 nM final).

The diluted stock of VDR (100 ng/well) was then added to each well. Final assay volume was 100 uL. The filled plate was incubated overnight at 4° C. with gentle shaking. After 18 hours of incubation, 20 uL of wheat germ agglutinin-coated yttrium silicate scintillation proximity assay (SPA) beads (commercially available from Amersham Biosciences, Piscataway, N.J.; Part # RPNQ0270) resuspended in binding buffer was added to each well (200 ug/well) and the plate was incubated at room temperature for 2 hours with gentle shaking. Bound [$^3$H]-Calcitriol was then counted using a Packard Top-Count. Non-specific binding was defined as cpm [$^3$H]-Calcitriol bound in the presence of excess (10 uM) paricalcitol.

Table 1. summarizes binding data obtained for selected compounds.

TABLE 1

| VDR Binding | |
| --- | --- |
| Example | VDR Binding IC50 (nM) |
| Paricalcitol | 14.6 |
| Calcitriol | 0.03 |
| 1 | 496.4 |
| 2 | 890.5 |
| 3 | 1334.5 |

TABLE 1-continued

VDR Binding

| Example | VDR Binding IC50 (nM) |
|---|---|
| 4 | 62.4 |
| 5 | 0.1 |

VDRE Reporter Gene Assay

Compound activity was also assessed by looking at a Vitamin D Response Element (VDRE) reporter gene assay, Human Embryonic Kidney cells (HEK cells) with a stable expression of VDR were cultured in 96-well plates at ~4×10$^5$ cells/mL (100 µL/well) in DMEM medium containing 10% fetal calf serum. Cells were transfected with 0.2 µg per well of a VDRE-luciferase-reporter construct (from Y. Li, University of Chicago) and then treated with test agents at indicated concentrations for 24 hours. The luciferase activity was then measured following the manufacturer's instructions (Promega, Madison, Wis.). Signal strength of each sample was detected and increase in signal detected is shown in Table 2.

TABLE 2

VDR Reporter Gene

| Example | EC50 (nM) |
|---|---|
| Paricalcitol | 5.9 |
| Calcitriol | 5.9 |
| 1 | 0.4 |
| 2 | 52.7 |
| 3 | 0.9 |
| 4 | 1.3 |
| 5 | 0.3 |
| 6 | 1.3 |
| 7 | 12.2 |
| 8 | <0.01 |
| 9 | >10000 |
| 10 | 149.8 |
| 11 | 181.8 |
| 12 | 16.9 |
| 13 | 275.8 |
| 14 | 0.6 |
| 15 | 0.4 |
| 16 | 71.7 |
| 17 | 153.0 |
| 18 | 11.3 |

HL-60 Differentiation

Human promyelocytic leukemia (HL60) cells were obtained from the American Type Culture Collection (ATCC Cat. # CCL-240, Manassas, Va.). Cells were maintained in RPMI 1640 medium (commercially available from Invitrogen, Carlsbad, Calif.) containing 10% fetal bovine serum (commercially available from Invitrogen, Carlsbad, Calif.) at 37° C. with 5% $CO_2$. Cells were passaged weekly and were not allowed to become >90% confluent. For the assay, cells were plated at 5×10$^5$ cells per well in 200 uL media. Test compounds were diluted in media in concentrations between $10^{-6}$-$10^{-10}$ M and then added to the appropriate wells. Cells were then incubated for four days at 37° C. in 5% $CO_2$ atmosphere. After incubation, media was aspirated from each well and 75 uL of NBT solution (nitroblue tetrazolinium: 200 ng/mL PMA (phorbol 12-myrystate 13-acetate) and 2 mg/ml NBT (nitroblue tetrazolium) in distilled $H_2O$) was added to each well followed by further incubation for 2 hours at 37° C. Following incubation, 150 uL lysis buffer (225 mL dimethylformamide, 67.5 g SDS). PMA stock solution (2 mg/ml in ethanol) was added to each well and the plate was allowed to sit at room temperature for 4 hours. HL-60 cell differentiation was assayed, Effect of each compound on cell growth was examined as a function of time; absorbance in each well was measured at 570 nm. Table 3 shows EC50s of selected compounds.

TABLE 3

HL-60 Differentiation

| Example | EC50 (nM) |
|---|---|
| Paricalcitol | 16 |
| Calcitriol | 7 |
| 1 | 1.9 |
| 2 | 162.0 |
| 3 | 3.9 |
| 4 | 0.7 |
| 5 | 0.0001 |
| 6 | 12.0 |
| 7 | 12.5 |
| 8 | 31.5 |
| 9 | 434.5 |
| 10 | 621.0 |
| 11 | 310.0 |
| 12 | 0.2 |
| 13 | 52.0 |
| 14 | 9.0 |
| 15 | 1.2 |
| 16 | 43.0 |
| 17 | 92.5 |
| 18 | 10.0 |

Renin mRNA in As4.1

As4.1 cells (ATCC, Manassas, Va.) were cultured in Dulbecco's Modified Eagle Medium DMEM (commercially available from Invitrogen, Carlsbad, Calif.) with 10% fetal bovine serum at 37° C. in a humidified 5% $CO_2$-95% air atmosphere. C3;ells were transfected with the pcDNA-hVDR plasmid (provided by Yan Chun Li, University of Chicago) by LIPOFECTAMINE™ 2000 (Invitrogen, Carlsbad, Calif.). siRNA was transfected with the pcDNA-hVDR plasmid by LIPOFECTAMINE™ 2000 according to the manufacturer's protocol. Twenty-four hours after transfection, cells were treated with test agents.

Real-time reverse transcription-PCR was performed with a MyiQ Real-time PCR Detection System (commercially available from BioRad, Hercules, Calif.). Each sample had a final volume of 25 µl containing 100 ng of cDNA, 0.4 mM each of the forward and reverse PCR primers and 0.1 mM of the TaqMan™ probe. TaqMan™ probes that were 5' labeled with the reporter 6-carboxyfluorescein (FAM) and 3' labeled with the quencher tetramethylrhodamine (TAMRA) were used and the primer and probe sets were obtained from Applied Biosystems (Foster City, Calif.). Temperature conditions consisted of a step of 5 minutes at 95° C., followed by 45 cycles of 60° C. for 1 minute and 95° C. for 15 seconds. Data was collected during each extension phase of the PCR reaction and analyzed with the accompanying software package (BioRad, Hercules, Calif.). Threshold cycles were determined for each gene. Selected $IC_{50}$ values are shown in Table 4.

TABLE 4

Renin mRNA in AS4.1

| Example | $IC_{50}$ (nM) |
|---|---|
| Paricalcitol | 0.8 |
| Calcitriol | 1.6 |

TABLE 4-continued

Renin mRNA in AS4.1

| Example | $IC_{50}$ (nM) |
|---|---|
| 1 | 0.3 |
| 2 | 0.7 |
| 3 | 0.4 |
| 4 | 3.4 |
| 5 | 2.4 |
| 6 | 18.6 |
| 7 | 0.1 |
| 8 | 0.3 |
| 9 | inactive |
| 10 | 3.9 |
| 11 | 0.002 |
| 12 | 0.2 |
| 13 | 0.9 |
| 14 | 0.03 |
| 15 | 0.04 |
| 16 | 14.7 |
| 17 | 2.2 |
| 18 | 0.1 |

Cardiovascular Biomarkers in Smooth Muscle Cells

Primary culture of human coronary artery smooth muscle cells (CASMC) (commercially available from Cambrex, Walkersville, Md.) were grown in smooth muscle growth medium SmGM-2 (commercially available from Lonza Bioscience) containing 5.5 mM glucose, 5% FBS, 50 µg/ml gentamicin, 50 ng/ml amphotericin-B, 5 µg/ml insulin, 2 ng/ml human recombinant fibroblast growth factor (hFGF), and 0.5 ng/ml human recombinant epidermal growth factor (hEGF) at 37° C. in a humidified 5% $CO_2$-95% air atmosphere. Cells were grown to >80% confluence and used within five passages.

Real-time reverse transcription-PCR was performed with a MyiQ Real-Time PCR Detection System (BioRad, Hercules, Calif.). Each sample has a final volume of 25 µl containing 100 ng of cDNA, 0.4 mM each of the forward and reverse PCR primers and 0.1 mM of the TaqMan™ probe for the gene of interest (Applied Biosystems, Foster City, Calif.). Temperature conditions consisted of a step of 5 minutes at 95° C., followed by 40 cycles of 60° C. for 1 minute and 95° C. for 15 seconds. Data was collected during each extension phase of the PCR reaction and analyzed with the software package (BioRad, Hercules, Calif.). Threshold cycles were determined for each gene.

SDS-PAGE and Western Blot Analysis: Cells ($1\times10^6$ cells per sample) or cell extract preparations were solubilized in SDS-PAGE sample buffer (Invitrogen, Carlsbad, Calif.), and the protein content in each sample was determined by the Pierce (Rockford, Ill.) BCA protein assay. Samples were resolved by SDS-PAGE using a 4-12% NuPAGE gel (Invitrogen, Carlsbad, Calif.), and proteins were electrophoretically transferred to PVDF membrane for Western blotting. The membrane was blocked for 1 h at 25° C. with 5% nonfat dry milk in PBS-T and then incubated with a rabbit anti-osteoprotegerin polyclonal antibody (1:100 fold dilution, Santa Cruz Biotechnology, Santa Cruz, Calif.), a mouse anti-plasminogen activator inhibitor-1 (PAI-1) monoclonal antibody (1000-fold dilution, Santa Cruz Biotechnology, Santa Cruz, Calif.), a mouse anti-thrombospondin-1 (THBS1) monoclonal antibody (2000-fold dilution, Calbiochem, La Jolla, Calif.), a mouse anti-thrombomodulin (TM) monoclonal antibody (2000-fold dilution, Santa Cruz Biotechnology, Santa Cruz, Calif.), a mouse anti-VDR monoclonal antibody (1:500 fold dilution), a mouse anti-PPARγ (1:200 fold dilution) monoclonal antibody (Santa Cruz Biotechnology, Santa Cruz, Calif.), a rabbit anti-NFκB polyclonal antibody (1:200 fold dilution, Cell Signaling Technology, Danvers, Mass.) or a rabbit anti-Ncor1 polyclonal antibody (1:200 fold dilution, Abcam Inc., Cambridge, Mass.) in PBS-T overnight at 4° C. The membrane was washed with PBS-T and incubated with a horseradish peroxidase-labeled anti-mouse (for VDR and PPARγ) or anti-rabbit (for osteoprotegerin, the p65 subunit of NFκB and Ncor1) second antibody for 1 h at 25° C. The membrane was then incubated with detection reagent (SuperSignal WestPico, Pierce, Rockford, Ill.). Specific bands were visualized by exposing the paper to Kodak BioMax films. Band intensity was quantified by Quantity One (BioRad, Hercules, Calif.). Selected $IC_{50}$ and $EC_{50}$ values are shown in Table 5.

TABLE 5

Biomarkers in Smooth Muscle Cells

| Example | PAI-1 mRNA in CASMC $IC_{50}$ (nM) | Thrombomodulin mRNA in CASMC $EC_{50}$ (nM) | Thrombospondin mRNA in CASMC $IC_{50}$ (nM) |
|---|---|---|---|
| Paricalcitol | 0.5 | 1.5 | 0.2 |
| Calcitriol | 0.8 | 1.6 | 19.1 |
| 1 | 0.01 | 2.2 | 0.004 |
| 2 | 0.03 | inactive | 3.7 |
| 3 | 0.003 | 39.9 | 0.002 |
| 4 | 0.02 | 84.7 | 0.001 |
| 5 | 0.002 | 5.6 | 0.001 |
| 6 | inactive | inactive | 1.3 |
| 7 | 0.1 | 0.6 | 0.1 |
| 8 | 0.02 | 39.3 | 0.05 |
| 9 | 0.1 | 0.1 | 0.3 |
| 10 | 0.04 | 0.2 | 0.01 |
| 11 | 0.01 | 28.4 | 0.01 |
| 12 | 11.5 | 0.1 | 0.02 |
| 13 | 0.01 | 80.2 | 0.03 |
| 14 | 0.04 | 5.1 | 0.02 |
| 15 | 0.01 | 10.7 | inactive |

Normal Mouse Calcemia Model

Male, C57BL6, mice were obtained from Jackson Laboratories. The mice were habituated for four days while maintained on a normal diet (D10001, Research Diets Inc.). Treatment was initiated with vehicle (20% ethanol/30% propylene glycol/50% water, 0.05 mL, s.c.) or test agent administered over a three log dose range. The animals were dosed once daily for 3 days. Twenty-four hours after the last dose, animals were anesthetized with ketamine/xylazine (100/18 mg/kg) and bled by cardiac puncture for measurement of PTH and other end points.

Figure 4:
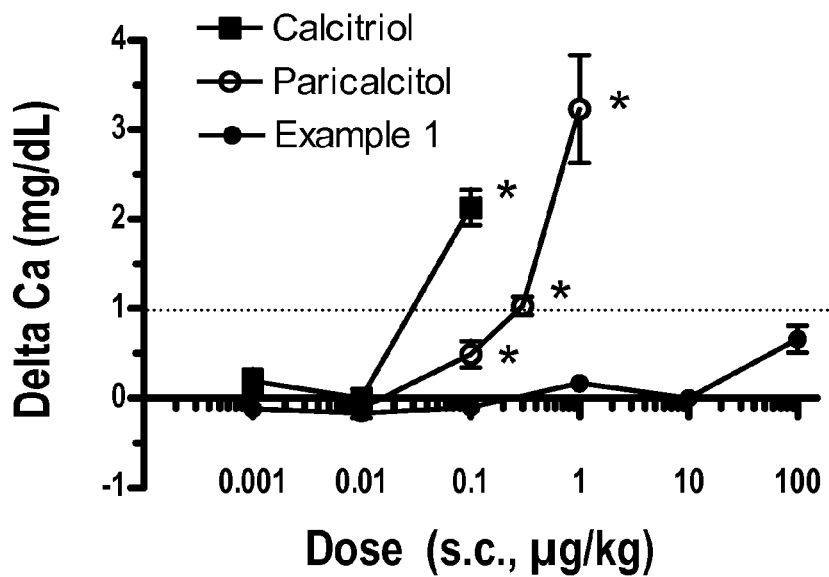
FIG. 4 illustrates in graphical form the dose response of calcitriol, paricalcitol, and Example 1 in a normal mouse calcemia model.
Figure 4:
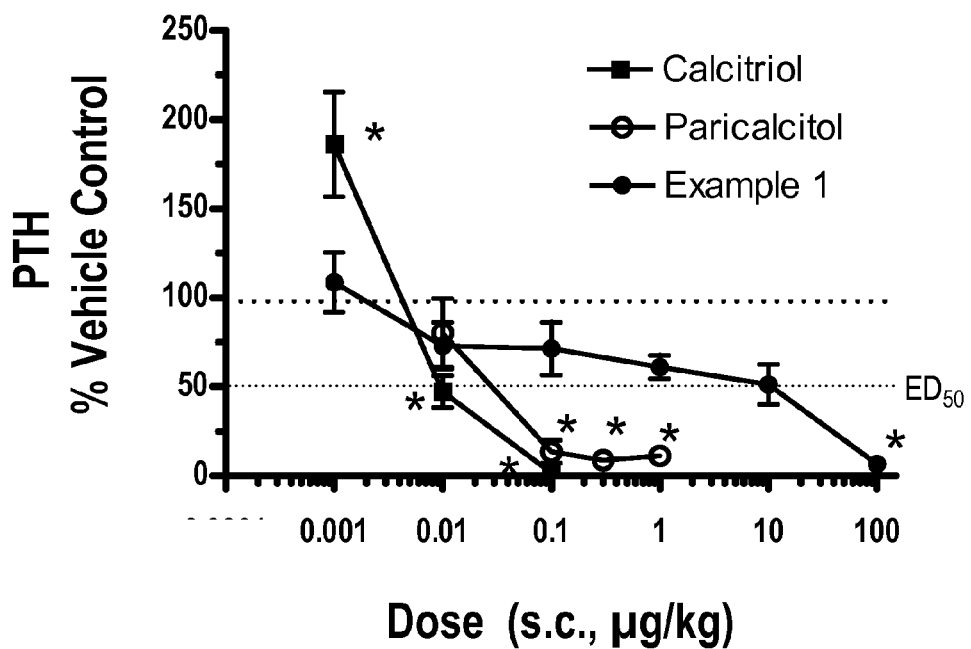

Measurement of PTH and minerals: Calcium (Ca), serum phosphorus (Pi), creatinine and BUN were measured from serum using an Abbott Aeroset® (Abbott Laboratories, Abbott Park, Ill.). Blood ionized calcium (iCa) was determined using the i-STAT® system (Abbott Laboratories, East Windsor, N.J.). Serum PTH was measured using a mouse parathyroid hormone (PTH) EIA kit obtained from ALPCO/Immutopics, Inc. (Windham, N.H.). Selected data is shown is Table 6. The graphs in FIG. 4 give an indication of dose response. Notable is that Example 1 produced an approximately 30% reduction in PTH over at least a three log dose range without a concomitant elevation of serum calcium of greater than 1 mg/dL. This data is suggestive of the potential for a wider therapeutic window relative to the other two compounds tested.

Data analysis: Mean±standard error of the mean was calculated for each group. One way ANOVA followed by a Dunnett's test was used to assess differences between vehicle and drug-treated groups. *$p<0.05$=significance.

TABLE 6

| Mouse Calcemia | 1 mg/dL Δ total Ca μg/kg | PTH ED$_{50}$ μg/kg |
|---|---|---|
| calcitriol | 0.026 | 0.0091 |
| paricalcitol | 0.286 | 0.028 |
| Example 1 | >100 | 10.47 |

Aortic Calcification in Uremic Rats

5/6 nephrectomized rats: Male Sprague-Dawley, 5/6 NX rats (~200 g) were obtained from Charles River. The nephrectomy was performed using a standard two-step surgical ablation procedure. Beginning approximately 2 weeks post-nephrectomy, rats were maintained on a hyperphosphatemia-inducing diet (0.9% phosphorus and 0.6% calcium) for the duration of the study to induce secondary hyperparathyroidism (SHPT). After four weeks on the special diet, rats received vehicle (5% ethanol/95% propylene glycol; 0.4 mL/kg; i.p.) or test agent 3 times per week for 41 Days. On Days 0, 13, and 41 blood was collected (24 hours post-dose).

To minimize bias induced by variance in the disease state, 5/6 NX rats were assessed after 4 weeks of high phosphorus diet (prior to treatment) and the following inclusion/exclusion criteria were applied to the rats for study:
Serum creatinine=0.8-2.0 mg/dL (sham controls=0.43±0.01 mg/dL; n=20)
Exclude: serum calcium≦8.5 mg/dL (sham controls=10.05±0.05 mg/dL; n=20)
Exclude: serum phosphorus>12 mg/dL (sham controls=7.09±0.12 mg/dL; n=20)
Exclude: iPTH<400 pg/mL (sham controls=430±33 pg/mL; n=20)

Measurement of PTH and serum mineral levels: Serum PTH was measured using a rat intact PTH ELISA kit (ALPCO/lmmutopics, Inc., Windham, N.H.). Serum calcium, phosphorus, creatinine and BUN concentrations were measured using an Abbott Aeroset® (Abbott, Abbott Park, Ill.). Blood ionized calcium was determined using an i-STAT® portable clinical analyzer (Abbott Laboratories, East Windsor, N.J.).

Aorta were dissected, separated from extraneous tissue, weighed, reduced to ash at high temperature, diluted in acid buffer, and analyzed for total calcium with an Aeroset® clinical analyzer (Abbott Laboratories, Abbott Park, Ill.).

Data Analysis: Mean±SEM are presented for each group. One Way ANOVA followed by a Dunnett's post-hoc test was used to assess differences between corresponding days in SHAM, Vehicle and VDRA-treated groups. *p<0.05 vs corresponding Day; #p<0.05 vs 5/6 NX.

Example 1 did not have an effect on aortic calcification at <100 μg/kg.

Study 1: The purpose of the study was to compare the effects of Example 1 on serum PTH, ionized Ca++, total Ca++ and phosphorus in the 5/6 NX rat model.

Methods: 5/6 NX rats were fed a normal diet (Teklad 8640; 0.9% Phos. and 1.1% Ca++) for 4 weeks prior to study at 6 weeks uremia, and were maintained on this diet for the duration of the study. 5/6 NX rats were treated with vehicle and 10, 30 or 100 μg/kg of A-Example 1. Rats were dosed i.p. 3×/week for 2 weeks. Blood was collected on Days 0 and 13 for determination of concentrations of PTH, ionized Ca++, total Ca++ and phosphorus. Statistical analysis was performed with paired t-tests to compare Day 0 vs. Day 13; statistical significance was achieved at p<0.05.

Results: Example 1 treatment at 30 and 100 μg/kg decreased PTH by 26% and 78%, respectively. Both ionized and total Ca++ were elevated @100 μg/kg of Example 1. Example 1 did not affect serum phosphorus levels; however, there was a decrease in the vehicle-treated sham and 5/6 NX rats.

Study 2: To determine if treatment with Example 1 (1, 10 & 100 μg/kg) reduces left ventricular hypertrophy (LVH) in 5/6 NX uremic rats.

Methods: Previous studies have shown that the 5/6 NX rat is hypertensive and presents with left ventricular hypertrophy. Therefore, 5/6 NX rats were received from Charles River at 2 weeks uremia and fed TD04151 (0.6% Ca and 0.9 % P) 4 weeks prior to study. 5/6 NX rats were treated with Example 1 (1, 10 & 100 μg/kg) or vehicle (95% PG/5% EtOH) 3×/week for six weeks. On Days 0, 13 and 41 blood was drawn (24 hours post-dose). At the end of the six week treatment period, rats were anesthetized with isoflurane and echocardiography was performed. Left ventricular mass was determined according to the American Society of Echocardiography recommendations using the cube method. After euthanasia, direct measurements of left ventricular weight were obtained. Note: Vehicle treated SHAM and 5/6 NX rats (3×/week for six weeks) from previous studies were included in this study for comparison purposes. All values are mean±SEM. Data was analyzed using ANOVA and where noted t-test. * Indicates p<0.05 compared to SHAM.

Results: There were no detectable differences in left ventricular mass in 5/6 NX rats treated with Example 1 (1,10 and 100 μg/kg, 3×/wk for 6 wks) compared to vehicle treated 5/6 NX rats. There were no differences in cardiac performance between the groups. There is no exacerbation of LVH by treatment with Example 1 compared to controls.

Methods of the Invention

Compounds and compositions of the invention are useful for modulating the effects of vitamin D receptors. In particular, the compounds and compositions of the invention can be used for treating and preventing disorders modulated by vitamin D receptors. Typically, such disorders can be ameliorated by selectively modulating the vitamin D receptor in a mammal, preferably by administering a compound or composition of the invention, either alone or in combination with another active agent, for example, as part of a therapeutic regimen.

The compounds of the invention, including but not limited to those specified in the examples, possess an affinity for vitamin D receptors. As vitamin D receptor activators, the compounds of the invention can be useful for the treatment and prevention of a number vitamin D receptor-mediated diseases or conditions.

For example, vitamin D receptor activators have been shown to play a significant role in reducing parathyroid hormone levels (Hudson, J. Q. The Annals of Pharmacotherapy, 2006, 40, 1584-1593). As such, vitamin D receptor activators are suitable for the treatment of conditions and disorders related to chronic kidney disease. Some vitamin D receptor activators do not upregulate intestinal vitamin D receptors, thus limiting calcemic and hyperphosphatemic effects and the associated side effects (Slatopolsky, E.; Finch, J.; Ritter, C.; Takahashi, F. American Journal of Kidney Disease, 1998, 4, S40-S47). Studies have indicated that vitamin D receptor activator therapy reduces the progression of renal disease (Agarwal, R.; Acharya, M.; Tian, J.; Hippensteel, R. L.; Melnick, J. Z.; Qiu, P.; Williams, L.; Bathle, D. Kidney International, 2005, 68, 2823-2828 and Schwarz, U.; Amann, K.; Orth, S. R.; Simonaviciene, A.; Wessels, S.; Ritz, E. Kidney International, 1998, 53, 1696-1705).

In addition, vitamin D receptor activators have been shown to be involved in skeletal and mineral homeostasis. These receptor activators are important for intestinal calcium absorption and subsequent anabolic activity on bone (Hendy, G. N.; Hruska, K. A.; Methew, S.; Goltzman, D. Kidney International, 2006, 69, 218-223). Certain agonists have shown the potential to selectively treat bone disorders with a lessened effect on parathyroid hormone suppression. (Shevde, N. K.; Plum, L. A.; Clagett-Dame, M.; Yamamoto, H.; Pike, J. W.; DeLuca, H. F. Proc. Natl. Acad. Sci. U.S.A. 2002, 99, 13487-13491; Uchiyama, Y.; Higuchi, Y.; Takeda, S.; Masaki, T.; Shira-Ishi, A.; Sato, K.; Kubodera, N.; Ikeda, K.; Ogata, E. Bone, 2002, 4, 582-588 and Shiraishi, A.; Higashi, S.; Ohkawa, H.; Kubodera, N.; Hirasawa, T.; Ezawa, I.; Ikeda, K.; Ogata, E. Calcified Tissue International, 1999, 65, 311-316).

Vitamin D receptor activators have been implicated in having affects on many aspects of the circulatory system. The vitamin D receptor system plays an important role in maintaining antithrombotic homeostasis (Aihara, K.; Azuma, H.; Akaike, M.; Ikeda, Y.; Yamashita, M.; Sudo, T.; Hayashi, H.; Yamada, Y.; Endoh, F.; Fujimura, M.; Yoshida, T.; Yamaguchi, H.; Hashizume, S.; Kato, M.; Yoshimura, K.; Yamamoto, Y.; Kato, S.; Matsumoto, T. J. Biol. Chem., 2004, 279, 35798-35802). Vitamin D receptor activators have been show to alter the expression and activity of proteins important for coagulation such as thrombomodulin, tissue factor, and plasminogen activator inhibitor 1 offering potential treatment in atherosclerotic diseases (Beer, T. M.; Venner, P. M.; Ryan, C. W.; Petrylak, D. P.; Chatta, G.; Ruether, J. D.; Chi, K. N.; Curd, J. G.; DeLoughery, T. G. British Journal of Haematology, 2006, 135, 392-394 and Ohsawa, M.; Koyama, T.; Yamamoto, K.; Hirosawa, S.; Kamei, S.; Kamiyama, R. Circulation, 2000, 102, 2867-2872). The renin-angiotensin II system is central in the regulation of blood pressure and elevated renin levels lead to hypertension, and cardiac hypertrophy. Vitamin D receptor activators directly suppress renin gene transcription in a vitamin D receptor-dependent mechanism offering a control mechanism for this system (Li, Y. C.; Qiao, G.; Uskokovic, M.; Xiang, W.; Zheng, W.; Kong, J. Journal of Steroid Biochemistry & Molecular Biology, 2004, 89-90, 397-392). Patients with chronic kidney disease receiving maintenance hemodialysis often suffer cardiovascular complications of which ischemic heart disease as a result of left ventricular hypertrophy is the most prominent. Hyperparathyroidism is a contributor and even partial control with a vitamin D receptor activator results in regression of myocardial hypertrophy without changes in other hemodynamic parameters (Park, C. W.; Oh, Y. S.; Shin, Y. S.; Kim, C. -M.; Kim, Y. -S.; Kim, S. Y.; Choi, E. J.; Chang, Y. S.; Bang, B. K. American Journal of Kidney Diseases, 1999, 33, 73-81).

The vitamin D receptor is expressed on most cell types of the immune system and in particular in modulating T cell responses. Currently vitamin D receptor activators are used topically to treat psoriasis. Animal models are suggestive that vitamin D receptor activators can be beneficial in the treatment of arthritis, autoimmune diabetes, experimental allergic encephalomyelitis, inflammatory bowel disease, and systemic lupus erythematosus suggesting the expansion of therapeutic utility in humans (Adorini, L. Cellular Immunology, 2005, 233, 115-124).

A number of signaling pathways involved with cancer are affected by vitamin D receptor activators. They are prominently although with a great deal of heterogeneity responsible for antiproliferative, anti-angiogenic, and pro-differentiation effects in a broad range of cancers mediated through both genomic and non-genomic mechanisms (Deeb, K. K.; Trump, D. L.; Johnson, C. S. Nature Reviews Cancer, 2007, 7, 684-700). The role of vitamin D metabolism seems to be important in the regulation of cell proliferation in the prostate (Lou, Y.-R.; Qiao, S.; Talonpoika, R.; Syvala, H.; Tuohimaa, P. Journal of Steroid Biochemistry and Molecular Biology, 2004, 92, 317-3250). There is an association of suppression of the autocrine growth factors IL-6 and IL-8 by vitamin D receptor activators and the development of Kaposi sarcoma (Masood, R.; Nagpal, S.; Zheng, T.; Cai, J.; Tulpule, A.; Smith, D. L.; Gill, P. S. Blood, 2000, 96, 3188-3194). Vitamin D analogs exert a differentiating effect on leukemia cells (James, S. Y.; Williams, M. A.; Newland, A. C.; Colston, K. W. Gen. Pharmac., 1999, 32, 143-154).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.01 μg to about 150 mg. More preferable doses can be in the range of from about 0.010 μg to about 10 mg. If desired, the effective daily dose can be divided into multiple doses for purposes of administration. Consequently, single dose compositions may contain such amounts or submultiples thereof to make up the daily dose.

Compounds of the invention are vitamin D receptor activators that modulate function of vitamin D receptors by altering the activity of the receptor or signaling. Therefore, the administration of a therapeutically effective amount of a compound of formula (I) to a mammal provides a method of selectively modulating the effects of vitamin D receptors.

Furthermore, the administration of a therapeutically effective amount of a compound of formula (I) to a mammal provides a method of treating or preventing a condition or disorder selected from the group consisting of renal disease, secondary hyperparathyroidism associated with chronic kidney disease, osteoporosis, osteomalacia, osteodystrophy, thrombus formation, the renin-angiotensin system, myocardial hypertrophy, hypertension, autoimmune disorders, immunosuppression, transplant rejection, arthritis, multiple sclerosis, psoriasis, inflammatory bowel disease, type 1 diabetes, and systemic lupus erythematosus, cancers of the colon, prostate, breast, leukemia and Kaposi sarcoma. More preferred, the administration of a therapeutically effective amount of a compound of formula (I) to a mammal provides a method of treating secondary hyperparathyoidism, hypertension, and myocardial hypertrophy.

The compounds identified by the methods described hereinabove may be administered as the sole pharmaceutical agent or in combination with one or more other pharmaceutical agents where the combination causes no unacceptable adverse effects.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

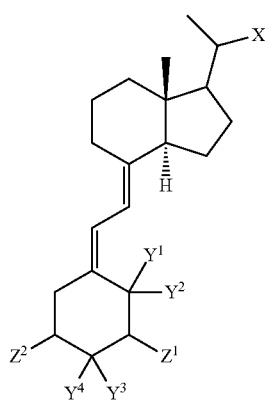

(I)

or a pharmaceutically acceptable salt thereof, wherein
the carbon to which X is attached can have the R or S configuration;
X is —CH$_2$OC(O)R$^2$;
Y$^1$ and Y$^2$ are each hydrogen;
Y$^3$ and Y$^4$ taken together are a methylene group;
Z$^1$ is fluorine, hydroxy, or hydroxymethyl;
Z$^2$ is fluorine or hydroxy; and
R$^2$ is alkyl, alkylamino, alkylcarbonyloxyalkyl, or hydroxyalkyl.

2. A compound of claim 1, wherein
X is —CH$_2$OC(O)R$^2$;
Y$^1$ and Y$^2$ are each hydrogen;
Y$^3$ and Y$^4$ taken together are a methylene group;
Z$^1$ is hydroxy;
Z$^2$ is hydroxy; and
R$^2$ is alkyl, alkylamino, alkylcarbonyloxyalkyl, or hydroxyalkyl.

3. A compound of claim 2, wherein
X is —CH$_2$OC(O)R$^2$;
Y$^1$ and Y$^2$ are each hydrogen;
Y$^3$ and Y$^4$ taken together are a methylene group;
Z$^1$ is hydroxy;
Z$^2$ is hydroxy; and
R$^2$ is alkyl.

4. A compound of formula (I) as in claim 1 that is:
(2S)-2-[(1R,3R,7E, 17β)-1,3-dihydroxy-2-methylene-9,10-secoestra-5,7-dien-17-yl]propyl pivalate;
(2R)-2-[(1R,3R,7E,17β)-1,3-dihydroxy-2-methylene-9,10-secoestra-5,7-dien-17-yl]propyl pivalate;
(2S)-2-[(1R,3R,7E,17β)-1,3-dihydroxy-2-methylene-9,10-secoestra-5,7-dien-17-yl]propyl 2,2-dimethylbutanoate;
(2S)-2-[(1R,3R,7E,17β)-1,3-dihydroxy-2-methylene-9,10-secoestra-5,7-dien-17-yl]propyl tert-butylcarbamate;
(2S)-2-[(1R,3R,7E,17β)-1,3-dihydroxy-2-methylene-9,10-secoestra-5,7-dien-17-yl]propyl 2-(acetyloxy)-2-methylpropanoate;
(2S)-2-[(1R,3R,7E,17β)-1,3-dihydroxy-2-methylene-9,10-secoestra-5,7-dien-17-yl]propyl 2-hydroxy-2-methylpropanoate;
or a pharmaceutically acceptable salt thereof.

5. A pharmaceutical composition comprising a therapeutically effective amount of a compound of claim 1, or a salt thereof, in a pharmaceutically acceptable carrier.

* * * * *